(12) United States Patent
Buyse et al.

(10) Patent No.: US 8,969,542 B2
(45) Date of Patent: Mar. 3, 2015

(54) HPV POLYEPITOPE CONSTRUCTS AND USES THEREOF

(75) Inventors: Marie-Ange Buyse, Merelbeke (BE); Denise Baker, Poway, CA (US)

(73) Assignees: Genimmune N.V., Ghent (BE); PHARMEXA Inc., San Diego, CA (US)

( * ) Notice: Subject to any disclaimer, the term of this patent is extended or adjusted under 35 U.S.C. 154(b) by 1395 days.

(21) Appl. No.: 12/451,743

(22) PCT Filed: May 29, 2008

(86) PCT No.: PCT/EP2008/056586
§ 371 (c)(1),
(2), (4) Date: Jul. 1, 2010

(87) PCT Pub. No.: WO2008/145685
PCT Pub. Date: Dec. 4, 2008

(65) Prior Publication Data
US 2010/0272750 A1    Oct. 28, 2010

Related U.S. Application Data

(60) Provisional application No. 60/924,778, filed on May 31, 2007.

(30) Foreign Application Priority Data

Jun. 12, 2007 (EP) .................... 07110056

(51) Int. Cl.
| | | |
|---|---|---|
| *A61K 39/295* | (2006.01) | |
| *C07K 14/005* | (2006.01) | |
| *A61K 39/12* | (2006.01) | |
| *C07K 14/025* | (2006.01) | |
| *A61K 39/00* | (2006.01) | |
| *A61K 48/00* | (2006.01) | |

(52) U.S. Cl.
CPC .............. *C07K 14/005* (2013.01); *A61K 39/12* (2013.01); *A61K 39/00* (2013.01); *A61K 48/00* (2013.01); *A61K 2039/53* (2013.01); *C07K 2319/00* (2013.01); *C12N 2710/20022* (2013.01); *C12N 2710/20034* (2013.01); *C12N 2710/20051* (2013.01)
USPC ...................................... 536/23.72

(58) Field of Classification Search
None
See application file for complete search history.

(56) References Cited

U.S. PATENT DOCUMENTS

| 7,026,443 B1 | 4/2006 | Sette et al. |
| 2007/0134262 A1 | 6/2007 | Mattner et al. |

FOREIGN PATENT DOCUMENTS

| WO | WO 01/41799 | 6/2001 |
| WO | WO 2004/011650 | 2/2004 |
| WO | WO 2005/089164 | 9/2005 |
| WO | WO 2005089164 A2 * | 9/2005 |

OTHER PUBLICATIONS

International Search Report for PCT/EP2008/056586, mailed Oct. 15, 2008.
Written Opinion of the International Searching Authority for PCT/EP2008/056586, mailed Oct. 15, 2008.
Grgacic et al., "Virus-like particles: Passport to immune recognition", ScienceDirect, Methods vol. 40, No. 1, (Sep. 2006), pp. 60-65.
Brinkman et al., The efficacy of a DNA vaccine containing inserted and replicated regions of the E7 gene for treatment of HPV-16 inducted tumors, ScienceDirect, Vaccine, vol. 25, No. 17, (Apr. 5, 2007), pp. 3437-3444.
Villa et al., "Prophylactic quadrivalent human papillomavirus (types 6, 11, 16, and 18) L1 virus-like particle double-blind placebo-controlled multicentre phase II efficacy trial", Lancet Oncology, vol. 6, No. 5, (May 2005), pp. 281-278.
Galloway, "Papillomavirus vaccines in clinical trials", Lancet Infectious Diseases, vol. 3, No. 8, (Aug. 2003), pp. 469-475.
Sette A et al., "Epitope-based vaccines: an update on epitope identification, vaccine design and delivery", Current Opinion in Immunology, vol. 15, No. 4, (Jun. 2003), pp. 461-470.
Zwaveling, S. et al., "Established human papillomavirus type 16-expressing tumors are effectively eradicated following vaccination with long peptides", Journal of Immunology, vol. 169, No. 1, (Jul. 1, 2002), pp. 350-358.
Da Silva, D.M. et al., "Cervical cancer vaccines: emerging concepts and developments", Journal of Cellular Physiology, vol. 186, No. 2, (Feb. 2001), pp. 169-182.
Ishioka, G.Y. et al., "Utilization of MHC class I transgenic mice for development of minigene DNA vaccines encoding multiple HLA-restricted CTL epitopes", Journal of Immunology, vol. 162, No. 7, (Apr. 1, 1999), pp. 3915-3925.
Mateo, L. et al, "An HLA-A2 polyepitope vaccine for melanoma immunotherapy", Journal of Immunology, vol. 163, No. 7, (Oct. 1, 1999), pp. 4058-4063.

* cited by examiner

*Primary Examiner* — Bao Li
(74) *Attorney, Agent, or Firm* — Sterne, Kessler, Goldstein & Fox P.L.L.C.

(57) ABSTRACT

The present invention is directed to HPV polyepitope construct and the use thereof for the prevention and/or treatment of HPV infection.

13 Claims, 17 Drawing Sheets

Figure 9:
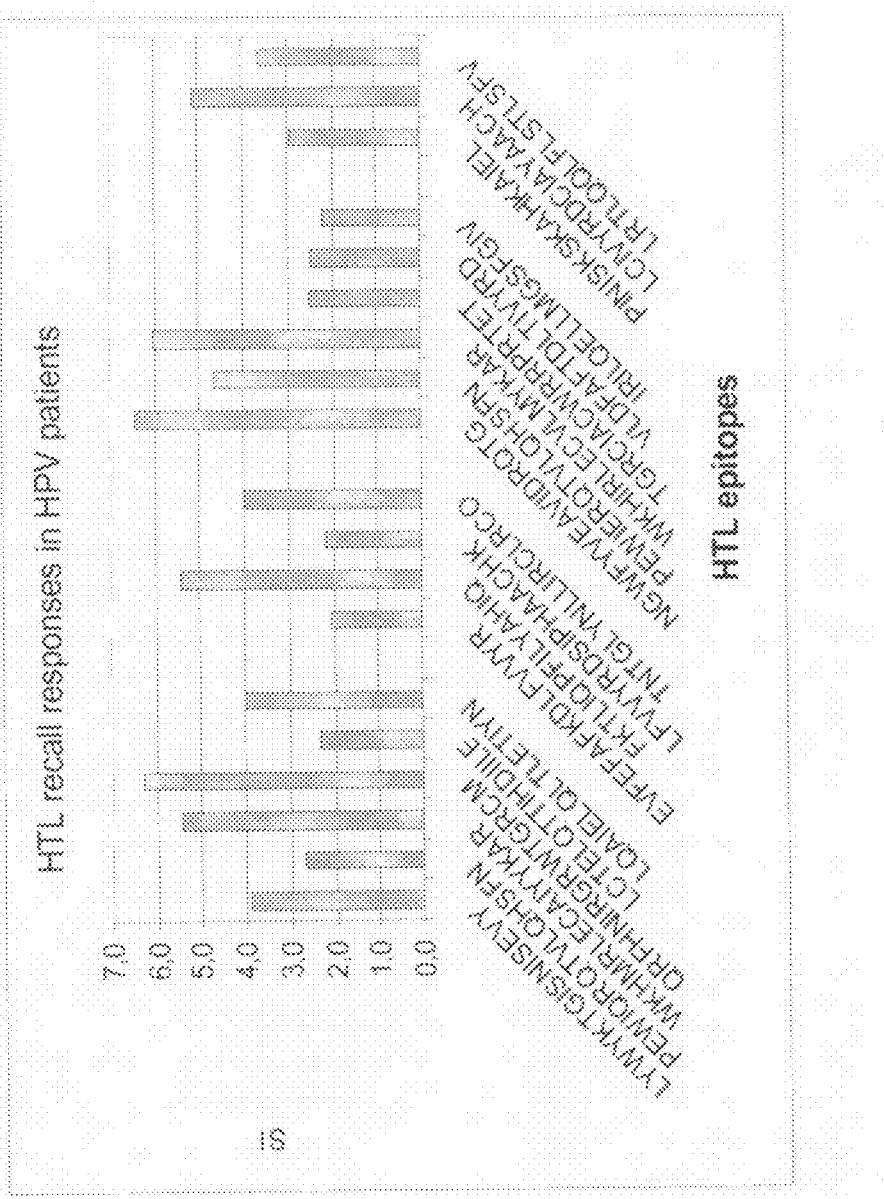

A.

ATCVSHRGLY - STDLRDHIDY - ATMCRHYKR - ILYAHIQCL - GTLGIVCPV - CYSLYGTTF - DSVYGDTLER - QVVPAYNISK - LYNLLIRCF - FVYIPLFLI - YYMTDAGTW - VVLLLVRYK - ISDYRHYCY - TVSATQLVK - STAAALYWYK - FVVYRDSIPK - SYFGMSFIHF - YMLDLQPETV - VYDFAFRDLCI - LQDKIIDHY - TLHDIILECV - KLTNTGLYNV - SVICFVNSK - MYVCCHVPL - SLQDIEITCV - CLYLHIQSL - AATKYPLLK - VYVFCFLLPM - KQGAMLAVFK - LSQMVQWAY - PYAVCDKCF - TVYVFCFLL - ATLQDIVLH - KSLFGMSLMK - GTGCNGWFY - RFHNIRGRF - KLLSK LLCV - STVSVGTAK - VAWDSVYYM - GYNTFYIEF - LYGVSFSEL - QVDYYGLYY - KSAIVTLTY - TLEKLTNTGLY

B.

GLYYVHEGIRTYFVQ - FLNTVAIPDSVQILV - QRFHNIRGRWTGRCM - TNTGLYNLLIRCLRCQ - IEFITFLGALKSFLK - PEWIQRQTVLQHSFN - LFVVYRDSIPHAACHK - IRTLEDLLMGTLGIV - LDLQPETTDLYCYEQ - LQAIEL QLTLETIYN - FQQLFLNTLSFVCPW - WKHMRLECAIYYKAR - LCTELQTTIHDIILE - FKTLIQPFILYAHIQ - LYWYKTGISNISEVY - EVFEFAFKDLFVVYR - HKAIELQMALQGLAQ - AKFVAAWTLKAAA

FIGURE 1

A.

| | | | |
|---|---|---|---|
| FYSKVSEFRW  –  | RTEVYQFAFR  – | VTTRYPLLR  – | VFTFPNPFPF  – |
| YTNWKFIYL  -  | SVYGETLEK  – | AVMCRHYKR  – | VYGTTLEKL  – |
| VVFIYIPLF  –  | KLLEKLLCI  - | GTGCNG  WFY  – | QTEPDTSNY  – |
| PYLHSRLVVF  – | LTDVSIACVY  – | HYTNWKFIF  – | FIYIPLFVI  – |
| MVMLMLVRFK  – | NTELYNLLI  – | FLFTDLTIV  – | FLLCFCVLL  – |
| ATTPIIHLK  -  | KLTNKG  ICDL  – | LQDKILDHY  – | NTGILTVTY  – |
| VMDDSEIAY  –  | STWHWTGCNK  – | SYFGMSFIHF  – | LSSALEIPY  – |
| LSQMVQWAY  –  | SLVFLLCFSV  – | TLYAHIQCL  – | VFTFPHAFPF  – |
| RQMNMSQWIK  – | TLQEIVLHV  – | AFTDLTIVY  | -ISFAGIVTK  – |
| YVVWDSIYYI  – | YYITETG  IW  – | FYSRIRELRF  – | VYQFAFKDL  – |
| FLLCFSVCL  –  | YQFAFKDLCV  – | SVYGTTLER  – | KVSEFRWYRY  – |
| ELDPVDLLCY – STAAALYWYR – VYVCAFAWLL | | | |

B.

| | | |
|---|---|---|
| EIVLHLEPQNELDPV  – | IRILQELLMGSFGIV  – | TGRCIACWRRPRTET  – |
| WKHIRLECVLMYKAR  – | LCIVYRDCIAYAACH  – | PEWIERQTVLQHSFN  – |
| PINISKSKAHKAIEL  – | LRTLQQLFLSTLSFV  – | FHSIAGQYRGQCNTC  – |
| TTPIIHLKGDANILK  – | DWVMAIFGVNPTVAEGF  – | PRKLHELSSALEIPY  – |
| FKTLIKPATLYAHIQ  – | TIPNSVQISVGYMTI  – | NGWFYVEAVIDRQTG  – |
| VLDFAFTDLTIVYRD  – | AKFVAAWTLKAAA | |

FIGURE 2

AFTDLTIVY  - STWHWTGCNK - KLLEKLLCI - YQFAFKDLCV -
MVMLMLVRFK -LQDKILDHY -FLLCFCVLL - SVYGTTLER - VTTRYPLLR
- TLQEIVLHV - YYITETGIW - VVFIYIPLF - QTEPDTSNY -
ELDPVDLLCY - LTDVSIACVY - RTEVYQFAFR - PYLHSRLVVF -
ISFAGIVTK - VMDDSEIAY - FYSRIRELRF - FIYIPLFVI -
VFTFPHAFPF - FYSKVSEFRW - SLVFLLCFSV -STAAALYWYR -
TLYAHIQCL - HYTNWKFIF - NTELYNLLI - SYFGMSFIHF -
KLTNKGICDL -SVYGETLEK - VYVCAFAWLL - VYGTTLEKL -
LSQMVQWAY - YVVWDSIYYI - GTGCNGWFY - AVMCRHYKR -
FLLCFSVCL -VYQFAFKDL - KVSEFRWYRY - YTNWKFIYL - LSSALEIPY
- FLFTDLTIV - ATTPIIHLK -RQMNMSQWIK -NTGILTVTY -
VFTFPNPFPF

FIGURE 3

KSLFGMSLMK - STAAALYWYK - CYSLYGTTF -VAWDSVYYM -
STDLRDHIDY -ISDYRHYCY - QVVPAYNISK - GYNTFYIEF -
LQDKIIDHY - CLYLHIQSL - ATLQDIVLH - TVYVFCFLL - ILYAHIQCL
- LYNLLIRCF - FVYIPLFLI - TVSATQLVK - GTGCNGWFY -
AATKYPLLK - VYVFCFLLPM - TLHDIILECV - LYGVSFSEL -
QVDYYGLYY - YYMTDAGTW - PYAVCDKCF - KQGAMLAVFK -
VVLLLVRYK - SYFGMSFIHF - KLLSKLLCV - ATMCRHYKR -
STVSVGTAK - LSQMVQWAY - KLTNTGLYNV - ATCVSHRGLY -
KSAIVTLTY - DSVYGDTLER - MYVCCHVPL - RFHNIRGRF -
FVVYRDSIPK - SLQDIEITCV - VYDFAFRDLCI - YMLDLQPETV -
GTLGIVCPV - SVICFVNSK - TLEKLTNTGLY

FIGURE 4

FIGURE 5

A. ICCG6137 Amino acid sequence

MGMQVQIQSLFLLLLWVPGSRGAFTDLTIVYNSTWHWTGCNKKAAAKLLEKLLCINA
YQFAFKDLCVKMVMLMLVRFKNAALQDKILDHYKAAFLLCFCVLLNSVYGTTLERNA
AVTTRYPLLRNATLQEIVLHVNYYITETGIWKVVFIYIPLFNQTEPDTSNYGAAELD
PVDLLCYKAAALTDVSIACVYNAARTEVYQFAFRNPYLHSRLVVFNISFAGIVTKKV
MDDSEIAYNAFYSRIRELRFKAAAFIYIPLFVIKAVFTFPHAFPFNAFYSKVSEFRW
KSLVFLLCFSVNASTAAALYWYRKATLYAHIQCLNAAHYTNWKFIFNAANTELYNLL
INASYFGMSFIHFKLTNKGICDLNSVYGETLEKNVYVCAFAWLLNVYGTTLEKLKLS
QMVQWAYKAAAYVVWDSIYYINGTGCNGWFYGAAAVMCRHYKRNFLLCFSVCLNAVY
QFAFKDLKAAKVSEFRWYRYKYTNWKFIYLNAALSSALEIPYKAAFLFTDLTIVNAA
TTPIIHLKNAAARQMNMSQWIKNTGILTVTYNVFTFPNPFPFKAAAEIVLHLEPQNE
LDPVGPGPGIRILQELLMGSFGIVGPGPGTGRCIACWRRPRTETGPGPGWKHIRLEC
VLMYKARGPGPGLCIVYRDCIAYAACHGPGPGPEWIERQTVLQHSFNGPGPGPINIS
KSKAHKAIELGPGPGLRTLQQLFLSTLSFVGPGPGFHSIAGQYRGQCNTCGPGPGTT
PIIHLKGDANILKGPGPGDWVMAIFGVNPTVAEGFGPGPGPRKLHELSSALEIPYGP
GPGPGFKTLIKPATLYAHIQGPGPGTIPNSVQISVGYMTIGPGPGNGWFYVEAVIDRQT
GGPGPGVLDFAFTDLTIVYRDGPGPGAKFVAAWTLKAAA
(SEQ ID NO 123)

B. ICCG6137 DNA sequence

ATGGGCATGCAGGTGCAGATCCAGAGCCTGTTCCTGCTGCTGCTGTGGGTGCCCGGC
AGCAGGGGCGCTTTCACCGACCTGACCATCGTGTACAACAGCACCTGGCACTGGACC
GGCTGCAACAAGAAAGCCGCTGCCAAGCTGCTGGAAAAGCTGCTGTGCATCAACGCC
TATCAGTTTGCCTTCAAGGACCTGTGCGTGAAGATGGTGATGCTGATGCTGGTGCGG
TTCAAGAATGCCGCTCTCCAGGACAAGATCCTGGACCACTACAAGGCCGCCTTTCTG
CTGTGCTTCTGCGTGCTGCTGAACAGCGTGTACGGCACCACCCTGGAACGGAACGCC
GCCGTGACCACCAGATACCCCCTGCTGCGGAATGCCACCCTCCAGGAAATCGTCCTG
CACGTCAATTACTACATCACCGAGACCGGCATCTGGAAGGTGGTGTTCATCTACATC
CCCCTGTTCAACCAGACCGAGCCCGACACCAGCAACTACGGAGCCGCCGAACTCGAT
CCCGTGGACCTGCTGTGCTACAAAGCCGCTGCCCTGACCGACGTGAGCATCGCCTGC
GTGTACAACGCCGCCAGGACCGAGGTGTACCAGTTTGCCTTTCGGAACCCCTACCTG
CACAGCAGACTGGTGGTGTTTAACATCAGCTTCGCCGGCATCGTGACCAAGAAAGTG
ATGGACGACAGCGAGATCGCCTACAACGCCTTCTACAGCCGGATCAGAGAGCTGAGG
TTCAAAGCCGCTGCCTTTATCTACATTCCTCTGTTCGTGATCAAGGCCGTGTTCACC
TTCCCCCACGCCTTCCCTTTCAATGCCTTCTACTCCAAGGTGTCCGAGTTCCGGTGG
AAGAGCCTGGTGTTCCTGCTGTGTTTCAGCGTGAACGCCAGCACCGCCGCTGCCCTG
TACTGGTACAGGAAGGCCACCCTGTACGCCCATATCCAGTGCCTGAATGCCGCCCAC
TACACCAACTGGAAGTTCATCTTCAATGCCGCCAACACCGAGCTGTACAACCTGCTG
ATCAACGCCAGCTACTTCGGCATGAGCTTCATCCACTTCAAGCTGACCAACAAGGGC
ATCTGCGACCTGAACTCCGTGTACGGCGAGACACTGGAAAAGAACGTGTACGTGTGC
GCCTTCGCCTGGCTGCTGAACGTGTATGGCACAACACTGGAAAAACTGAAGCTGTCC
CAGATGGTGCAGTGGGCCTATAAAGCCGCCGCCTACGTGGTGTGGGACAGCATCTAC
TATATCAACGGCACCGGCTGTAACGGCTGGTTTTACGGCGCCGCTGCCGTGATGTGC
CGGCACTACAAGCGGAATTTTCTGCTGTGTTTTTCCGTGTGCCTGAACGCCGTGTAT

CAGTTCGCCTTTAAGGATCTGAAGGCTGCCAAAGTGTCTGAGTTCAGATGGTACAGG
TACAAGTACACAAATTGGAAGTTTATCTATCTGAACGCCGCCCTGAGCAGCGCCCTG
GAAATCCCTATAAGGCTGCCTTCCTGTTCACCGATCTGACTATTGTGAACGCCGCC
ACCACCCCCATCATCCACCTGAAAAACGCCGCTGCCAGGCAGATGAACATGAGCCAG
TGGATCAAGAACACCGGCATCCTGACCGTGACCTACAACGTGTTTACCTTTCCCAAC
CCTTTCCCCTTTAAAGCCGCTGCCGAGATCGTGCTGCACCTGGAACCCCAGAACGAG
CTGGACCCTGTGGGCCCTGGCCCTGGCATCAGAATCCTCCAGGAACTGCTGATGGGC
AGCTTCGGCATCGTGGGCCCAGGCCCCGGAACCGGCCGGTGCATCGCCTGTTGGCGG
AGGCCCCGGACCGAGACAGGCCCTGGACCCGGCTGGAAGCACATCCGGCTGGAATGC
GTGCTGATGTACAAGGCCAGGGGACCCGGCCCTGGCCTCTGTATCGTGTACCGCGAC
TGCATCGCCTACGCCGCCTGCCACGGCCCAGGACCTGGCCCCGAGTGGATCGAGCGG
CAGACCGTGCTCCAGCATAGCTTCAACGGACCCGGACCAGGCCCCATCAACATCAGC
AAGAGCAAGGCCCACAAGGCCATCGAGCTGGGCCCTGGGCCCGGACTGCGGACCCTC
CAGCAGCTGTTCCTGAGCACCCTGAGCTTCGTGGGACCTGGGCCAGGCTTCCACAGC
ATCGCCGGCCAGTACCGGGGCCAGTGCAACACCTGCGGCCCAGGGCCAGGCACCACA
CCTATTATTCACCTGAAGGGCGACGCCAACATCCTGAAGGGGCCAGGACCCGGCGAC
TGGGTGATGGCCATCTTCGGCGTGAACCCCACCGTGGCCGAGGGCTTCGGACCTGGA
CCTGGGCCTAGGAAGCTGCACGAGCTGTCCTCTGCCCTGGAAATTCCTTACGGCCCT
GGCCCAGGCTTCAAGACCCTGATCAAGCCCGCCACACTGTATGCCCACATTCAGGGC
CCTGGACCAGGCACCATCCCCAACAGCGTGCAGATCAGCGTGGGCTACATGACCATC
GGACCAGGGCCTGGCAATGGCTGGTTCTACGTGGAGGCCGTGATCGACAGGCAGACC
GGCGGACCTGGCCCAGGGGTGCTGGACTTCGCCTTTACAGACCTGACAATTGTGTAC
CGGGACGGCCCTGGGCCTGGCGCCAAGTTCGTGGCCGCCTGGACCCTGAAGGCCGCT
GCCTGA
(SEQ ID NO 124)

C.

AFTDLTIVYNSTWHWTGCNKKAAAKLLEKLLCINAYQFAFKDLCVKMVMLMLVRFKN
AALQDKILDHYKAAFLLCFCVLLNSVYGTTLERNAAVTTRYPLLRNATLQEIVLHVN
YYITETGIWKVVFIYIPLFNQTEPDTSNYGAAELDPVDLLCYKAAALTDVSIACVYN
AARTEVYQFAFRNPYLHSRLVVFNISFAGIVTKKVMDDSEIAYNAFYSRIRELRFKA
AAFIYIPLFVIKAVFTFPHAFPFNAFYSKVSEFRWKSLVFLLCFSVNASTAAALYWY
RKATLYAHIQCLNAAHYTNWKFIFNAANTELYNLLINASYFGMSFIHFKLTNKGICD
LNSVYGETLEKNVYVCAFAWLLNVYGTTLEKLKLSQMVQWAYKAAAYVVWDSIYYIN
GTGCNGWFYGAAAVMCRHYKRNFLLCFSVCLNAVYQFAFKDLKAAKVSEFRWYRYKY
TNWKFIYLNAALSSALEIPYKAAFLFTDLTIVNAATTPIIHLKNAAARQMNMSQWIK
NTGILTVTYNVFTFPNPFPFKAAAEIVLHLEPQNELDPVGPGPGIRILQELLMGSFG
IVGPGPGTGRCIACWRRPRTETGPGPGWKHIRLECVLMYKARGPGPGLCIVYRDCIA
YAACHGPGPGPEWIERQTVLQHSFNGPGPGPINISKSKAHKAIELGPGPGLRTLQQL
FLSTLSFVGPGPGFHSIAGQYRGQCNTCGPGPGTTPIIHLKGDANILKGPGPGDWVM
AIFGVNPTVAEGFGPGPGPRKLHELSSALEIPYGPGPGFKTLIKPATLYAHIQGPGP
GTIPNSVQISVGYMTIGPGPGNGWFYVEAVIDRQTGGPGPGVLDFAFTDLTIVYRDG
PGPGAKFVAAWTLKAAA
(SEQ ID NO 156)

FIGURE 5 cont.1

D.

```
GCTTTCACCGACCTGACCATCGTGTACAACAGCACCTGGCACTGGACCGGCTGCAAC
AAGAAAGCCGCTGCCAAGCTGCTGGAAAAGCTGCTGTGCATCAACGCCTATCAGTTT
GCCTTCAAGGACCTGTGCGTGAAGATGGTGATGCTGATGCTGGTGCGGTTCAAGAAT
GCCGCTCTCCAGGACAAGATCCTGGACCACTACAAGGCCGCCTTTCTGCTGTGCTTC
TGCGTGCTGCTGAACAGCGTGTACGGCACCACCCTGGAACGGAACGCCGCCGTGACC
ACCAGATACCCCCTGCTGCGGAATGCCACCCTCCAGGAAATCGTCCTGCACGTCAAT
TACTACATCACCGAGACCGGCATCTGGAAGGTGGTGTTCATCTACATCCCCCTGTTC
AACCAGACCGAGCCCGACACCAGCAACTACGGAGCCGCCGAACTCGATCCCGTGGAC
CTGCTGTGCTACAAAGCCGCTGCCCTGACCGACGTGAGCATCGCCTGCGTGTACAAC
GCCGCCAGGACCGAGGTGTACCAGTTTGCCTTTCGGAACCCCTACCTGCACAGCAGA
CTGGTGGTGTTTAACATCAGCTTCGCCGGCATCGTGACCAAGAAAGTGATGGACGAC
AGCGAGATCGCCTACAACGCCTTCTACAGCCGGATCAGAGAGCTGAGGTTCAAAGCC
GCTGCCTTTATCTACATTCCTCTGTTCGTGATCAAGGCCGTGTTCACCTTCCCCCAC
GCCTTCCCTTTCAATGCCTTCTACTCCAAGGTGTCCGAGTTCCGGTGGAAGAGCCTG
GTGTTCCTGCTGTGTTTCAGCGTGAACGCCAGCACCGCCGCTGCCCTGTACTGGTAC
AGGAAGGCCACCCTGTACGCCCATATCCAGTGCCTGAATGCCGCCCACTACACCAAC
TGGAAGTTCATCTTCAATGCCGCCAACACCGAGCTGTACAACCTGCTGATCAACGCC
AGCTACTTCGGCATGAGCTTCATCCACTTCAAGCTGACCAACAAGGGCATCTGCGAC
CTGAACTCCGTGTACGGCGAGACACTGGAAAAGAACGTGTACGTGTGCGCCTTCGCC
TGGCTGCTGAACGTGTATGGCACAACACTGGAAAAACTGAAGCTGTCCCAGATGGTG
CAGTGGGCCTATAAAGCCGCCGCCTACGTGGTGTGGGACAGCATCTACTATATCAAC
GGCACCGGCTGTAACGGCTGGTTTTACGGCGCCGCTGCCGTGATGTGCCGGCACTAC
AAGCGGAATTTTCTGCTGTGTTTTTCCGTGTGCCTGAACGCCGTGTATCAGTTCGCC
TTTAAGGATCTGAAGGCTGCCAAAGTGTCTGAGTTCAGATGGTACAGGTACAAGTAC
ACAAATTGGAAGTTTATCTATCTGAACGCCGCCCTGAGCAGCGCCCTGGAAATCCCC
TATAAGGCTGCCTTCCTGTTCACCGATCTGACTATTGTGAACGCCGCCACCACCCCC
ATCATCCACCTGAAAAACGCCGCTGCCAGGCAGATGAACATGAGCCAGTGGATCAAG
AACACCGGCATCCTGACCGTGACCTACAACGTGTTTACCTTTCCCAACCCTTTCCCC
TTTAAAGCCGCTGCCGAGATCGTGCTGCACCTGGAACCCCAGAACGAGCTGGACCCT
GTGGGCCCTGGCCCTGGCATCAGAATCCTCCAGGAACTGCTGATGGGCAGCTTCGGC
ATCGTGGGCCCAGGCCCCGGAACCGGCCGGTGCATCGCCTGTTGGCGGAGGCCCCGG
ACCGAGACAGGCCCTGGACCCGGCTGGAAGCACATCCGGCTGGAATGCGTGCTGATG
TACAAGGCCAGGGGACCCGGCCCTGGCCTCTGTATCGTGTACCGCGACTGCATCGCC
TACGCCGCCTGCCACGGCCCAGGACCTGGCCCCGAGTGGATCGAGCGGCAGACCGTG
CTCCAGCATAGCTTCAACGGACCCGGACCAGGCCCCATCAACATCAGCAAGAGCAAG
GCCCACAAGGCCATCGAGCTGGGCCCTGGGCCCGGACTGCGGACCCTCCAGCAGCTG
TTCCTGAGCACCCTGAGCTTCGTGGGACCTGGGCCAGGCTTCCACAGCATCGCCGGC
CAGTACCGGGGCCAGTGCAACACCTGCGGCCCAGGGCCAGGCACCACACCTATTATT
CACCTGAAGGGCGACGCCAACATCCTGAAGGGGCCAGGACCCGGCGACTGGGTGATG
GCCATCTTCGGCGTGAACCCCACCGTGGCCGAGGGCTTCGGACCTGGACCTGGGCCT
AGGAAGCTGCACGAGCTGTCCTCTGCCCTGGAAATTCCTTACGGCCCTGGCCCAGGC
TTCAAGACCCTGATCAAGCCCGCCACACTGTATGCCCACATTCAGGGCCCTGGACCA
GGCACCATCCCCAACAGCGTGCAGATCAGCGTGGGCTACATGACCATCGGACCAGGG
CCTGGCAATGGCTGGTTCTACGTGGAGGCCGTGATCGACAGGCAGACCGGCGGACCT
GGCCCAGGGGTGCTGGACTTCGCCTTTACAGACCTGACAATTGTGTACCGGGACGGC
CCTGGGCCTGGCGCCAAGTTCGTGGCCGCCTGGACCCTGAAGGCCGCTGCC
(SEQ ID NO 157)
```

FIGURE 6

A. ICCG6138 Amino acid sequence

```
MGMQVQIQSLFLLLLWVPGSRGFYSKVSEFRWKAARTEVYQFAFRNAAVTTRYPLLR
NVFTFPNPFPFNYTNWKFIYLNASVYGETLEKGAAVMCRHYKRNAVYGTTLEKLKVV
FIYIPLFGAAKLLEKLLCINGTGCNGWFYNQTEPDTSNYNAAAPYLHSRLVVFGAAA
LTDVSIACVYNAHYTNWKFIFGAAFIYIPLFVIKAAAMVMLMLVRFKNAANTELYNL
LINFLFTDLTIVNFLLCFCVLLNAATTPIIHLKGAAKLTNKGICDLNALQDKILDHY
KNTGILTVTYGAAAVMDDSEIAYNSTWHWTGCNKKAASYFGMSFIHFKLSSALEIPY
KLSQMVQWAYNSLVFLLCFSVNATLYAHIQCLNVFTFPHAFPFNAAARQMNMSQWIK
NATLQEIVLHVNAAFTDLTIVYNISFAGIVTKKYVVWDSIYYINYYITETGIWKAAA
FYSRIRELRFKVYQFAFKDLKAFLLCFSVCLNAAYQFAFKDLCVKSVYGTTLERNKV
SEFRWYRYKAAELDPVDLLCYKSTAAALYWYRKAAAVYVCAFAWLLEIVLHLEPQNE
LDPVGPGPGIRILQELLMGSFGIVGPGPGTGRCIACWRRPRTETGPGPGWKHIRLEC
VLMYKARGPGPGLCIVYRDCIAYAACHGPGPGPEWIERQTVLQHSFNGPGPGPINIS
KSKAHKAIELGPGPGLRTLQQLFLSTLSFVGPGPGFHSIAGQYRGQCNTCGPGPGTT
PIIHLKGDANILKGPGPGDWVMAIFGVNPTVAEGFGPGPGPRKLHELSSALEIPYGP
GPGFKTLIKPATLYAHIQGPGPGTIPNSVQISVGYMTIGPGPGNGWFYVEAVIDRQT
GGPGPGVLDFAFTDLTIVYRDGPGPGAKFVAAWTLKAAA
```
(SEQ ID NO 125)

B. ICCG6138 DNA sequence

```
ATGGGCATGCAGGTGCAGATCCAGAGCCTGTTCCTGCTGCTGCTGTGGGTGCCCGGC
AGCCGGGGCTTCTACAGCAAGGTGTCCGAGTTCCGGTGGAAGGCCGCCAGGACCGAG
GTGTACCAGTTCGCCTTCCGGAACGCCGCCGTGACCACCAGATACCCCCTGCTGCGG
AACGTGTTCACCTTCCCCAACCCCTTCCCTTTCAACTACACCAACTGGAAGTTCATC
TACCTGAACGCCAGCGTGTACGGCGAGACCCTGGAAAAGGGAGCAGCCGTGATGTGC
CGGCACTACAAGCGGAACGCCGTGTACGGCACCACACTGGAAAAGCTGAAGGTGGTG
TTCATCTACATCCCCCTGTTCGGAGCCGCCAAGCTGCTGGAAAAACTGCTGTGCATC
AACGGCACCGGCTGCAACGGCTGGTTCTACAACCAGACCGAGCCCGACACCAGCAAC
TACAATGCTGCCGCCCCTACCTGCACAGCAGACTGGTGGTGTTTGGGGCTGCCGCC
CTGACCGACGTGAGCATCGCCTGCGTGTACAACGCCCACTACACAAATTGGAAATTC
ATTTTTGGAGCCGCCTTCATCTATATTCCTCTGTTCGTGATCAAAGCCGCCGCTATG
GTGATGCTGATGCTGGTGCGGTTCAAGAACGCCGCCAACACCGAGCTGTACAACCTG
CTGATCAACTTCCTGTTCACCGACCTGACCATCGTGAACTTTCTCCTGTGTTTCTGC
GTGCTCCTGAATGCCGCCACAACCCCCATCATCCACCTGAAGGGAGCCGCCAAACTG
ACCAACAAGGGCATCTGCGACCTGAATGCCCTCCAGGACAAGATCCTGGACCACTAC
AAGAACACCGGCATCCTGACCGTGACCTATGGAGCCGCTGCCGTGATGGACGACAGC
GAGATCGCCTACAACAGCACCTGGCACTGGACCGGCTGTAACAAGAAGGCCGCCTCC
TACTTCGGCATGAGCTTCATCCACTTCAAGCTGTCCAGCGCCCTGGAAATCCCCTAC
AAGCTGTCCCAGATGGTGCAGTGGGCCTACAACTCCCTGGTGTTCCTGCTGTGTTTC
AGCGTGAACGCAACCCTCTATGCCCACATCCAGTGCCTGAATGTGTTTACCTTCCCT
CACGCCTTTCCCTTCAATGCCGCCGCCAGACAGATGAACATGAGCCAGTGGATCAAG
AATGCCACCCTCCAGGAGATTGTCCTGCACGTCAATGCCGCCTTTACTGATCTGACT
ATCGTGTACAACATCAGCTTCGCCGGCATCGTGACCAAGAAATACGTGGTGTGGGAC
AGCATCTACTACATCAATTACTACATCACCGAGACCGGCATCTGGAAAGCTGCCGCC
```

```
TTCTACAGCCGGATCAGGGAGCTGAGGTTCAAAGTGTATCAGTTTGCTTTCAAAGAC
CTGAAAGCCTTCCTGCTGTGCTTTTCCGTGTGCCTGAACGCCGCCTACCAGTTTGCC
TTTAAGGATCTGTGCGTGAAGAGCGTGTATGGCACAACCCTGGAACGGAACAAAGTG
TCTGAGTTCCGCTGGTACAGGTATAAGGCCGCCGAACTCGATCCCGTGGATCTGCTG
TGTTACAAGAGCACTGCCGCCGCACTGTACTGGTATAGGAAGGCTGCCGCCGTGTAC
GTGTGCGCCTTCGCCTGGCTGCTGGAGATCGTGCTGCACCTGGAACCCCAGAACGAG
CTGGACCCTGTGGGCCCTGGCCCTGGCATCAGAATCCTCCAGGAACTGCTGATGGGC
AGCTTCGGCATCGTGGGCCCAGGCCCCGGAACCGGCCGGTGCATCGCCTGTTGGCGG
AGGCCCCGGACCGAGACAGGCCCTGGACCCGGCTGGAAGCACATCCGGCTGGAATGC
GTGCTGATGTACAAGGCCAGGGGACCCGGCCCTGGCCTCTGTATCGTGTACCGCGAC
TGCATCGCCTACGCCGCCTGCCACGGCCCAGGACCTGGCCCCGAGTGGATCGAGCGG
CAGACCGTGCTCCAGCATAGCTTCAACGGACCCGGACCAGGCCCCATCAACATCAGC
AAGAGCAAGGCCCACAAGGCCATCGAGCTGGGCCCTGGGCCCGGACTGCGGACCCTC
CAGCAGCTGTTCCTGAGCACCCTGAGCTTCGTGGGACCTGGGCCAGGCTTCCACAGC
ATCGCCGGCCAGTACCGGGGCCAGTGCAACACCTGCGGCCCAGGGCCAGGCACCACA
CCTATTATTCACCTGAAGGGCGACGCCAACATCCTGAAGGGGCCAGGACCCGGCGAC
TGGGTGATGGCCATCTTCGGCGTGAACCCCACCGTGGCCGAGGGCTTCGGACCTGGA
CCTGGGCCTAGGAAGCTGCACGAGCTGTCCTCTGCCCTGGAAATTCCTTACGGCCCT
GGCCCAGGCTTCAAGACCCTGATCAAGCCCGCCACACTGTATGCCCACATTCAGGGC
CCTGGACCAGGCACCATCCCCAACAGCGTGCAGATCAGCGTGGGCTACATGACCATC
GGACCAGGGCCTGGCAATGGCTGGTTCTACGTGGAGGCCGTGATCGACAGGCAGACC
GGCGGACCTGGCCCAGGGGTGCTGGACTTCGCCTTTACAGACCTGACAATTGTGTAC
CGGGACGGCCCTGGGCCTGGCGCCAAGTTCGTGGCCGCCTGGACCCTGAAGGCCGCT
GCCTGA
(SEQ ID NO 126)

C.

FYSKVSEFRWKAARTEVYQFAFRNAAVTTRYPLLRNVFTFPNPFPFNYTNWKFIYLN
ASVYGETLEKGAAVMCRHYKRNAVYGTTLEKLKVVFIYIPLFGAAKLLEKLLCINGT
GCNGWFYNQTEPDTSNYNAAAPYLHSRLVVFGAAALTDVSIACVYNAHYTNWKFIFG
AAFIYIPLFVIKAAAMVMLMLVRFKNAANTELYNLLINFLFTDLTIVNFLLCFCVLL
NAATTPIIHLKGAAKLTNKGICDLNALQDKILDHYKNTGILTVTYGAAAVMDDSEIA
YNSTWHWTGCNKKAASYFGMSFIHFKLSSALEIPYKLSQMVQWAYNSLVFLLCFSVN
ATLYAHIQCLNVFTFPHAFPFNAAARQMNMSQWIKNATLQEIVLHVNAAFTDLTIVY
NISFAGIVTKKYVVWDSIYYINYYITETGIWKAAAFYSRIRELRFKVYQFAFKDLKA
FLLCFSVCLNAAYQFAFKDLCVKSVYGTTLERNKVSEFRWYRYKAAELDPVDLLCYK
STAAALYWYRKAAAVYVCAFAWLLEIVLHLEPQNELDPVGPGPGIRILQELLMGSFG
IVGPGPGTGRCIACWRRPRTETGPGPGWKHIRLECVLMYKARGPGPGLCIVYRDCIA
YAACHGPGPGPEWIERQTVLQHSFNGPGPGPINISKSKAHKAIELGPGPGLRTLQQL
FLSTLSFVGPGPGFHSIAGQYRGQCNTCGPGPGTTPIIHLKGDANILKGPGPGDWVM
AIFGVNPTVAEGFGPGPGPRKLHELSSALEIPYGPGPGFKTLIKPATLYAHIQGPGP
GTIPNSVQISVGYMTIGPGPGNGWFYVEAVIDRQTGGPGPGVLDFAFTDLTIVYRDG
PGPGAKFVAAWTLKAAA
(SEQ ID NO 158)
```

FIGURE 6 cont.1

D.

```
TTCTACAGCAAGGTGTCCGAGTTCCGGTGGAAGGCCGCCAGGACCGAGGTGTACCAG
TTCGCCTTCCGGAACGCCGCCGTGACCACCAGATACCCCCTGCTGCGGAACGTGTTC
ACCTTCCCCAACCCCTTCCCTTTCAACTACACCAACTGGAAGTTCATCTACCTGAAC
GCCAGCGTGTACGGCGAGACCCTGGAAAAGGGAGCAGCCGTGATGTGCCGGCACTAC
AAGCGGAACGCCGTGTACGGCACCACACTGGAAAAGCTGAAGGTGGTGTTCATCTAC
ATCCCCCTGTTCGGAGCCGCCAAGCTGCTGGAAAAACTGCTGTGCATCAACGGCACC
GGCTGCAACGGCTGGTTCTACAACCAGACCGAGCCCGACACCAGCAACTACAATGCT
GCCGCCCCCTACCTGCACAGCAGACTGGTGGTGTTTGGGGCTGCCGCCCTGACCGAC
GTGAGCATCGCCTGCGTGTACAACGCCCACTACACAAATTGGAAATTCATTTTTGGA
GCCGCCTTCATCTATATTCCTCTGTTCGTGATCAAAGCCGCCGCTATGGTGATGCTG
ATGCTGGTGCGGTTCAAGAACGCCGCCAACACCGAGCTGTACAACCTGCTGATCAAC
TTCCTGTTCACCGACCTGACCATCGTGAACTTTCTCCTGTGTTTCTGCGTGCTCCTG
AATGCCGCCACAACCCCCATCATCCACCTGAAGGGAGCCGCCAAACTGACCAACAAG
GGCATCTGCGACCTGAATGCCCTCCAGGACAAGATCCTGGACCACTACAAGAACACC
GGCATCCTGACCGTGACCTATGGAGCCGCTGCCGTGATGGACGACAGCGAGATCGCC
TACAACAGCACCTGGCACTGGACCGGCTGTAACAAGAAGGCCGCCTCCTACTTCGGC
ATGAGCTTCATCCACTTCAAGCTGTCCAGCGCCCTGGAAATCCCCTACAAGCTGTCC
CAGATGGTGCAGTGGGCCTACAACTCCCTGGTGTTCCTGCTGTGTTTCAGCGTGAAC
GCAACCCTCTATGCCCACATCCAGTGCCTGAATGTGTTTACCTTCCCTCACGCCTTT
CCCTTCAATGCCGCCGCCAGACAGATGAACATGAGCCAGTGGATCAAGAATGCCACC
CTCCAGGAGATTGTCCTGCACGTCAATGCCGCCTTTACTGATCTGACTATCGTGTAC
AACATCAGCTTCGCCGGCATCGTGACCAAGAAATACGTGGTGTGGGACAGCATCTAC
TACATCAATTACTACATCACCGAGACCGGCATCTGGAAAGCTGCCGCCTTCTACAGC
CGGATCAGGGAGCTGAGGTTCAAAGTGTATCAGTTTGCTTTCAAAGACCTGAAAGCC
TTCCTGCTGTGCTTTTCCGTGTGCCTGAACGCCGCCTACCAGTTTGCCTTTAAGGAT
CTGTGCGTGAAGAGCGTGTATGGCACAACCCTGGAACGGAACAAAGTGTCTGAGTTC
CGCTGGTACAGGTATAAGGCCGCCGAACTCGATCCCGTGGATCTGCTGTGTTACAAG
AGCACTGCCGCCGCACTGTACTGGTATAGGAAGGCTGCCGCCGTGTACGTGTGCGCC
TTCGCCTGGCTGCTGGAGATCGTGCTGCACCTGGAACCCCAGAACGAGCTGGACCCT
GTGGGCCCTGGCCCTGGCATCAGAATCCTCCAGGAACTGCTGATGGGCAGCTTCGGC
ATCGTGGGCCCAGGCCCCGGAACCGGCCGGTGCATCGCCTGTTGGCGGAGGCCCCGG
ACCGAGACAGGCCCTGGACCCGGCTGGAAGCACATCCGGCTGGAATGCGTGCTGATG
TACAAGGCCAGGGGACCCGGCCCTGGCCTCTGTATCGTGTACCGCGACTGCATCGCC
TACGCCGCCTGCCACGGCCCAGGACCTGGCCCCGAGTGGATCGAGCGGCAGACCGTG
CTCCAGCATAGCTTCAACGGACCCGGACCAGGCCCCATCAACATCAGCAAGAGCAAG
GCCCACAAGGCCATCGAGCTGGGCCCTGGGCCCGGACTGCGGACCCTCCAGCAGCTG
TTCCTGAGCACCCTGAGCTTCGTGGGACCTGGGCCAGGCTTCCACAGCATCGCCGGC
CAGTACCGGGGCCAGTGCAACACCTGCGGCCCAGGGCCAGGCACCACACCTATTATT
CACCTGAAGGGCGACGCCAACATCCTGAAGGGGCCAGGACCCGGCGACTGGGTGATG
GCCATCTTCGGCGTGAACCCCACCGTGGCCGAGGGCTTCGGACCTGGACCTGGGCCT
AGGAAGCTGCACGAGCTGTCCTCTGCCCTGGAAATTCCTTACGGCCCTGGCCCAGGC
TTCAAGACCCTGATCAAGCCCGCCACACTGTATGCCCACATTCAGGGCCCTGGACCA
GGCACCATCCCCAACAGCGTGCAGATCAGCGTGGGCTACATGACCATCGGACCAGGG
CCTGGCAATGGCTGGTTCTACGTGGAGGCCGTGATCGACAGGCAGACCGGCGGACCT
GGCCCAGGGGTGCTGGACTTCGCCTTTACAGACCTGACAATTGTGTACCGGGACGGC
CCTGGGCCTGGCGCCAAGTTCGTGGCCGCCTGGACCCTGAAGGCCGCTGCC
(SEQ ID NO 159)
```

FIGURE 6 cont.2

FIGURE 7

A. ICCG6149 Amino acid sequence

MGMQVQIQSLFLLLLWVPGSRGKSLFGMSLMKNSTAAALYWYKKAACYSLYGTTFKA
AAVAWDSVYYMKSTDLRDHIDYNISDYRHYCYKAAQVVPAYNISKNGYNTFYIEFKL
QDKIIDHYKAACLYLHIQSLNAAAATLQDIVLHGTVYVFCFLLNAILYAHIQCLNAA
LYNLLIRCFKAAFVYIPLFLINTVSATQLVKNGTGCNGWFYNAATKYPLLKNVYVFC
FLLPMNATLHDIILECVKAAALYGVSFSELKQVDYYGLYYGAYYMTDAGTWNAAPYA
VCDKCFKQGAMLAVFKKAAAVVLLLVRYKNAAASYFGMSFIHFKAAKLLSKLLCVNA
AAATMCRHYKRNAAASTVSVGTAKNAALSQMVQWAYKLTNTGLYNVNAAATCVSHRG
LYNAAKSAIVTLTYKAAADSVYGDTLERNMYVCCHVPLNAARFHNIRGRFKAAFVVY
RDSIPKNASLQDIEITCVKAVYDFAFRDLCIKYMLDLQPETVNAAAGTLGIVCPVNS
VICFVNSKNATLEKLTNTGLYNAGLYYVHEGIRTYFVQGPGPGFLNTVAIPDSVQIL
VGPGPGQRFHNIRGRWTGRCMGPGPGTNTGLYNLLIRCLRCQGPGPGIEFITFLGAL
KSFLKGPGPGPEWIQRQTVLQHSFNGPGPGLFVVYRDSIPHAACHKGPGPGIRTLED
LLMGTLGIVGPGPGLDLQPETTDLYCYEQGPGPGLQAIELQLTLETIYNGPGPGFQQ
LFLNTLSFVCPWGPGPGWKHMRLECAIYYKARGPGPGLCTELQTTIHDIILEGPGPG
FKTLIQPFILYAHIQGPGPGLYWYKTGISNISEVYGPGPGEVFEFAFKDLFVVYRGP
GPGHKAIELQMALQGLAQGPGPGAKFVAAWTLKAAA
(SEQ ID NO 127)

B. ICCG6149 DNA sequence

ATGGGCATGCAGGTGCAGATCCAGAGCCTGTTCCTGCTGCTGCTGTGGGTGCCCGGC
AGCCGGGGCAAGAGCCTGTTTGGCATGAGCCTGATGAAGAACAGCACCGCCGCTGCC
CTCTATTGGTACAAAAAGGCCGCCTGCTACAGCCTGTACGGCACCACCTTCAAGGCT
GCTGCCGTGGCCTGGGACAGCGTGTACTACATGAAGAGCACCGACCTGCGGGACCAC
ATCGACTACAACATCAGCGACTACCGGCACTACTGCTACAAGGCCGCCCAGGTGGTG
CCCGCCTACAACATCTCCAAGAACGGCTACAACACCTTCTACATCGAGTTCAAGCTC
CAGGACAAGATCATCGACCACTACAAAGCCGCCTGCCTGTACCTGCACATCCAGAGT
CTGAACGCAGCCGCTGCAACCCTCCAGGACATCGTGCTGCACGGCACCGTGTACGTG
TTCTGCTTCCTGCTGAACGCCATCCTGTACGCCCACATCCAGTGTCTGAATGCCGCC
CTGTACAACCTGCTGATCCGGTGCTTTAAGGCCGCCTTCGTGTACATCCCCCTGTTT
CTGATCAACACCGTGAGCGCCACCCAGCTGGTGAAGAATGGCACCGGCTGCAACGGC
TGGTTCTACAATGCCGCCACCAAGTACCCCCTGCTGAAGAACGTGTATGTGTTTTGT
TTTCTGCTGCCCATGAACGCCACACTGCACGACATTATCCTGGAATGCGTCAAGGCC
GCTGCCCTGTATGGCGTGAGCTTCAGCGAGCTGAAGCAGGTGGACTACTACGGCCTG
TACTACGGCGCCTACTACATGACCGACGCCGGCACCTGGAATGCCGCCCCCTTACGCC
GTGTGCGACAAGTGCTTCAAGCAGGGCGCCATGCTGGCCGTGTTCAAGAAAGCCGCT
GCCGTGGTGCTGCTGCTGGTGCGGTATAAGAATGCCGCCGCCAGCTACTTCGGCATG
AGCTTCATCCACTTTAAAGCCGCCAAGCTGCTGTCTAAGCTGCTGTGCGTGAATGCC
GCTGCTGCCACAATGTGCCGGCACTACAAGAGAAATGCCGCTGCCAGCACCGTGAGC
GTGGGCACCGCCAAGAACGCCGCCCTGAGCCAGATGGTGCAGTGGGCCTACAAGCTG
ACCAACACCGGCCTGTACAACGTGAACGCCGCTGCCACCTGCGTGAGCCACCGGGGC
CTGTATAACGCCGCCAAGAGCGCCATCGTGACCCTGACCTATAAGGCCGCTGCCGAC
AGCGTGTACGGCGACACCCTGGAACGGAACATGTACGTGTGCTGCCACGTGCCCCTG
AATGCCGCCAGGTTCCACAACATCCGGGGCAGGTTCAAAGCCGCCTTTGTGGTGTAC

CGGGACAGCATCCCCAAGAATGCCAGCCTCCAGGATATTGAGATCACCTGTGTGAAG
GCCGTGTACGACTTCGCCTTCCGGGACCTGTGCATCAAGTACATGCTGGACCTCCAG
CCCGAGACAGTGAACGCCGCCGCTGGCACACTGGGCATCGTGTGCCCCGTGAACAGC
GTGATCTGCTTCGTGAACAGCAAAAACGCCACCCTGGAAAAGCTGACAAATACAGGG
CTGTACAATGCCGGCCTGTATTACGTGCACGAGGGCATCCGGACCTACTTCGTGCAG
GGCCCAGGGCCAGGCTTCCTGAACACCGTGGCCATCCCCGACTCCGTGCAGATCCTG
GTCGGCCCAGGACCAGGGCAGCGGTTCCACAATATCAGAGGCCGGTGGACCGGCAGA
TGCATGGGCCCAGGACCTGGCACAAATACCGGACTGTATAATCTGCTGATTCGCTGC
CTGCGGTGCCAGGGTCCAGGACCAGGCATCGAGTTTATCACCTTTCTGGGCGCCCTG
AAGAGCTTCCTGAAAGGACCTGGACCAGGACCCGAGTGGATTCAGCGGCAGACCGTG
CTCCAGCACAGCTTCAACGGACCCGGACCCGGCCTGTTCGTGGTGTACAGAGACTCC
ATCCCCCACGCCGCCTGTCACAAGGGACCTGGACCAGGCATCAGGACCCTGGAGGAC
CTGCTGATGGGCACCCTGGGCATTGTGGGGCCTGGACCTGGACTGGATCTCCAGCCT
GAAACCACCGACCTGTACTGCTACGAGCAGGGGCCAGGACCTGGGCTCCAGGCTATC
GAACTCCAGCTGACCCTGGAAACCATCTACAATGGCCCCGGACCAGGCTTCCAGCAG
CTGTTCCTGAATACCCTGAGCTTCGTGTGCCCTTGGGGACCAGGGCCCGGATGGAAG
CACATGCGGCTGGAATGCGCCATCTACTACAAGGCCAGAGGCCCAGGACCCGGACTG
TGCACCGAACTCCAGACCACCATCCACGACATCATTCTGGAAGGACCAGGGCCAGGC
TTTAAGACCCTGATCCAGCCCTTCATTCTGTATGCCCACATTCAGGGACCTGGGCCT
GGCCTGTATTGGTATAAGACCGGCATCAGCAACATCTCCGAGGTGTACGGGCCTGGA
CCAGGCGAGGTGTTCGAGTTCGCCTTCAAGGATCTGTTTGTGGTGTATAGAGGCCCC
GGACCTGGCCACAAGGCCATTGAACTCCAGATGGCCCTCCAGGGGCTGGCCCAGGGA
CCAGGCCCTGGCGCCAAGTTCGTGGCCGCCTGGACCCTGAAAGCCGCCGCC<u>TGA</u>
(SEQ ID NO 128)

C.

KSLFGMSLMKNSTAAALYWYKKAACYSLYGTTFKAAAVAWDSVYYMKSTDLRDHIDY
NISDYRHYCYKAAQVVPAYNISKNGYNTFYIEFKLQDKIIDHYKAACLYLHIQSLNA
AAATLQDIVLHGTVYVFCFLLNAILYAHIQCLNAALYNLLIRCFKAAFVYIPLFLIN
TVSATQLVKNGTGCNGWFYNAATKYPLLKNVYVFCFLLPMNATLHDIILECVKAAAL
YGVSFSELKQVDYYGLYYGAYYMTDAGTWNAAPYAVCDKCFKQGAMLAVFKKAAAVV
LLLVRYKNAAASYFGMSFIHFKAAKLLSKLLCVNAAAATMCRHYKRNAAASTVSVGT
AKNAALSQMVQWAYKLTNTGLYNVNAAATCVSHRGLYNAAKSAIVTLTYKAAADSVY
GDTLERNMYVCCHVPLNAARFHNIRGRFKAAFVVYRDSIPKNASLQDIEITCVKAVY
DFAFRDLCIKYMLDLQPETVNAAAGTLGIVCPVNSVICFVNSKNATLEKLTNTGLYN
AGLYYVHEGIRTYFVQGPGPGFLNTVAIPDSVQILVGPGPGQRFHNIRGRWTGRCMG
PGPGTNTGLYNLLIRCLRCQGPGPGIEFITFLGALKSFLKGPGPGPEWIQRQTVLQH
SFNGPGPGLFVVYRDSIPHAACHKGPGPGIRTLEDLLMGTLGIVGPGPGLDLQPETT
DLYCYEQGPGPGLQAIELQLTLETIYNGPGPGFQQLFLNTLSFVCPWGPGPGWKHMR
LECAIYYKARGPGPGLCTELQTTIHDIILEGPGPGFKTLIQPFILYAHIQGPGPGLY
WYKTGISNISEVYGPGPGEVFEFAFKDLFVVYRGPGPGHKAIELQMALQGLAQGPGP
GAKFVAAWTLKAAA
(SEQ ID NO 160)

D.

```
AAGAGCCTGTTTGGCATGAGCCTGATGAAGAACAGCACCGCCGCTGCCCTCTATTGG
TACAAAAAGGCCGCCTGCTACAGCCTGTACGGCACCACCTTCAAGGCTGCTGCCGTG
GCCTGGGACAGCGTGTACTACATGAAGAGCACCGACCTGCGGGACCACATCGACTAC
AACATCAGCGACTACCGGCACTACTGCTACAAGGCCGCCCAGGTGGTGCCCGCCTAC
AACATCTCCAAGAACGGCTACAACACCTTCTACATCGAGTTCAAGCTCCAGGACAAG
ATCATCGACCACTACAAAGCCGCCTGCCTGTACCTGCACATCCAGAGTCTGAACGCA
GCCGCTGCAACCCTCCAGGACATCGTGCTGCACGGCACCGTGTACGTGTTCTGCTTC
CTGCTGAACGCCATCCTGTACGCCCACATCCAGTGTCTGAATGCCGCCCTGTACAAC
CTGCTGATCCGGTGCTTTAAGGCCGCCTTCGTGTACATCCCCCTGTTTCTGATCAAC
ACCGTGAGCGCCACCCAGCTGGTGAAGAATGGCACCGGCTGCAACGGCTGGTTCTAC
AATGCCGCCACCAAGTACCCCCTGCTGAAGAACGTGTATGTGTTTTGTTTTCTGCTG
CCCATGAACGCCACACTGCACGACATTATCCTGGAATGCGTCAAGGCCGCTGCCCTG
TATGGCGTGAGCTTCAGCGAGCTGAAGCAGGTGGACTACTACGGCCTGTACTACGGC
GCCTACTACATGACCGACGCCGGCACCTGGAATGCCGCCCCTTACGCCGTGTGCGAC
AAGTGCTTCAAGCAGGGCGCCATGCTGGCCGTGTTCAAGAAAGCCGCTGCCGTGGTG
CTGCTGCTGGTGCGGTATAAGAATGCCGCCGCCAGCTACTTCGGCATGAGCTTCATC
CACTTTAAAGCCGCCAAGCTGCTGTCTAAGCTGCTGTGCGTGAATGCCGCTGCTGCC
ACAATGTGCCGGCACTACAAGAGAAATGCCGCTGCCAGCACCGTGAGCGTGGGCACC
GCCAAGAACGCCGCCCTGAGCCAGATGGTGCAGTGGGCCTACAAGCTGACCAACACC
GGCCTGTACAACGTGAACGCCGCTGCCACCTGCGTGAGCCACCGGGGCCTGTATAAC
GCCGCCAAGAGCGCCATCGTGACCCTGACCTATAAGGCCGCTGCCGACAGCGTGTAC
GGCGACACCCTGGAACGGAACATGTACGTGTGCTGCCACGTGCCCCTGAATGCCGCC
AGGTTCCACAACATCCGGGGCAGGTTCAAAGCCGCCTTTGTGGTGTACCGGGACAGC
ATCCCCAAGAATGCCAGCCTCCAGGATATTGAGATCACCTGTGTGAAGGCCGTGTAC
GACTTCGCCTTCCGGGACCTGTGCATCAAGTACATGCTGGACCTCCAGCCCGAGACA
GTGAACGCCGCCGCTGGCACACTGGGCATCGTGTGCCCCGTGAACAGCGTGATCTGC
TTCGTGAACAGCAAAAACGCCACCCTGGAAAAGCTGACAAATACAGGGCTGTACAAT
GCCGGCCTGTATTACGTGCACGAGGGCATCCGGACCTACTTCGTGCAGGGCCCAGGG
CCAGGCTTCCTGAACACCGTGGCCATCCCCGACTCCGTGCAGATCCTGGTCGGCCCA
GGACCAGGGCAGCGGTTCCACAATATCAGAGGCCGGTGGACCGGCAGATGCATGGGC
CCAGGACCTGGCACAAATACCGGACTGTATAATCTGCTGATTCGCTGCCTGCGGTGC
CAGGGTCCAGGACCAGGCATCGAGTTTATCACCTTTCTGGGCGCCCTGAAGAGCTTC
CTGAAAGGACCTGGACCAGGACCCGAGTGGATTCAGCGGCAGACCGTGCTCCAGCAC
AGCTTCAACGGACCCGGACCCGGCCTGTTCGTGGTGTACAGAGACTCCATCCCCCAC
GCCGCCTGTCACAAGGGACCTGGACCAGGCATCAGGACCCTGGAGGACCTGCTGATG
GGCACCCTGGGCATTGTGGGGCCTGGACCTGGACTGGATCTCCAGCCTGAAACCACC
GACCTGTACTGCTACGAGCAGGGGCCAGGACCTGGGCTCCAGGCTATCGAACTCCAG
CTGACCCTGGAAACCATCTACAATGGCCCCGGACCAGGCTTCCAGCAGCTGTTCCTG
AATACCCTGAGCTTCGTGTGCCCTTGGGGACCAGGGCCCGGATGGAAGCACATGCGG
CTGGAATGCGCCATCTACTACAAGGCCAGAGGCCCAGGACCCGGACTGTGCACCGAA
CTCCAGACCACCATCCACGACATCATTCTGGAAGGACCAGGGCCAGGCTTTAAGACC
CTGATCCAGCCCTTCATTCTGTATGCCCACATTCAGGGACCTGGGCCTGGCCTGTAT
TGGTATAAGACCGGCATCAGCAACATCTCCGAGGTGTACGGGCCTGGACCAGGCGAG
GTGTTCGAGTTCGCCTTCAAGGATCTGTTTGTGGTGTATAGAGGCCCCGGACCTGGC
CACAAGGCCATTGAACTCCAGATGGCCCTCCAGGGGCTGGCCCAGGGACCAGGCCCT
GGCGCCAAGTTCGTGGCCGCCTGGACCCTGAAAGCCGCCGCC
```
(SEQ ID NO 161)

FIGURE 7 cont.2

FIGURE 8

A. ICCG6150 Amino acid sequence

MGMQVQIQSLFLLLLWVPGSRGATCVSHRGLYNAASTDLRDHIDYNAAAATMCRHYK
RNAILYAHIQCLNAAAGTLGIVCPVNAAACYSLYGTTFKAAADSVYGDTLERNQVVP
AYNISKNAALYNLLIRCFKAAFVYIPLFLINYYMTDAGTWGAVVLLLVRYKNAAISD
YRHYCYKAATVSATQLVKKASTAAALYWYKKAAFVVYRDSIPKNASYFGMSFIHFKA
AYMLDLQPETVNAAVYDFAFRDLCIKAALQDKIIDHYKAATLHDIILECVKKLTNTG
LYNVGAAASVICFVNSKGAAAMYVCCHVPLNASLQDIEITCVKCLYLHIQSLNAATK
YPLLKNVYVFCFLLPMNAKQGAMLAVFKKAALSQMVQWAYKAAPYAVCDKCFKAATV
YVFCFLLNAAAATLQDIVLHGAKSLFGMSLMKNGTGCNGWFYNARFHNIRGRFKAAK
LLSKLLCVNAAASTVSVGTAKNVAWDSVYYMKAAAGYNTFYIEFKAAALYGVSFSEL
KQVDYYGLYYNAAKSAIVTLTYKAAATLEKLTNTGLYNAGLYYVHEGIRTYFVQGPG
PGFLNTVAIPDSVQILVGPGPGQRFHNIRGRWTGRCMGPGPGTNTGLYNLLIRCLRC
QGPGPGIEFITFLGALKSFLKGPGPGPEWIQRQTVLQHSFNGPGPGLFVVYRDSIPH
AACHKGPGPGIRTLEDLLMGTLGIVGPGPGLDLQPETTDLYCYEQGPGPGLQAIELQ
LTLETIYNGPGPGFQQLFLNTLSFVCPWGPGPGWKHMRLECAIYYKARGPGPGLCTE
LQTTIHDIILEGPGPGFKTLIQPFILYAHIQGPGPGLYWYKTGISNISEVYGPGPGE
VFEFAFKDLFVVYRGPGPGHKAIELQMALQGLAQGPGPGAKFVAAWTLKAAA
(SEQ ID NO 129)

B. ICCG6150 DNA sequence

ATGGGCATGCAGGTGCAGATCCAGAGCCTGTTCCTGCTGCTGCTGTGGGTGCCCGGC
AGCAGAGGCGCCACCTGCGTGAGCCACAGGGGCCTCTACAACGCCGCCAGCACCGAC
CTGCGGGACCACATCGACTACAATGCTGCTGCCGCTACAATGTGCCGGCACTACAAG
CGGAACGCCATCCTGTACGCCCACATCCAGTGCCTGAATGCTGCCGCTGGCACACTG
GGCATCGTGTGCCCCGTGAATGCCGCCGCCTGCTACAGCCTGTACGGCACCACCTTC
AAGGCCGCTGCCGACTCCGTGTACGGCGACACCCTGGAACGGAACCAGGTGGTGCCC
GCCTACAACATCTCTAAGAATGCCGCTCTGTACAACCTGCTGATCCGGTGCTTTAAG
GCTGCCTTCGTGTACATCCCCCTGTTTCTGATCAACTACTACATGACCGACGCCGGC
ACATGGGGAGCCGTGGTGCTGCTGCTGGTGCGGTACAAGAATGCCGCCATCAGCGAC
TACCGGCACTACTGCTACAAGGCCGCCACCGTCAGCGCCACCCAGCTGGTGAAGAAG
GCCAGCACAGCCGCCGCTCTCTATTGGTATAAAAAAGCCGCCTTTGTGGTGTACCGG
GACAGCATCCCCAAGAACGCCAGCTACTTCGGCATGAGCTTCATCCACTTCAAAGCC
GCCTACATGCTGGACCTCCAGCCCGAGACCGTGAACGCTGCCGTGTACGACTTCGCC
TTCCGGGACCTGTGCATTAAAGCCGCACTCCAGGACAAGATCATCGACCATTATAAA
GCAGCCACCCTGCATGATATTATTCTGGAATGCGTGAAGAAGCTGACCAACACCGGC
CTCTATAACGTGGGAGCCGCCGCCTCTGTGATCTGCTTCGTGAACAGCAAGGGGGCT
GCCGCCATGTATGTGTGCTGCCACGTGCCCCTGAACGCCTCTCTCCAGGATATTGAG
ATCACCTGTGTGAAGTGCCTGTACCTGCACATTCAGTCTCTGAATGCCGCCACCAAG
TACCCCCTGCTGAAGAACGTGTATGTCTTTTGCTTCCTGCTGCCCATGAACGCCAAG
CAGGGCGCCATGCTGGCCGTGTTCAAAAAGGCCGCCCTGAGCCAGATGGTGCAGTGG
GCCTACAAAGCCGCCCCTTACGCCGTGTGCGACAAGTGTTTTAAGGCCGCCACAGTG
TACGTGTTTTGTTTTCTGCTGAATGCCGCTGCCGCCACCCTCCAGGACATCGTGCTG
CACGGCGCCAAGTCCCTGTTCGGCATGTCCCTGATGAAGAATGGCACCGGCTGCAAC
GGCTGGTTCTACAACGCCCGGTTCCACAACATCCGGGGCAGGTTTAAAGCCGCCAAG

```
CTGCTGTCTAAGCTGCTGTGTGTGAACGCCGCCGCTTCCACCGTGAGCGTGGGCACC
GCCAAGAACGTGGCCTGGGACAGCGTGTACTACATGAAAGCAGCAGCCGGGTACAAC
ACCTTCTACATCGAGTTTAAAGCTGCCGCCCTGTACGGCGTGAGCTTCAGCGAGCTG
AAGCAGGTGGACTACTACGGCCTGTACTATAACGCCGCCAAGAGCGCCATCGTGACC
CTGACCTATAAAGCCGCCGCCACACTGGAAAAGCTGACCAATACAGGGCTGTACAAT
GCCGGCCTGTATTACGTGCACGAGGGCATCCGGACCTACTTCGTGCAGGGCCCAGGG
CCAGGCTTCCTGAACACCGTGGCCATCCCCGACTCCGTGCAGATCCTGGTCGGCCCA
GGACCAGGGCAGCGGTTCCACAATATCAGAGGCCGGTGGACCGGCAGATGCATGGGC
CCAGGACCTGGCACAAATACCGGACTGTATAATCTGCTGATTCGCTGCCTGCGGTGC
CAGGGTCCAGGACCAGGCATCGAGTTTATCACCTTTCTGGGCGCCCTGAAGAGCTTC
CTGAAAGGACCTGGACCAGGACCCGAGTGGATTCAGCGGCAGACCGTGCTCCAGCAC
AGCTTCAACGGACCCGGACCCGGCCTGTTCGTGGTGTACAGAGACTCCATCCCCCAC
GCCGCCTGTCACAAGGGACCTGGACCAGGCATCAGGACCCTGGAGGACCTGCTGATG
GGCACCCTGGGCATTGTGGGGCCTGGACCTGGACTGGATCTCCAGCCTGAAACCACC
GACCTGTACTGCTACGAGCAGGGGCCAGGACCTGGGCTCCAGGCTATCGAACTCCAG
CTGACCCTGGAAACCATCTACAATGGCCCCGGACCAGGCTTCCAGCAGCTGTTCCTG
AATACCCTGAGCTTCGTGTGCCCTTGGGGACCAGGGCCCGGATGGAAGCACATGCGG
CTGGAATGCGCCATCTACTACAAGGCCAGAGGCCCAGGACCCGGACTGTGCACCGAA
CTCCAGACCACCATCCACGACATCATTCTGGAAGGACCAGGGCCAGGCTTTAAGACC
CTGATCCAGCCCTTCATTCTGTATGCCCACATTCAGGGACCTGGGCCTGGCCTGTAT
TGGTATAAGACCGGCATCAGCAACATCTCCGAGGTGTACGGGCCTGGACCAGGCGAG
GTGTTCGAGTTCGCCTTCAAGGATCTGTTTGTGGTGTATAGAGGCCCCGGACCTGGC
CACAAGGCCATTGAACTCCAGATGGCCCTCCAGGGGCTGGCCCAGGGACCAGGCCCT
GGCGCCAAGTTCGTGGCCGCCTGGACCCTGAAAGCCGCCGCCTGA
```
(SEQ ID NO 130)

C.

```
ATCVSHRGLYNAASTDLRDHIDYNAAAATMCRHYKRNAILYAHIQCLNAAAGTLGIV
CPVNAAACYSLYGTTFKAAADSVYGDTLERNQVVPAYNISKNAALYNLLIRCFKAAF
VYIPLFLINYYMTDAGTWGAVVLLLVRYKNAAISDYRHYCYKAATVSATQLVKKAST
AAALYWYKKAAFVVYRDSIPKNASYFGMSFIHFKAAYMLDLQPETVNAAVYDFAFRD
LCIKAALQDKIIDHYKAATLHDIILECVKKLTNTGLYNVGAAASVICFVNSKGAAAM
YVCCHVPLNASLQDIEITCVKCLYLHIQSLNAATKYPLLKNVYVFCFLLPMNAKQGA
MLAVFKKAALSQMVQWAYKAAPYAVCDKCFKAATVYVFCFLLNAAAATLQDIVLHGA
KSLFGMSLMKNGTGCNGWFYNARFHNIRGRFKAAKLLSKLLCVNAAASTVSVGTAKN
VAWDSVYYMKAAAGYNTFYIEFKAAALYGVSFSELKQVDYYGLYYNAAKSAIVTLTY
KAAATLEKLTNTGLYNAGLYYVHEGIRTYFVQGPGPGFLNTVAIPDSVQILVGPGPG
QRFHNIRGRWTGRCMGPGPGTNTGLYNLLIRCLRCQGPGPGIEFITFLGALKSFLKG
PGPGPEWIQRQTVLQHSFNGPGPGLFVVYRDSIPHAACHKGPGPGIRTLEDLLMGTL
GIVGPGPGLDLQPETTDLYCYEQGPGPGLQAIELQLTLETIYNGPGPGFQQLFLNTL
SFVCPWGPGPGWKHMRLECAIYYKARGPGPGLCTELQTTIHDIILEGPGPGFKTLIQ
PFILYAHIQGPGPGLYWYKTGISNISEVYGPGPGEVFEFAFKDLFVVYRGPGPGHKA
IELQMALQGLAQGPGPGAKFVAAWTLKAAA
```
(SEQ ID NO 162)

FIGURE 8 cont.1

D.

```
GCCACCTGCGTGAGCCACAGGGGCCTCTACAACGCCGCCAGCACCGACCTGCGGGAC
CACATCGACTACAATGCTGCTGCCGCTACAATGTGCCGGCACTACAAGCGGAACGCC
ATCCTGTACGCCCACATCCAGTGCCTGAATGCTGCCGCTGGCACACTGGGCATCGTG
TGCCCCGTGAATGCCGCCGCCTGCTACAGCCTGTACGGCACCACCTTCAAGGCCGCT
GCCGACTCCGTGTACGGCGACACCCTGGAACGGAACCAGGTGGTGCCCGCCTACAAC
ATCTCTAAGAATGCCGCTCTGTACAACCTGCTGATCCGGTGCTTTAAGGCTGCCTTC
GTGTACATCCCCCTGTTTCTGATCAACTACTACATGACCGACGCCGGCACATGGGGA
GCCGTGGTGCTGCTGCTGGTGCGGTACAAGAATGCCGCCATCAGCGACTACCGGCAC
TACTGCTACAAGGCCGCCACCGTCAGCGCCACCCAGCTGGTGAAGAAGGCCAGCACA
GCCGCCGCTCTCTATTGGTATAAAAAAGCCGCCTTTGTGGTGTACCGGGACAGCATC
CCCAAGAACGCCAGCTACTTCGGCATGAGCTTCATCCACTTCAAAGCCGCCTACATG
CTGGACCTCCAGCCCGAGACCGTGAACGCTGCCGTGTACGACTTCGCCTTCCGGGAC
CTGTGCATTAAAGCCGCACTCCAGGACAAGATCATCGACCATTATAAAGCAGCCACC
CTGCATGATATTATTCTGGAATGCGTGAAGAAGCTGACCAACACCGGCCTCTATAAC
GTGGGAGCCGCCGCCTCTGTGATCTGCTTCGTGAACAGCAAGGGGGCTGCCGCCATG
TATGTGTGCTGCCACGTGCCCCTGAACGCCTCTCTCCAGGATATTGAGATCACCTGT
GTGAAGTGCCTGTACCTGCACATTCAGTCTCTGAATGCCGCCACCAAGTACCCCCTG
CTGAAGAACGTGTATGTCTTTTGCTTCCTGCTGCCCATGAACGCCAAGCAGGGCGCC
ATGCTGGCCGTGTTCAAAAAGGCCGCCCTGAGCCAGATGGTGCAGTGGGCCTACAAA
GCCGCCCCTTACGCCGTGTGCGACAAGTGTTTTAAGGCCGCCACAGTGTACGTGTTT
TGTTTTCTGCTGAATGCCGCTGCCGCCACCCTCCAGGACATCGTGCTGCACGGCGCC
AAGTCCCTGTTCGGCATGTCCCTGATGAAGAATGGCACCGGCTGCAACGGCTGGTTC
TACAACGCCCGGTTCCACAACATCCGGGGCAGGTTTAAAGCCGCCAAGCTGCTGTCT
AAGCTGCTGTGTGTGAACGCCGCCGCTTCCACCGTGAGCGTGGGCACCGCCAAGAAC
GTGGCCTGGGACAGCGTGTACTACATGAAAGCAGCAGCCGGGTACAACACCTTCTAC
ATCGAGTTTAAAGCTGCCGCCCTGTACGGCGTGAGCTTCAGCGAGCTGAAGCAGGTG
GACTACTACGGCCTGTACTATAACGCCGCCAAGAGCGCCATCGTGACCCTGACCTAT
AAAGCCGCCGCCACACTGGAAAAGCTGACCAATACAGGGCTGTACAATGCCGGCCTG
TATTACGTGCACGAGGGCATCCGGACCTACTTCGTGCAGGGCCCAGGGCCAGGCTTC
CTGAACACCGTGGCCATCCCCGACTCCGTGCAGATCCTGGTCGGCCCAGGACCAGGG
CAGCGGTTCCACAATATCAGAGGCCGGTGGACCGGCAGATGCATGGGCCCAGGACCT
GGCACAAATACCGGACTGTATAATCTGCTGATTCGCTGCCTGCGGTGCCAGGGTCCA
GGACCAGGCATCGAGTTTATCACCTTTCTGGGCGCCCTGAAGAGCTTCCTGAAAGGA
CCTGGACCAGGACCCGAGTGGATTCAGCGGCAGACCGTGCTCCAGCACAGCTTCAAC
GGACCCGGACCCGGCCTGTTCGTGGTGTACAGAGACTCCATCCCCCACGCCGCCTGT
CACAAGGGACCTGGACCAGGCATCAGGACCCTGGAGGACCTGCTGATGGGCACCCTG
GGCATTGTGGGGCCTGGACCTGGACTGGATCTCCAGCCTGAAACCACCGACCTGTAC
TGCTACGAGCAGGGGCCAGGACCTGGGCTCCAGGCTATCGAACTCCAGCTGACCCTG
GAAACCATCTACAATGGCCCCGGACCAGGCTTCCAGCAGCTGTTCCTGAATACCCTG
AGCTTCGTGTGCCCTTGGGGACCAGGGCCCGGATGGAAGCACATGCGGCTGGAATGC
GCCATCTACTACAAGGCCAGAGGCCCAGGACCCGGACTGTGCACCGAACTCCAGACC
ACCATCCACGACATCATTCTGGAAGGACCAGGGCCAGGCTTTAAGACCCTGATCCAG
CCCTTCATTCTGTATGCCCACATTCAGGGACCTGGGCCTGGCCTGTATTGGTATAAG
ACCGGCATCAGCAACATCTCCGAGGTGTACGGGCCTGGACCAGGCGAGGTGTTCGAG
TTCGCCTTCAAGGATCTGTTTGTGGTGTATAGAGGCCCCGGACCTGGCCACAAGGCC
ATTGAACTCCAGATGGCCCTCCAGGGGCTGGCCCAGGGACCAGGCCCTGGCGCCAAG
TTCGTGGCCGCCTGGACCCTGAAAGCCGCCGCC
```
(SEQ ID NO 163)

FIGURE 8 cont.2

HPV POLYEPITOPE CONSTRUCTS AND USES THEREOF

This application is the U.S. national phase of International Application No. PCT/EP2008/056586, filed 29 May 2008, which designated the U.S. and claims priority to Europe Application No. 07110056.4, filed 12 Jun. 2007; and claims the benefit of U.S. Provisional Application No. 60/924,778, filed 31 May 2007, the entire contents of each of which are hereby incorporated by reference.

FIELD OF THE INVENTION

The present invention is directed to Human Papillomavirus (HPV) polyepitope constructs and the use thereof for the prevention and/or treatment of HPV infection.

BACKGROUND OF THE INVENTION

Cancer of the cervix uteri is the second most common cancer among women worldwide, with an estimated 493,000 new cases and 274,000 deaths in 2002. The field of cervical cancer prevention is rapidly evolving as a consequence of the identification of the cause of the disease: a limited number of viral types from the family of the Human Papillomaviruses (HPV). Indeed, HPV has been recognized as a cause of cervical cancer, and 2 of the oncogenic types, 16 and 18, are together responsible for 70% of the world's cervical cancer cases.

Recently the use of 2 prophylactic vaccines was licensed. Nevertheless, it is likely to be decades before the impact of HPV vaccination on the incidence of cervical cancer can be evaluated. Optimally, these vaccines should be administered before sexual debut and HPV infection. As such, they are of no benefit for women with already existing HPV infection. Treatment (surgery) for HPV infection is often unsatisfactory because of persistence of virus after treatment and recurrence of clinically apparent disease is common. The treatment may require frequent visits to clinics and is not directed at elimination of the virus but at clearing warts. Moreover, it is expected that less prevalent, oncogenic HPV genotypes will take over—at least in part—the place from the currently targeted HPV16 and 18 genotypes. Women with pre-carcinogenic lesions resulting from the widespread HPV infections today represent a highly unmet need.

Thus, a need exists for an efficacious vaccine to prevent and/or treat persistent HPV infection and to prevent cancer that is associated with HPV infection. Effective HPV vaccines would be a significant advance in the control of sexually transmissible infections and could also protect against clinical disease, particularly cancers such as cervical cancer. (see, e.g., Rowen, P. and Lacey, C., Dermatologic Clinics 16 (4): 835-838, 1998).

In the majority of individuals, HPV infections presumably induce strong, local, cell-mediated immunity that results in clearance of the virus and protection against subsequent infection. Virus-specific, human leukocyte antigen (HLA) class I-restricted cytotoxic T lymphocytes (CTL) and HLA class II-restricted helper T lymphocytes (HTL) are known to play a major role in the prevention of chronic infection and in viral clearance in vivo (Houssaint et al., 2001; Gruters et al., 2002; Tsai et al., 1997; Murray et al., 1992; Tigges et al., 1992; Bowen and Walker, 2005).

A therapeutic vaccine candidate targeting HPV should elicit strong and multi-specific cellular immune responses. The induction of a strong HPV-specific cellular response—comprising activity of cytotoxic T-cells (CTL) and helper T-cells (HTL)—may be achieved using an epitope-based vaccine approach.

The polyepitope approach to vaccine development is to rationally create a multi-specific cellular response, causing the immune system to be specifically stimulated against multiple selected epitopes that meet stringent criteria. These include CTL epitopes that are presented by MHC-I and are recognized by cytotoxic T-cells, and HTL epitopes that bind MHC II and are recognized by helper T-cells. The epitopes are selected in view of their capacity to elicit responses in humans, thereby aiming for a large population coverage (by targeting major HLA class-I alleles as well as major HLA class-II alleles).

The technology relevant to polyepitope vaccines is developing and a number of different approaches are available which allow simultaneous delivery of multiple epitopes. Several independent studies have established that induction of simultaneous immune responses against multiple and individual peptides can be achieved (Doolan et al (1997), Bertoni and colleagues (1997)). In terms of immunization with polyepitope nucleic acid vaccines, several examples have been reported where multiple T cell responses were induced (Thomson et al., 1995; Woodberry et al., 1999; Mateo et al., 1999; Ishioka et al., 1999; WO04/031210, Innogenetics N. V. et al.).

The efforts to develop an effective treatment for HPV-related disease are narrowly focused. Most studies are concentrating on the HPV type 16 E6 and/or E7 protein. Also WO05/089164 (Pharmexa et al.) discloses HPV polyepitope constructs focussing on E6 and E7, and additionally E1 and E2 proteins. During the papillomavirus life cycle, the HPV proteins (E1, E2, E4, E5, E6, E7, L1 and L2) are differentially expressed. Moreover, during progression from CIN1 to CIN3, the extent of expression of the different HPV proteins is changing (Doorbar, 2005). Targeting all 6 early proteins (E1, E2, E4, E5, E6 and E7) thus provides a way to induce efficient immune responses directed to all stages of the virus life cycle, irrespective of the CIN grade.

Although E4 and E5 were screened for immunogenic epitopes, WO05/089164 was unsuccessful in obtaining reactive peptides. It is indeed known that most of the HPV proteins are comparatively small and might therefore not comprise many reactive epitopes.

The present inventors however have now determined several immunogenic epitopes in the E4 and E5 proteins of the high risk HPV genotypes HPV16, 18, 31 and 45. Moreover, the present inventors were successful in creating a potent, multi-specific and full-spectrum vaccine addressing the different stages of HPV infection, and thereby broadening the treatment window. Where others, focusing on E6 and/or E7 are mainly targeting CIN2 and CIN3, this vaccine allows to treat earlier stages of disease as well as persistent infection, thereby further reducing the chance of developing cervical cancer.

The polyepitope constructs are designed to induce an immune response to at least 4 distinct CTL and 1-3 HTL epitopes per HPV genotype in the majority of subjects infected with one of the four most prevalent, high risk HPV genotypes (HPV16, 18, 31 and 45) irrespective of their ethnic origin.

SUMMARY OF THE INVENTION

The present invention encompasses epitopes derived from the E1, E2, E4, E5, E6 and/or E7 protein of the Human Papillomavirus (HPV). Each of the epitopes given in Tables 1 and 2, or any combination of two, more or all of these epitopes, are part of the invention, as well as their application in the treatment and/or prevention of HPV infection or HPV-related disease. The epitopes are those which elicit a HLA class I- and/or class II-restricted T lymphocyte response in an immunized host.

In a particular embodiment, the present invention relates to an isolated CTL inducing peptide derived from a Human Papillomavirus protein, consisting of 8 to 13 amino acids and comprising the sequence represented by SEQ ID NO 1-88. More specific, the invention encompasses an isolated CTL inducing peptide derived from the Human Papillomavirus protein E4 or E5, consisting of 8 to 13 amino acids and comprising the sequence represented by SEQ ID NO 8, 17, 29, 42, 43, 51, 64, 74, 75, 81 and 86.

The invention also covers an isolated polyepitope construct comprising one or more of the herein described CTL inducing peptides.

The present invention is furthermore directed to a polynucleotide, a polypeptide, a vector or a composition comprising a polyepitope construct encoding or comprising specifically selected epitopes derived of HPV.

In one embodiment, the polyepitope construct encodes or comprises at least the following HPV derived CTL epitopes: SEQ ID NO 1 to 44, and/or the polyepitope construct encodes or comprises at least the following HPV CTL epitopes: SEQ ID NO 1, 23, 39 and 45 to 88. In another embodiment, the current invention relates to a polynucleotide comprising a polyepitope construct comprising nucleic acids encoding all the epitopes given in Table 1 (SEQ ID NO 1-88). Specifically, the construct does not encode a full-length protein from HPV.

In a further embodiment, the polyepitope construct of the invention further encodes or comprises at least one CTL and/or HTL epitope. Preferably, the epitopes are isolated. In a specific embodiment, the at least one CTL and/or HTL epitope is derived from HPV. More specific, the at least one HTL epitope is selected from the group consisting of SEQ ID NO 89 to 121. Preferably, the polyepitope construct furthermore comprises a PADRE® epitope. Specifically, the PADRE® epitope is characterized by SEQ ID NO 122.

Optionally, the epitopes in the polyepitope construct are linked to each other by one or more, preferably 1 to 8, spacer amino acids. In a specific embodiment, the one or more spacer amino acids are selected from the group consisting of: K, R, N, Q, G, A, S, C, G, P, and T. More specifically, the spacer between one or more CTL epitopes is selected from the group consisting of G, K, A or N, and the spacer between one or more HTL epitopes is selected from the group consisting of G, N and P.

In a further embodiment, the CTL and/or HTL epitopes comprised in the polyepitope construct are sorted to minimize the number of CTL and/or HTL junctional epitopes.

Specifically, the HPV CTL epitopes are directly or indirectly linked in the order as shown in FIG. 1A, 2A, 3 or 4. The HPV HTL epitopes can be directly or indirectly linked in the order as shown in FIG. 1B or 2B.

Optionally, the polynucleotide of the present invention further comprises one or more regulatory sequences. Preferably, said regulatory sequence is an internal ribosome binding site (IRES).

In a specific embodiment, the polynucleotide of the present invention further comprises one or more promoters. Preferably, the promoter is a CMV promoter.

In a further embodiment, the polynucleotide of the present invention further comprises one or more signal sequences. Preferably, the signal sequence is a Igkappa signal sequence.

In another embodiment, the polynucleotide of the invention comprises one or more MHC class I and/or MHC class II-targeting sequences. Preferably, the targeting sequence is selected from the group consisting of tissue plasminogen activator signal sequence, insulin signal sequence, endoplasmic reticulum signal sequence, LAMP-1 lysosomal targeting sequence, LAMP-2 lysosomal targeting sequence, HLA-DM lysosomal targeting sequence, HLA-DM-association sequences of HLA-DO, Ig-alpha cytoplasmic domain, Ig-beta cytoplasmic domain, Ii protein, influenza matrix protein, HBV surface antigen, HBV core antigen, and yeast Ty protein.

In a specific embodiment, the polynucleotide of the present invention comprises a polyepitope construct encoding the amino acid sequence consisting of, comprised in or comprising the sequence represented by SEQ ID NO 123, SEQ ID NO 125, SEQ ID NO 127 or SEQ ID NO 129. In another embodiment the polyepitope construct is characterized by or comprised in the nucleic acid sequence represented by SEQ ID NO 124, SEQ ID NO 126, SEQ ID NO 128 or SEQ ID NO 130.

In a further embodiment, the polyepitope construct encodes the amino acid sequence consisting of or comprising the sequence represented by SEQ ID NO 156, SEQ ID NO 158, SEQ ID NO 160, or SEQ ID NO 162. In another embodiment, polyepitope construct consists of or comprises the nucleic acid sequence represented by SEQ ID NO 157, SEQ ID NO 159, SEQ ID NO 161, or SEQ ID NO 163.

Furthermore, the invention encompasses a vector comprising the polynucleotide as described herein. Preferably, the vector is an expression vector. More preferably, the vector is a plasmid (pDNA), a viral, a bacterial or a yeast vector. In a further embodiment, the viral vector is a pox virus. Preferably, the pox virus is a vaccinia virus. More preferably, the vaccinia virus is MVA.

Moreover, the current invention also relates to an isolated polypeptide encoded by the polynucleotide as described herein.

The current invention also relates to a composition comprising the polynucleotide, the polypeptide, or the vector as described herein, or any combination thereof.

Preferably, the composition further comprises a pharmaceutical acceptable excipient or carrier. In a specific embodiment, the composition is a vaccine.

In another embodiment, the present invention relates to the composition, the polynucleotide, the vector or the polypeptide as described herein, for use as a medicament.

Specifically, the invention includes the use of the composition, the polynucleotide, the vector or the polypeptide for the manufacture of a medicament for treating and/or preventing persistent HPV infection. The invention also encompasses the composition, the polynucleotide, the vector or the polypeptide for use in the treatment and/or prevention of persistent HPV infection. Specifically, the invention is directed to the treatment and/or prevention of HPV-related disease.

Moreover, the present invention includes a cell comprising the polynucleotide, the polypeptide, or the vector as described herein.

In a further embodiment, the invention relates to a method of inducing an immune response against HPV in an individual, comprising administering the polynucleotide, the polypeptide, the vector, the composition, or the cell as described herein, or a combination thereof, to said individual. Specifically, the method is directed to the treatment and/or prevention of HPV infection and/or HPV-related disease.

Furthermore, the invention covers a method of making the polynucleotide, the polypeptide, the vector, the composition, or the cell as described herein.

FIGURE LEGENDS

FIG. 1: A. Specific order of CTL epitopes in construct ICCG6150
B. Specific order of HTL epitopes in construct ICCG6150 or ICCG6149
FIG. 2: A. Specific order of CTL epitopes in construct ICCG6138
B. Specific order of HTL epitopes in construct ICCG6138 or ICCG6137
FIG. 3: Specific order of CTL epitopes in construct ICCG6137
FIG. 4: Specific order of CTL epitopes in construct ICCG6149
FIG. 5: Construct ICCG6137
  A. Amino acid sequence of the signal sequence (in italics) and the polyepitope;
  B. DNA sequence: The start and stop codons are underlined. The signal sequence is shown in italics, and the epitope-coding sequence is bolded.
  C. Amino acid sequence of the polyepitope;
  D. DNA sequence of the polyepitope.
FIG. 6: Construct ICCG6138
  A. Amino acid sequence of the signal sequence (in italics) and the polyepitope;
  B. DNA sequence: The start and stop codons are underlined. The signal sequence is shown in italics, and the epitope-coding sequence is bolded.
  C. Amino acid sequence of the polyepitope;
  D. DNA sequence of the polyepitope.
FIG. 7: Construct ICCG6149
  A. Amino acid sequence of the signal sequence (in italics) and the polyepitope;
  B. DNA sequence: The start and stop codons are underlined. The signal sequence is shown in italics, and the epitope-coding sequence is bolded.
  C. Amino acid sequence of the polyepitope;
  D. DNA sequence of the polyepitope.
FIG. 8: Construct ICCG6150
  A. Amino acid sequence of the signal sequence (in italics) and the polyepitope;
  B. DNA sequence: The start and stop codons are underlined. The signal sequence is shown in italics, and the epitope-coding sequence is bolded.
  C. Amino acid sequence of the polyepitope;
  D. DNA sequence of the polyepitope.
FIG. 9: HTL recall responses in HPV patients

DETAILED DESCRIPTION OF THE INVENTION

The present invention is directed to a polynucleotide or polypeptide comprising a polyepitope construct encoding or comprising epitopes derived from the E1, E2, E4, E5, E6 and/or E7 protein of the Human Papillomavirus (HPV). The epitopes are those which elicit a HLA class I- and/or class II-restricted T-lymphocyte response in an immunized host. More specifically, the present invention describes highly optimized and effective polyepitope constructs characterized by efficient processing and comprising highly immunogenic epitopes allowing efficient treatment of patients at different stages of HPV-related disease.

Identification of the Epitopes

CTL binding epitopes were evaluated for their immunogenicity in different HLA transgenic mice. To this, a single immunization with CTL peptide pools together with a common HTL epitope emulsified in IFA was performed and up to 14 days later, CD8+ spleen cells were isolated and evaluated for epitope specificity using a direct ex vivo IFNγ ELISPOT assay. The majority of high affinity binding CTL epitopes proved to be immunogenic.

HTL binding epitopes were evaluated for their induction of (ex vivo) recall T cell responses using PBMC from HPV patients. To this, PBMC from subjects were cultured in vitro for 1-2 weeks in the presence of test peptide plus antigen-presenting cells (APC to allow activation of "memory" T cells, as compared to "naive" T cells). At the end of the culture period, T cell activity was detected using assays such as $^{51}$Cr release involving peptide-loaded target cells, T cell proliferation, or cytokine release.

The CTL epitopes of the present invention are given in Table 1. Each individual epitope is part of the invention as well as combinations of two, more, or all of said epitopes. In a specific aspect of the invention, epitopes have been identified in the E4 and E5 proteins of the high risk HPV genotypes HPV 16, 18, 31 and 45, whereby said epitopes are being characterized by SEQ ID NO 8, 17, 29, 42, 43, 51, 52, 64, 74, 75, 81 and 86. As such, the present invention also relates to a combination comprising 2, 3, 4, 5, 6, 7, 8, 9, 10, 11 or all of the epitopes characterized by SEQ ID NO 8, 17, 29, 42, 43, 51, 52, 64, 74, 75, 81 and 86, optionally linked to each other in a polyepitope construct.

Starting from said pool of CTL epitopes, the present inventors were successful in creating a potent, multi-specific and full-spectrum vaccine addressing the different stages of HPV infection, and broadening the treatment window.

The polyepitope construct of the present invention is particularly useful to prevent and/or treat HPV infection, more specific HPV-related disease, and even more specific the precancerous stages of HPV infection, i.e. CIN 1-3. HPV-related disease includes neoplasia and HPV related cancers such as but not limited to cervical cancer and head and neck carcinoma. The neoplasia to be treated with the methods and medicaments according to the current invention may be any HPV induced neoplasia, preferably in an epithelial tissue, in the ano-genital area and/or ano-genital tract, comprising the vulva, vagina, cervix, penis, scrotum, anus and rectum. The neoplastic disorders to be treated comprise Cervial Intraepithelial Neoplasia of various grades (CIN 1, 2 and 3), Vulvar intraepithelial neoplasias of various grades (VIN 1, 2 and 3) and Vaginal intraepithelial neoplasias (VAIN) and anal intraepithelial neoplasia (AIN). Also male subjects suffering from virally induced neoplasias in the ano-genital area and/or tract, such as but not limited to, Penile intraepithelial neoplasia (PIN) and Anal intraepithelial neoplasia (AIN), may be treated according to this invention.

Although most HPV infections do not progress to cervical cancer, infections that persist for many years are more likely to do so. Most cervical cancers develop slowly through a series of abnormal changes in the cells of the cervix. Regular Pap tests can detect these changes and the abnormal tissue can be removed, preventing it from ever developing into cancer. Various terms have been used to describe the abnormal cells that may be seen in Pap tests. Samples with cell abnormalities may be divided into different categories.

Cervical intraepithelial neoplasia (CIN) is a term that is often used to describe abnormal tissue findings. Neoplasia means an abnormal growth of cells. The term CIN along with a number (1, 2, or 3) describes how much of the thickness of the lining of the cervix contains abnormal cells. CIN-3 is considered to be a precancerous condition that includes carcinoma in situ.

Another classification is:
  ASC—Atypical Squamous Cells. Squamous cells are the thin, flat cells that form the surface of the cervix.

AGC—Atypical Glandular Cells. Glandular cells are mucus-producing cells found in the endocervical canal (opening in the center of the cervix) or in the lining of the uterus. The glandular cells do not appear normal, but doctors are uncertain what the cell changes mean.

AIS—endocervical Adenocarcinoma In Situ. Precancerous cells are found in the glandular tissue.

LSIL—Low-grade Squamous Intraepithelial Lesion. Low-grade means there are early changes in the size and shape of the cells. The word lesion refers to an area of abnormal tissue. LSILs are considered mild abnormalities caused by HPV infection and are a common condition, especially among young women. The majority of LSILs return to normal over months to a few years.

HSIL—High-grade Squamous Intraepithelial Lesion. High-grade means that the cells look very different in size and shape from normal cells. HSILs are more severe abnormalities and may eventually lead to cancer if left untreated.

Pap test results may also be described using an older set of categories called the "dysplasia scale." Dysplasia is a term used to describe abnormal cells. Although dysplasia is not cancer, it may develop into very early cancer of the cervix. The cells look abnormal under the microscope, but they do not invade nearby healthy tissue. There are four degrees of dysplasia: mild, moderate, severe, and carcinoma in situ. Carcinoma in situ is a precancerous condition that involves only the layer of cells on the surface of the cervix, and has not spread to nearby tissues. Currently, mild dysplasia is classified as LSIL; moderate or severe dysplasia and carcinoma in situ are combined into HSIL.

Overview:

| LGSIL | HGSIL | | |
|---|---|---|---|
| CIN 1 | CIN 2 | | CIN 3 |
| Mild dysplasia | Moderate dysplasia | Severe dysplasia | Carcinoma in situ |

The polyepitope constructs are designed to induce an immune response to at least 4 distinct CTL and 1-3 HTL epitopes per HPV genotype in the majority of subjects infected with one of the four most prevalent, high risk HPV genotypes (HPV16, 18, 31 and 45) irrespective of their ethnic origin. The epitopes in the constructs were sorted and optimized using the method as described in WO04/031210 (Pharmexa Inc. et al.; incorporated herein by reference). Epitopes were included in one or more constructs. The constructs were subsequently tested in HLA transgenic mice and immunogenicity was measured for the encoded epitopes.

Evidently, the T cell epitopes as given in Tables 1 and/or 2 can be combined into one or more constructs in any manner appropriate for a specific therapeutic application or patient group. For example, only the HPV16 CTL and/or HTL epitopes of Tables 1 and/or 2 can be combined into 1 construct. Alternatively, the epitopes in the construct can be limited to HPV18, HPV31 or HPV45. A different approach is to combine the epitopes for the different HPV genotypes, but to limit to certain proteins, e.g. E1, E2, E4, E5, E6 or E7, or combinations of proteins, e.g. E1 and E2, or E4 and E5, or E6 and E7, or other combinations of T cell epitopes derived from 2 or more HPV proteins, this for one genotype, or alternatively for two, three or four of the herein described genotypes.

In one embodiment, the present invention relates to an isolated polynucleotide comprising a polyepitope construct encoding at least the following HPV derived cytotoxic T lymphocyte (CTL) epitopes: SEQ ID NO 1-44 and/or encoding at least the following HPV derived cytotoxic T lymphocyte (CTL) epitopes: SEQ ID NO 1, 23, 39, and 45-88. Furthermore, the present invention also encompasses a polypeptide encoded by the polynucleotide as described herein. Preferably, the epitopes of the polyepitope construct are directly or indirectly linked to one another in the same reading frame.

The term "construct" as used herein generally denotes a composition that does not occur in nature. As such, the polynucleotide construct of the present invention does not encode a wild-type full-length protein from HPV but encodes a chimeric protein containing isolated epitopes from at least one HPV protein not necessarily in the same sequential order as in nature. A construct may be a "polynucleotide construct" or a "polypeptide construct". The polynucleotides or (poly)peptides as described herein are "isolated" or "biologically pure". The term "isolated" refers to material that is substantially free from components that normally accompany it as found in its naturally occurring environment. However, it should be clear that the isolated polynucleotide or (poly)peptide of the present invention might comprise heterologous cell components or a label and the like. An "isolated" epitope refers to an epitope that does not include the neighboring amino acids of the whole sequence of the antigen or polynucleotide from which the epitope was derived. As such, the present invention relates to a polynucleotide comprising a polyepitope construct comprising the following isolated HPV CTL epitopes: SEQ ID NO 1-44 and/or SEQ ID NO 1, 23, 39, and 45-88. It is thus to be understood that the construct of the present invention comprises isolated epitopes that are not embedded in the naturally occurring full length protein from HPV. The specific epitopes in the construct can be directly or indirectly linked in any order or in the order as given in FIGS. 1A, 2A, 3 and 4. A construct can be produced by synthetic technologies, e.g. recombinant DNA preparation and expression or chemical synthetic techniques for nucleic acids and amino acids. A construct can also be produced by the addition or affiliation of one material with another such that the result is not found in nature in that form.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) molecules.

With regard to a particular nucleic acid sequence, a "nucleic acid epitope" is a set of nucleic acids that encode for a particular amino acid sequence that forms an epitope.

In an immune system setting, in vivo or in vitro, an epitope is the collective features of a molecule, such as primary, secondary and tertiary peptide structure, and charge, that together form a site recognized by a T cell receptor and MHC molecule, or an immunoglobulin. The term "polypeptide" is used interchangeably with "oligopeptide" and designates a series of amino acids, connected one to the other, typically by peptide bonds between the amino and carboxyl groups of adjacent amino acids.

The term "polyepitope construct" when referring to nucleic acids and polynucleotides can be used interchangeably with the terms "minigene" and "polyepitope nucleic acid" and other equivalent phrases, and comprises multiple nucleic acid epitopes that encode peptides of any length that can bind to a molecule functioning in the immune system, preferably a HLA class I or a HLA class II and a T-cell receptor. All disclosures herein with regard to nucleic acid epitopes comprised in a polynucleotide construct apply mutatis mutandis to epitopes comprised in an amino acid construct. The epitopes in a polyepitope construct can be HLA class I epitopes and/or HLA class II epitopes. HLA class I epitopes are referred to as CTL epitopes and HLA class II epitopes are referred to as HTL epitopes. Some polyepitope constructs can have a subset of HLA class I epitopes and another subset of HLA class II epitopes. A CTL epitope usually consists of 13 or less amino acid residues in length, 12 or less amino acids in length, or 11 or less amino acids in length, preferably from 8 to 13 amino acids in length, more preferably from 8 to 11 amino acids in length (i.e. 8, 9, 10, or 11), and most preferably 9 or 10 amino acids in length. A HTL epitope consists of 50 or less amino acid residues in length, and usually from 6 to 30 residues, more usually from 12 to 25, and preferably consists of 15 to 20 (i.e. 15, 16, 17, 18, 19, or 20) amino acids in length.

The polyepitope construct described herein preferably includes 2 or more, 5 or more, 10 or more, 15 or more, 20 or more, 25 or more, 30 or more, 40 or more, 50 or more, 100 or more and up till 150 epitopes, preferably up till 130 and more preferably up till 80 epitopes. More specific, the polyepitope construct consists of or comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, or more epitopes.

In a preferred embodiment, the polyepitope construct of the present invention further comprises at least one CTL and/or HTL epitope. Said "further" CTL and/or HTL epitope to be used in combination with the epitopes of the present invention can be derived from HPV or from a foreign antigen or organism (non-HPV). Accordingly, the present invention encompasses a polynucleotide comprising a polyepitope construct encoding at least the following HPV CTL epitopes characterized by: SEQ ID NO 1-44 and/or SEQ ID NO 1, 23, 39, and 45-88, and at least one additional CTL and/or HTL epitope, and wherein the construct does not encode a full-length protein from HPV. Preferably, the at least one CTL and/or HTL epitope is derived from HPV, and more specifically from the E1, E2, E4, E5, E6, E7, L1 and/or L2 protein. Preferably, the at least one HTL epitope is selected from Table 2. Any combination of HTL epitopes and even all of the HTL epitopes as given in Table 2 can be included into the construct. In a further embodiment, the present invention relates to a polynucleotide comprising nucleic acids encoding a polyepitope construct comprising respectively the following isolated HPV CTL and HTL epitopes: SEQ ID NO 1-44 and SEQ ID 89-105, or alternatively SEQ ID NO 1, 23, 39, and 45-88 and SEQ ID NO 106-121. The HTL epitopes in the construct can be directly or indirectly linked in any order or in the order as given in FIGS. 1B and 2B. In a further embodiment, the invention encompasses a polypeptide encoded by said nucleotide.

The further epitopes can be derived from any desired antigen of interest, e.g. a viral antigen, a tumor antigen or any pathogen. Multiple HLA class I or class II epitopes present in a polyepitope construct can be derived from the same antigen, or from different antigens. For example, a polyepitope construct can contain one or more HLA binding epitopes than can be derived from two different antigens of the same virus, or from two different antigens of different viruses. In a preferred embodiment, the epitopes of the present invention are derived from HPV and more specifically from the E1, E2, E4, E5, E6, E7, L1 and/or L2 protein. There is no limitation on the length of said further epitopes, these can have a length of e.g. 5, 6, 7, 8, 9, 10, 11, 12, 13, 14, 15, 16, 17, 18, 19, 20, 21, 22, 23, 24, 25, 30 or more amino acids. The "at least one" can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 115, 120, 125, 130 or even more epitopes.

In a preferred embodiment, the polyepitope construct of the present invention further comprises the universal T cell epitope called PADRE® (Pharmexa, San Diego; described for example in U.S. Pat. No. 5,736,142 or U.S. Pat. No. 6,413,935 or International Application WO95/07707 or WO97/26784, which are enclosed herein by reference). A "PanDR binding epitope or PADRE® epitope" is a member of a family of molecules that binds more than one HLA class II DR molecule. The pattern that defines the PADRE® family of molecules can be thought of as an HLA Class II supermotif. PADRE® binds to most HLA-DR molecules and stimulates in vitro and in vivo human helper T lymphocyte (HTL) responses. In a preferred embodiment, the PADRE® epitope is characterized by SEQ ID NO 122.

Alternatively, HTL epitopes from universally used vaccines such as tetanos toxoid can be included. In an alternative embodiment, the further epitopes are B cell epitopes.

The aim of the present invention is to provide strategies to optimize antigenicity and immunogenicity of polyepitope vaccines encompassing a large number of relevant epitopes, and to provide optimized polyepitope vaccines, particularly HPV polyepitope constructs. Examples of such constructs are depicted in FIGS. 5-8. Said constructs comprise a plurality of HPV-specific CU and HTL epitopes that are efficiently processed, and thus highly immunogenic. Hence, the present invention is directed to a polynucleotide comprising or consisting of a polyepitope construct encoding CTL and HTL epitopes, whereby the polyepitope construct is represented by or comprised in SEQ ID NO 124, SEQ ID NO 126, SEQ ID NO 128 or SEQ ID NO 130.

In a further embodiment, the polyepitope construct encodes a polypeptide comprising or consisting of an amino acid sequence represented by or comprised in SEQ ID NO 123, SEQ ID NO 125, SEQ ID NO 127 or SEQ ID NO 129.

More specific, the polyepitope construct encodes the amino acid sequence consisting of or comprising the sequence represented by SEQ ID NO 156, SEQ ID NO 158, SEQ ID NO 160, or SEQ ID NO 162. More particular, the polyepitope construct consists of or comprises the nucleic acid sequence represented by SEQ ID NO 157, SEQ ID NO 159, SEQ ID NO 161, or SEQ ID NO 163.

The term "immunogenic" or "immunogenicity" as used herein is the ability to evoke an immune response.

Immunogenicity can be manifested in several different ways. Immunogenicity corresponds to whether an immune response is elicited at all, and to the vigor of any particular response, as well as to the extent of a population in which a response is elicited. For example, a peptide might elicit an immune response in a diverse array of the population, yet in no instance produce a vigorous response. In accordance with these principles, close to 90% of high affinity binding peptides have been found to be immunogenic, as contrasted with about 50% of the peptides that bind with intermediate affinity (Sette et al., 1994; Alexander et al., 2003). Moreover, higher binding affinity peptides lead to more vigorous immunogenic responses. As a result, less peptide is required to elicit a similar biological effect if a high affinity binding peptide is used.

Various strategies can be utilized to evaluate immunogenicity, including but not limited to:
1) Evaluation of primary T cell cultures from normal individuals (see, e.g., Wentworth et al., 1995; Celis et al., 1994;

Tsai et al., 1997; Kawashima et al., 1998). This procedure involves the stimulation of peripheral blood lymphocytes (PBL) from normal subjects with a test peptide in the presence of antigen-presenting cells in vitro over a period of several weeks. T cells specific for the peptide become activated during this time and are detected using, e.g., a $^{51}$Cr-release assay involving peptide sensitized target cells.

2) Immunization of HLA transgenic mice (see, e.g., Wentworth et al., 1996; Alexander et al., 1997) or surrogate mice. In this method, peptides (e.g. formulated in incomplete Freund's adjuvant) are administered subcutaneously to HLA transgenic mice or surrogate mice. Eleven to 14 days following immunization, splenocytes are removed. Cells are either cultured in vitro in the presence of test peptide for approximately one week. Peptide-specific T cells are detected using, e.g., a $^{51}$Cr-release assay involving peptide-sensitized target cells and/or target cells expressing endogenously generated antigen. Alternatively, cells are incubated overnight together with peptide-loaded APC in the IFNg ELISPOT assay for the quantitation of peptide-specific single T cells releasing mouse interferon gamma upon stimulation.

3) Demonstration of recall T cell responses from immune individuals who have effectively been vaccinated, recovered from infection, and/or from chronically infected patients (see, e.g., Rehermann et al., 1995; Doolan et al., 1997; Bertoni et al., 1997; Threlkeld et al., 1997; Diepolder et al., 1997). In applying this strategy, recall responses are detected by culturing PBL from subjects that have been naturally exposed to the HPV antigen, for instance through infection, and thus have generated an immune response "naturally", or from patients who were vaccinated with a vaccine comprising the epitope of interest. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized target cells, T cell proliferation, or cytokine release.

A given epitope is stated to be immunogenic if T cell reactivity can be shown to target cells sensitized with that peptide. Immunogenicity for a given epitope can further be described by the number of individuals in a group of HLA matched infected or vaccinated subjects (e.g. humans, primates, transgenic mice, surrogate mice) that show T cell reactivity to that particular epitope, or e.g. by the number of spots detected in an ELISPOT assay. Immunogenicity for the epitopes of the invention is indicated in Tables 8 and 9.

Epitope analogs derived from naturally occurring HPV sequences exhibit increased binding to HLA molecules and immunogenicity due to the modification of specific amino acid residues with respect to the naturally occurring HPV sequence. Accordingly, in a specific embodiment, the epitopes of the present invention may be analoged to modify binding affinity and/or the ability to bind to multiple alleles within an HLA supertype. Analog epitopes can be created by altering the presence or absence of particular residues in the primary anchor positions. Such analogs are used to modulate the binding affinity of a peptide comprising a particular motif or supermotif. Accordingly, the analoged epitopes as given in Table 1 are also part of the invention.

A "preferred primary anchor residue" is an anchor residue of a motif or supermotif that is associated with optimal binding. HLA binding motifs, supermotifs and preferred primary anchor residues are given in e.g. WO05/089164 (Pharmexa Inc. et al.; incorporated herein by reference). "Heteroclitic analogs" are defined herein as epitopes with increased potency for a specific T cell, as measured by increased responses to a given dose, or by a requirement of lesser amounts to achieve the same response. Advantages of heteroclitic analogs include that the epitopes can be more potent, or more economical (since a lower amount is required to achieve the same effect). In addition, modified epitopes might overcome antigen-specific T cell unresponsiveness (T cell tolerance). (See e.g. WO01/36452, which is hereby incorporated by reference)

The epitopes of the polyepitope construct are directly or indirectly linked to one another in the same reading frame. More specific, the epitopes are either contiguous (directly linked) or are separated by a linker or a spacer nucleic acid encoding a spacer amino acid or spacer peptide (indirectly linked).

"Link" or "join" refers to any method known in the art for functionally connecting peptides (direct of via a linker), including, without limitation, recombinant fusion, covalent binding, non-covalent binding, disulfide binding, ionic binding, hydrogen binding, polymerization, cyclization, electrostatic binding and connecting through a central linker or carrier. Polymerization can be accomplished for example by reaction between glutaraldehyde and the —NH2 groups of the lysine residues using routine methodology.

In a specific embodiment, the polyepitope construct of the present invention further comprises three or a plurality of spacer nucleic acids, linked in the same reading frame to the CTL and/or HTL epitope nucleic acids. A reading frame is a contiguous and non-overlapping set of three-nucleotide codons in DNA or RNA. There are 3 possible reading frames in a strand and six in a double stranded DNA molecule. "In the same reading frame" means that there is no shift from one frame to another that could lead to different genes/proteins.

To develop polyepitope constructs using the epitopes of the present invention, said epitopes can be sorted and optimized using a computer program or, for fewer epitopes, not using a computer program. "Sorting epitopes" refers to determining or designing an order of the epitopes in a polyepitope construct.

"Optimizing" refers to increasing the antigenicity of a polyepitope construct having at least one epitope pair by sorting epitopes to minimize the occurrence of junctional epitopes, and inserting a spacer residue (as described herein) to further prevent the occurrence of junctional epitopes or to provide a flanking residue. As described herein, a "flanking residue" is a residue that is positioned next to an epitope. A flanking residue can be introduced or inserted at a position adjacent to the N-terminus (N+1) or the C-terminus (C+1) of an epitope. An increase in immunogenicity or antigenicity of an optimized polyepitope construct is measured relative to a polyepitope construct that has not been constructed based on the optimization parameters by using assays known to those skilled in the art, e.g. assessment of immunogenicity in HLA transgenic mice, ELISPOT, tetramer staining, $^{51}$Cr release assays, and presentation on antigen presenting cells in the context of MHC molecules.

The process of optimizing polyepitope constructs is given e.g. in WO01/47541 and WO04/031210 (Pharmexa Inc. et al.; incorporated herein by reference). According to a specific embodiment, the polyepitope construct of the present invention is optimized for CTL and/or HTL epitope processing. More particular, the optimization comprises the introduction of one or more spacers. More preferred, the polyepitope construct as described herein comprises 0, 3, 6, 9, 12, 15, 18, or more spacer nucleic acids or 0, 1, 2, 3, 4, 5, 6, or more spacer amino acids between two epitopes. A "spacer" refers to a sequence that is inserted between two epitopes in a polyepitope construct to prevent the occurrence of junctional epitopes, or to facilitate cleavage between epitopes and thereby enhance epitope presentation. "Junctional epitopes" refer to epitopes recognized by the immune system, not present in the target antigen, and only created by the man-made juxtaposition of epitopes. A spacer nucleic acid may encode one or more amino acids. A spacer nucleic acid flanking a HLA class I epitope in a polyepitope construct encodes preferably 1 to 8, and more preferably 1 to 5 amino acids, i.e. 1, 2, 3, 4 or 5 amino acids. A spacer nucleic acid flanking a HLA class II epitope in a polyepitope construct encodes 1 to 8 amino acids, preferably 5, 6, 7, or more amino acids, and more preferably 5 or 6 amino acids. A spacer nucleic acid separating a HLA class I epitope and a class II epitope in a polyepitope construct encodes preferably 1 to 8, and more preferably 1 to 5 amino acids, i.e. 1, 2, 3, 4 or 5 amino acids. The number of spacers in a construct, the number of amino acids in a spacer, and the amino acid composition of a spacer can be selected to optimize epitope processing and/or minimize junctional epitopes. It is preferred that spacers are selected by concomitantly optimizing epitope processing and preventing junctional motifs. The "spacer amino acid" or "spacer peptide" is typically comprised of one or more relatively small, neutral molecules, such as amino acids or amino acid mimetics, which are substantially uncharged under physiological conditions. For example, spacers flanking HLA class II epitopes preferably include G (Gly), P (Pro), and/or N (Asn) residues. A particularly preferred spacer for flanking a HLA class II epitope includes alternating G and P residues, for example, (GP)n, (PG)n, (GP)nG, (PG)nP, and so forth, where n is an integer between 1 and 10, preferably 2 or 3, and where a specific example of such a spacer is GPGPG (SEQ ID NO 155). For separating class I epitopes, or separating a class I and a class II epitope, the spacers are typically selected from, e.g., A (Ala), N (Asn), K (Lys), G (Gly), L (Leu), I (Ile), R (Arg), Q (Gln), S (Ser), C (Cys), P (Pro), T (Thr), or other neutral spacers of nonpolar amino acids or neutral polar amino acids, though polar residues could also be present. A preferred spacer, particularly for HLA class I epitopes, comprises or consists of 1, 2, 3 or more consecutive alanine (A), Lysine (K), Asparagine (N) or Glycine (G) residues, or a combination of K (Lys) and A (Ala) residues, e.g. KA, KAA or KAAA, a combination of N (Asn) and A (Ala) residues, e.g. NA, NAA or NAAA or a combination of G (Gly) and A (Ala) residues, e.g. GA, GAA or GAAA. The present invention is thus directed to a polynucleotide comprising a polyepitope construct as described herein, and wherein the epitopes in the construct are separated by one or more spacer amino acids. In a preferred embodiment, the one or more spacer amino acids are selected from the group consisting of: K, R, N, Q, G, A, S, C, G, P and T. In some polyepitope constructs, it is sufficient that each spacer nucleic acid encodes the same amino acid sequence. In other polyepitope constructs, one or more of the spacer nucleic acids may encode different amino acid sequences.

The only outer limit on the total length and nature of each spacer sequence derives from considerations of ease of synthesis, proteolytic processing, and manipulation of the polynucleotide.

The (poly)peptides of the present invention can be in their natural (uncharged) forms or in forms which are salts, and either free of modifications such as glycosylation, side chain oxidation, or phosphorylation or containing these modifications. Also included in the definition are peptides modified by additional substituents attached to the amino acids side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid sequence referenced, and may be subject to those of the foregoing modifications as long as its functionality is not destroyed.

Moreover, the present invention also contemplates a polyepitope construct comprising or consisting of multiple repeats or combinations of any of the epitopes of the present invention, as given in Tables 1 and 2. The polyepitope construct can exist as a homopolymer comprising multiple copies of the same (combination of) peptide(s), or as a heteropolymer of various peptides. Polymers have the advantage of increased immunological reaction and, where different peptide epitopes are used to make up the polymer, the additional ability to induce HTL's and/or CTLs that react with different antigenic determinants of the pathogenic organism targeted for an immune response. As an alternative, the individual epitopes of the present invention are not linked into a construct and can be combined separately e.g. in a composition.

The present invention also encompasses a method of making a polyepitope construct. Polynucleotides or nucleic acids that are not commercially available can be chemically synthesized according to the solid phase phosphoramidite triester method first described by Beaucage & Caruthers, 1981, using an automated synthesizer, as described in Van Devanter et. al., 1984. Purification of polynucleotides is by either native acrylamide gel electrophoresis or by anion-exchange HPLC as described in Pearson & Reanier, 1983. Other purification methods are reversed phase separation and hydroxyapatite and are well known to the skilled person. Chemically synthesized and purified polynucleotides can be assembled into longer polynucleotides by PCR-based methods (Stemmer et al., 1995; Kriegler et al., 1991).

The epitopes of the polyepitope constructs are typically subcloned into an expression vector that contains a promoter to direct transcription, as well as other regulatory sequences such as enhancers and polyadenylation sites. Additional elements of the vector are e.g. signal or target sequences, translational initiation and termination sequences, 5' and 3' untranslated regions and introns, required for expression of the polyepitope construct in host cells.

Polyepitope constructs can for example be prepared according to the methods set forth in Ishioka et al., 1999; Velders et al., 2001; or as described in WO04/031210—Pharmexa Inc. (all incorporated herein by reference).

A polyepitopic polypeptide or the polypeptide comprising the polyepitope construct can be generated synthetically or recombinantly. The polyepitopic polypeptide can be expressed as one protein. In order to carry out the expression of the polyepitopic polypeptide in bacteria, in eukaryotic cells (including yeast) or in cultured vertebrate hosts such as Chinese Hamster Ovary (CHO), Vero cells, RK13, COS1, BHK, and MDCK cells, or invertebrate hosts such as insect cells, the following steps are carried out:

transformation of an appropriate cellular host with a recombinant vector, or by means of adenoviruses, influenza viruses, BCG, and any other live carrier systems, in which a nucleotide sequence coding for one of the polypeptides of the invention has been inserted under the control of the appropriate regulatory elements, particularly a promoter recognized by the polymerases of the cellular host or of the live carrier system and in the case of a prokaryotic host, an appropriate ribosome binding site (RBS), enabling the expression in said cellular host of said nucleotide sequence, culture of said transformed cellular host under conditions enabling the expression of said insert.

As such, the present invention also relates to a cell or host cell comprising a polynucleotide, a polypeptide or a vector containing a polyepitope construct. In a further embodiment, the "cell" of the present invention is an antigen presenting cell (APC) comprising the polynucleotide as described herein.

The polyepitopic polypeptide can be purified by methods well known to the person skilled in the art (see e.g. Lichty J J et al., 2005; Gaberc-Porekar V et al., 2001).

For therapeutic or prophylactic immunization purposes, the polyepitope construct of the invention can be expressed by vectors. The present invention thus also relates to a vector comprising the polynucleotide of the present invention. The term "vector" may comprise a plasmid, a cosmid, a prokaryotic organism, a phage, a virus or an eukaryotic organism such as an animal or human cell or a yeast cell. The expression vector typically contains a transcription unit or expression cassette that contains all the additional elements required for the expression of the polyepitope construct in host cells. A typical expression cassette thus contains a promoter operably linked to the polyepitope construct and signals required for efficient polyadenylation of the transcript. Additional elements of the cassette may include enhancers and introns with functional splice donor and acceptor sites.

Suitable promoters are well known in the art and described, e.g., in Sambrook et al., Molecular cloning, A Laboratory Manual ($2^{nd}$ ed. 1989) and in Ausubel et al, Current Protocols in Molecular Biology (1994). Eukaryotic expression systems for mammalian cells are well known in the art and are commercially available. Such promoter elements include, for example, cytomegalovirus (CMV), Rous sarcoma virus long terminal repeats (RSV LTR) and Simian Virus 40 (SV40). See, e.g. U.S. Pat. No. 5,580,859 and U.S. Pat. No. 5,589,466 (Vical Inc.; incorporated by reference) for other suitable promoter sequences.

In addition to a promoter sequence, the expression cassette can also contain a transcription termination region downstream of the structural gene to provide for efficient termination. The termination region may be obtained from the same gene as the promoter sequence or may be obtained from different genes.

In a particular embodiment, the polynucleotide of the present invention further comprises one or more regulatory sequences. By "regulatory sequence" is meant a polynucleotide sequence that contributes to or is necessary for the expression of an operably associated nucleic acid or nucleic acid construct in a particular host organism. The regulatory sequences that are suitable for prokaryotes, for example, include a promoter, optionally an operator sequence, and an internal ribosome binding site (IRES). Eukaryotic cells are known to utilize promoters, polyadenylation signals, and enhancers. Promoter may be a CMV promoter or other promoter described herein or known in the art. Regulatory sequences include IRESs. Other specific examples of regulatory sequences are described herein and otherwise known in the art.

In a further embodiment, the polynucleotide of the present invention further comprises one or more MHC class I and/or MHC class II "targeting nucleic acids" or "targeting sequences". The use of a MHC targeting sequence enhances the immune response to an antigen, relative to delivery of antigen alone, by directing the peptides to the site of MHC molecule assembly and transport to the cell surface, thereby providing an increased number of MHC molecule-peptides complexes available for binding to and activation of T cells. Examples of possible targeting sequences are well known to the skilled person and are described e.g. in WO04/031210 (Pharmexa Inc. et al.). In a specific embodiment, the epitopes of polyepitope construct of the present invention are operably linked to a nucleic acid encoding a targeting sequence selected from the group consisting of tissue plasminogen activator signal sequence, insulin signal sequence, endoplasmic reticulum signal sequence, LAMP-1 lysosomal targeting sequence, LAMP-2 lysosomal targeting sequence, HLA-DM lysosomal targeting sequence, HLA-DM-association sequences of HLA-DO, Ig-alpha cytoplasmic domain, Ig-beta cytoplasmic domain, Ii protein, influenza matrix protein, HBV surface antigen, HBV core antigen, and yeast Ty protein.

In a further embodiment, the polynucleotide of the present invention further comprises at least one signal sequence. A "signal sequence" is or encodes a 16-30 amino acid sequence, in a secreted polypeptide, that directs the protein to its target compartment or membrane. A preferred signal sequence is the Igkappa signal sequence.

The phrase "operably linked" or "operatively linked" refers to a linkage in which a nucleotide sequence is connected to another nucleotide sequence (or sequences) in such a way as to be capable of altering the functioning of the sequence (or sequences). For example, a nucleic acid or polyepitope nucleic acid construct that is operably linked to a regulatory sequence, such as a promoter/operator, places expression of the nucleic acid or construct under the influence or control of the regulatory sequence. Two nucleotide sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two nucleotide sequences does not (1) result in the introduction of a frame-shift mutation nor (2) prevent the expression regulatory sequences to direct the expression of the mRNA or protein. Thus, a promoter region would be operably linked to a nucleotide sequence if the promoter were capable of effecting transcription of that nucleotide sequence.

One or more cysteine residues comprised in epitopes of the polyepitope construct may be "reversibly or irreversibly blocked". An "irreversibly blocked cysteine" is a cysteine of which the cysteine thiol-group is irreversibly protected by chemical means. In particular, "irreversible protection" or "irreversible blocking" by chemical means refers to alkylation, preferably alkylation of a cysteine in a protein by means of alkylating agents, such as, for example, active halogens, ethylenimine or N-(iodoethyl)trifluoro-acetamide. In this respect, it is to be understood that alkylation of cysteine thiol-groups refers to the replacement of the thiol-hydrogen by $(CH_2)_nR$, in which n is 0, 1, 2, 3 or 4 and R=H, COOH, $NH_2$, $CONH_2$ phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine.

A "reversibly blocked cysteine" is a cysteine of which the cysteine thiol-groups is reversibly protected. In particular, the term "reversible protection" or "reversible blocking" as used herein contemplates covalently binding of modification agents to the cysteine thiol-groups, as well as manipulating the environment of the protein such, that the redox state of the cysteine thiol-groups remains (shielding). Reversible protection of the cysteine thiol-groups can be carried out chemically or enzymatically. The term "reversible protection by enzymatical means" as used herein contemplates reversible protection mediated by enzymes, such as for example acyl-transferases, e.g. acyl-transferases that are involved in catalysing thio-esterification, such as palmitoyl acyltransferase. The term "reversible protection by chemical means" as used herein contemplates reversible protection, using conditions or agents well known to the person skilled in the art.

The removal of the reversibly protection state of the cysteine residues can chemically or enzymatically accomplished by e.g.:

- a reductant, in particular DTT, DTE, 2-mercaptoethanol, dithionite, $SnCl_2$, sodium borohydride, hydroxylamine, TCEP, in particular in a concentration of 1-200 mM, more preferentially in a concentration of 50-200 mM;
- removal of the thiol stabilising conditions or agents by e.g. pH increase;
- enzymes, in particular thioesterases, glutaredoxine, thioredoxine, in particular in a concentration of 0.01-5 µM, even more particular in a concentration range of 0.1-5 µM.;
- combinations of the above described chemical and/or enzymatical conditions.

The removal of the reversibly protection state of the cysteine residues can be carried out in vitro or in vivo, e.g. in a cell or in an individual.

Alternatively, one cysteine residue, or 2 or more cysteine residues comprised in the HPV epitopes as described herein may be mutated to a natural amino acid, preferentially to methionine, glutamic acid, glutamine or lysine.

Compositions and Vaccines

The current invention furthermore relates to compositions comprising a polynucleotide, a polypeptide or a vector comprising the HPV polyepitope construct as described herein, or a combination thereof. In a specific embodiment, the composition furthermore comprises at least one of a pharmaceutically acceptable excipient, i.e. a carrier, adjuvant or vehicle. The terms "composition", "immunogenic composition" and "pharmaceutical composition" can be used interchangeably. More particularly, said immunogenic composition is a vaccine composition. Even more particularly, said vaccine composition is a prophylactic vaccine composition. Alternatively, said vaccine composition may also be a therapeutic vaccine composition. The prophylactic vaccine composition refers to a vaccine aimed for preventing persistent HPV infection and to be administered to healthy persons who are not yet infected with HPV. The therapeutic vaccine composition refers to a vaccine aimed for treatment of HPV infection and to be administered to patients being infected with HPV.

A vaccine or vaccine composition is an immunogenic composition capable of eliciting an immune response sufficiently broad and vigorous to provoke at least one or both of:

- a stabilizing effect on the multiplication of a pathogen already present in a host and against which the vaccine composition is targeted. A vaccine composition may also induce an immune response in a host already infected with the pathogen against which the immune response leading to stabilization, regression or resolving of the disease. In case of HPV, a vaccine e.g. prevents further progression of CIN and prevents the development of cervical cancer; or promotes the regression of the lesions; and
- an increase of the rate at which a pathogen newly introduced in a host, after immunization with a vaccine composition targeted against said pathogen, is resolved from said host.

In particular the composition of the invention is a HPV immunogenic composition or vaccine. In particular, the composition or vaccine comprises an effective amount of the polynucleotide, nucleic acids, polypeptide or peptides of the present invention. In a specific embodiment, said composition or vaccine comprises a vector, a plasmid, a recombinant virus and/or host cell comprising the polyepitope construct of the present invention. Said composition or vaccine may additionally comprise one or more further active substances and/ or at least one of a pharmaceutically acceptable excipient, being a carrier, adjuvant or vehicle.

An "effective amount" of a polynucleotide or polypeptide in a vaccine or composition is referred to as an amount required and sufficient to elicit an immune response. It will be clear to the skilled artisan that the immune response sufficiently broad and vigorous to provoke the effects envisaged by the vaccine or composition may require successive (in time) immunizations with the vaccine or composition as part of an administration scheme or vaccination schedule. The "effective amount" may vary depending on the health and physical condition of the individual to be treated, the age of the individual to be treated (e.g. dosing for infants may be lower than for adults), the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting pathogen and other relevant factors. Dosage treatment may be a single dose schedule or a multiple dose schedule. The vaccine or composition may be administered in conjunction with other immunoregulatory agents. The dosages, routes of administration, and dose schedules are adjusted in accordance with methodologies known in the art.

Carriers, Adjuvants and Vehicles—Delivery

The present invention furthermore relates to a method of inducing an immune response against HPV in an individual comprising administering the polynucleotide, the vector, the polypeptide, the host cell or the composition of the present invention. More specific, the present invention relates to a method of treating HPV infection and more specific HPV-related disease.

The present invention furthermore relates to a method for inducing an immune response at various stages, e.g. CIN 1-3, of HPV-related disease thereby aiming for higher efficacy, comprising the administration of the polynucleotide, the vector, the polypeptide, the host cell or the composition containing epitopes from differentially expressed HPV antigens.

Various art-recognized delivery systems may be used to deliver a polyepitope construct into appropriate cells. The polynucleotides and polypeptides encoded thereby can be delivered in a pharmaceutically acceptable carrier or as colloidal suspensions, or as powders, with or without diluents. They can be "naked" or associated with delivery vehicles and delivered using delivery systems known in the art.

A "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. Preferably, a pharmaceutically acceptable carrier or adjuvant enhances the immune response elicited by an antigen.

A "pharmaceutically acceptable vehicle" includes vehicles such as water, saline, physiological salt solutions, glycerol, ethanol, etc. Auxiliary substances such as wetting or emulsifying agents, pH buffering substances, preservatives may be included in such vehicles.

Typically, a composition or vaccine is prepared as an injectable, either as a liquid solution or suspension. Injection may be subcutaneous, intramuscular, intravenous, intraperitoneal, intrathecal, intradermal, intraepidermal, or by "gene gun". Other types of administration comprise electroporation, implantation, suppositories, oral ingestion, enteric application, inhalation, aerosolization or nasal spray or drops. Solid forms, suitable for dissolving in, or suspension in, liquid vehicles prior to injection may also be prepared. The preparation may also be emulsified or encapsulated in liposomes for enhancing adjuvant effect.

A liquid formulation may include oils, polymers, vitamins, carbohydrates, amino acids, salts, buffers, albumin, surfactants, or bulking agents. Any physiological buffer may be used, but citrate, phosphate, succinate, and glutamate buffers or mixtures thereof are preferred.

Another drug delivery system for increasing circulatory half-life is the liposome. The peptides and nucleic acids of the invention may also be administered via liposomes, which serve to target a particular tissue, such as lymphoid tissue, or to target selectively infected cells, as well as to increase the half-life of the peptide and nucleic acids composition. Liposomes include emulsions, foams, micelles, insoluble monolayers, liquid crystals, phospholipid dispersions, lamellar layers and the like.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

The approach known as "naked DNA" is currently being used for intramuscular (IM) administration in clinical trials. To maximize the immunotherapeutic effects of DNA vaccines, an alternative method for formulating purified plasmid DNA may be desirable. A variety of methods have been described, and new techniques may become available. Cationic lipids can also be used in the formulation (see, e.g., as described by WO 93/24640; Mannino & Gould-Fogerite 1988; U.S. Pat. No. 5,279,833; WO 91/06309; and Felgner et al., 1987). In addition, glycolipids, fusogenic liposomes, peptides and compounds referred to collectively as protective, interactive, non-condensing compounds could also be complexed to purified plasmid DNA to influence variables such as stability, intramuscular dispersion, or trafficking to specific organs or cell types.

Further examples of DNA-based delivery technologies include facilitated (bupivicaine, polymers, peptide-mediated) delivery, cationic lipid complexes, particle-mediated ("gene gun") or pressure-mediated delivery (see, e.g., U.S. Pat. No. 5,922,687), DNA formulated with charged or uncharged lipids, DNA formulated in liposomes, emulsified DNA, DNA included in a viral vector, DNA formulated with a transfection-facilitating protein or polynucleotide, DNA formulated with a targeting protein or polypeptide, DNA formulated with calcium precipitating agents, DNA coupled to an inert carrier molecule, and DNA formulated with an adjuvant. In this context it is noted that practically all considerations pertaining to the use of adjuvants in traditional vaccine formulation apply to the formulation of DNA vaccines.

Recombinant virus or live carrier vectors may also be directly used as live vaccines in humans. Accordingly the present invention also relates to a recombinant virus, a bacterial vector, a yeast vector or a plasmid, and a host cell comprising the polynucleotide as described herein.

In a preferred embodiment of the invention, the polynucleotide is introduced in the form of a vector wherein expression is under control of a promoter. Therefore, further embodiments of the present invention are an expression vector which comprises a polynucleotide encoding at least the polyepitope construct as described herein, and which is capable of expressing the respective peptides, a host cell comprising the expression vector and a method of producing and purifying the herein described peptides, and a pharmaceutical composition comprising the herein described peptides and a pharmaceutically acceptable carrier and/or adjuvants.

Detailed disclosures relating to the formulation and use of nucleic acid vaccines are available, e.g. by Donnelly J. J. et al, 1997 and 1997a. Examples of expression vectors include attenuated viral hosts, such as a pox virus. As an example of this approach, vaccinia virus is used as a vector to express nucleotide sequences that encode the peptides of the invention. Upon introduction into a host, the recombinant vaccinia virus expresses the immunogenic peptide, and thereby elicits a host CU and/or HTL response. Vaccinia vectors, for example Modified Vaccinia Ankara (MVA), and methods useful in immunization protocols are described in, e.g., U.S. Pat. No. 4,722,848. Another vector is BCG (Bacille Calmette Guerin). BCG vectors are described in Stover et al., 1991. Preferable yeast vectors are *Saccharomyces cerevisiae, Pichia pastoris* and *Hansenula polymorpha*. Further examples are: Alphaviruses (Semliki Forest Virus, Sindbis Vrius, Venezuelan Equine Encephalitis Virus (VEE)), Herpes simplex Virus (HSV), replication-deficient strains of Adenovirus (human or simian), SV40 vectors, CMV vectors, papillomavirus vectors, and vectors derived from Epstein Barr virus. A wide variety of other vectors useful for therapeutic administration or immunization of the epitopes of the invention, e.g. retroviral vectors, *Salmonella typhi* vectors, detoxified anthrax toxin vectors, and the like, will be apparent to those skilled in the art from the description herein.

Additional vector modifications may be desired to optimize polynucleotide expression and immunogenicity. In some cases, introns are required for efficient gene expression, and one or more synthetic or naturally-occurring introns could be incorporated into the transcribed region of the polynucleotide construct. The inclusion of mRNA stabilization sequences and sequences for replication in mammalian cells may also be considered for increasing polynucleotide expression. In addition, immunostimulatory sequences (ISSs or CpGs) appear to play a role in the immunogenicity of nucleic acid vaccines. These sequences may be included in the vector, outside the polynucleotide coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules. Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-P) may be beneficial in certain diseases.

The use of polyepitope constructs is described in, e.g., U.S. Pat. No. 6,534,482 (Pharmexa Inc.); An and Whitton, 1997; Thomson et al., 1996; Whitton et al., 1993; Hanke et al., 1998. For example, a polyepitope DNA plasmid encoding supermotif- and/or motif-bearing HPV epitopes derived from multiple regions of the HPV polyprotein sequence, the PADRE® universal helper T cell epitope (or multiple HTL epitopes from HPV), and an endoplasmic reticulum-translocating signal sequence can be engineered.

All disclosures herein which relate to use of adjuvants in the context of protein or (poly)peptide based pharmaceutical compositions apply mutatis mutandis to their use in nucleic acid and vector vaccination technology. The same holds true for other considerations relating to formulation and mode and route of administration and, hence, also these considerations discussed herein in connection with a traditional pharmaceutical composition apply mutatis mutandis to their use in nucleic acid and vector vaccination technology.

Medical Use

In a further embodiment, the present invention relates to the polynucleotide, the vector, the host cell, the polypeptide or the composition of the present invention for use as a medicament. Preferably, said medicament is a vaccine. More specifically, the present invention relates to the use of the polyepitope construct comprising the epitopes of the present invention, or the nucleic acid sequence encoding said epitopes, for the manufacture of a medicament for preventing and/or treating an HPV infection and/or HPV related disease. In a specific embodiment the invention also relates to a vector, a plasmid, a recombinant virus or host cell comprising the polynucleotide as described herein for the manufacture of a medicament for preventing and/or treating an HPV infection and/or HPV related disease.

The present invention also encompasses the polyepitope construct comprising the epitopes of the present invention, or the nucleic acid sequence encoding said epitopes, or a vector, a plasmid, a recombinant virus or host cell comprising the polynucleotide as described herein, for use in the prevention and/or treatment an HPV infection and/or HPV related disease.

In a further embodiment, the present invention relates to the use of the polynucleotide, the vector, the host cell, the polypeptide or the composition for inducing an immune response against HPV in an individual. Said use can be characterized in that said polynucleotide, vector, host cell, polypeptide or composition is used as part of a series of time and compounds. In this regard, it is to be understood that the term "a series of time and compounds" refers to administering with time intervals to an individual the compounds used for eliciting an immune response. The latter compounds may comprise any of the following components: polynucleotide, vector, host cell, polypeptide or composition of the present invention.

The polyepitope construct of this invention can be provided in kit form together with instructions for vaccine administration. Typically the kit would include desired polynucleotide compositions in a container, preferably in unit dosage form and instructions for administration. An alternative kit would include a polynucleotide construct with desired nucleic acids of the invention in a container, preferably in unit dosage form together with instructions for administration. Lymphokines such as IL-2 or IL-12 may also be included in the kit. Other kit components that may also be desirable include, for example, a sterile syringe, booster dosages, and other desired excipients.

Other arrangements of the methods and tools embodying the invention will be obvious for those skilled in the art.

It is to be understood that although preferred embodiments, specific constructions and configurations, as well as materials, have been discussed herein for the methods and tools according to the present invention, various changes or modifications in form and detail may be made without departing from the scope and spirit of this invention.

TABLE 1

HPV derived CTL epitopes

| WT or analoged epitope sequence | SEQ ID NO | source | WT sequence | HLA |
|---|---|---|---|---|
| LSQMVQWAY | 1 | HPV16/31.E1.357 | | A01 |
| QVDYYGLYY | 2 | HPV16.E2.151 | | A01 |
| STDLRDHIDY | 3 | HPV16.E2.23 | | A01 |
| KSAIVTLTY | 4 | HPV16.E2.329 | | A01 |
| ISDYRHYCY | 5 | HPV16.E6.80.D3 | ISEYRHYCY | A01 |
| CLYLHIQSL | 6 | HPV16.E1.259 | | A02 |
| KLLSKLLCV | 7 | HPV16.E1.292 | | A02 |
| FVYIPLFLI | 8 | HPV16.E5.66 | | A02 |
| TLHDIILECV | 9 | HPV16.E6.29.L2 | TIHDIILECV | A02 |
| YMLDLQPETV | 10 | HPV16.E7.11.V10 | YMLDLQPETT | A02 |
| GTLGIVCPV | 11 | HPV16.E7.85.V9 | GTLGIVCPI | A02 |
| VVLLLVRYK | 12 | HPV16.E1.274 | | A11 |
| STAAALYWYK | 13 | HPV16.E1.314 | | A11 |
| ATMCRHYKR | 14 | HPV16.E1.406 | | A11 |
| KSLFGMSLMK | 15 | HPV16.E1.483 | | A11 |
| SVICFVNSK | 16 | HPV16.E1.497 | | A11 |
| AATKYPLLK | 17 | HPV16.E4.9 | | A11 |
| LYGVSFSEL | 18 | HPV16.E1.214 | | A24 |
| RFHNIRGRF | 19 | HPV16.E6.131.F9 | RFHNIRGRW | A24 |
| VYDFAFRDLCI | 20 | HPV16.E6.49 | | A24 |
| PYAVCDKCF | 21 | HPV16.E6.66.F9 | PYAVCDKCL | A24 |
| CYSLYGTTF | 22 | HPV16.E6.87.F9 | CYSLYGTTL | A24 |
| GTGCNGWFY | 23 | HPV18/31.E1.11 | | A01 |
| LQDKIIDHY | 24 | HPV18.E2.15 | | A01 |
| ATCVSHRGLY | 25 | HPV18.E2.154 | | A01 |
| TLEKLTNTGLY | 26 | HPV18.E6.89 | | A01 |
| ILYAHIQCL | 27 | HPV18.E1.266 | | A02 |
| VAWDSVYYM | 28 | HPV18.E2.136 | | A02 |
| TVYVFCFLL | 29 | HPV18.E5.51 | | A02 |
| SLQDIEITCV | 30 | HPV18.E6.24 | | A02 |
| KLTNTGLYNV | 31 | HPV18.E6.92.V10 | KLTNTGLYNL | A02 |
| KQGAMLAVFK | 32 | HPV18.E1.210 | | A11 |
| TVSATQLVK | 33 | HPV18.E2.211 | | A11 |
| STVSVGTAK | 34 | HPV18.E2.230 | | A11 |
| QVVPAYNISK | 35 | HPV18.E2.61 | | A11 |

TABLE 1-continued

HPV derived CTL epitopes

| WT or analoged epitope sequence | SEQ ID NO | source | WT sequence | HLA |
|---|---|---|---|---|
| FVVYRDSIPK | 36 | HPV18.E6.53.K10 | FVVYRDSIPH | A11 |
| DSVYGDTLER | 37 | HPV18.E6.83.R10 | DSVYGDTLEK | A11 |
| ATLQDIVLH | 38 | HPV18.E7.6 | | A11 |
| SYFGMSFIHF | 39 | HPV18/45.E1.491 | | A24 |
| YYMTDAGTW | 40 | HPV18.E2.142 | | A24 |
| GYNTFYIEF | 41 | HPV18.E2.168 | | A24 |
| MYVCCHVPL | 42 | HPV18.E5.14 | | A24 |
| VYVFCFLLPM | 43 | HPV18.E5.52 | | A24 |
| LYNLLIRCF | 44 | HPV18.E6.98.F9 | LYNLLIRCL | A24 |
| VMDDSEIAY | 45 | HPV31.E1.349 | | A01 |
| LSSALEIPY | 46 | HPV31.E6.15 | | A01 |
| AFTDLTIVY | 47 | HPV31.E6.46 | | A01 |
| QTEPDTSNY | 48 | HPV31.E7.44.T2 | QAEPDTSNY | A01 |
| KLLEKLLCI | 49 | HPV31.E1.272 | | A02 |
| YTNWKFIYL | 50 | HPV31.E2.131 | | A02 |
| FLLCFCVLL | 51 | HPV31.E5.15 | | A02 |
| FIYIPLFVI | 52 | HPV31.E5.66 | | A02 |
| FLFTDLTIV | 53 | HPV31.E6.45.L2 | FAFTDLTIV | A02 |
| KLTNKGICDL | 54 | HPV31.E6.90 | | A02 |
| MVMLMLVRFK | 55 | HPV31.E1.253 | | A11 |
| STAAALYWYR | 56 | HPV31.E1.294 | | A11 |
| ISFAGIVTK | 57 | HPV31.E2.205 | | A11 |
| ATTPIIHLK | 58 | HPV31.E2.291 | | A11 |
| KVSEFRWYRY | 59 | HPV31.E6.72 | | A11 |
| SVYGTTLER | 60 | HPV31.E6.82.R9 | SVYGTTLEK | A11 |
| PYLHSRLVVF | 61 | HPV31.E1.557 | | A24 |
| VFTFPNPFPF | 62 | HPV31.E1.565 | | A24 |
| HYTNWKFIF | 63 | HPV31.E2.130.F9 | HYTNWKFIY | A24 |
| VVFIYIPLF | 64 | HPV31.E5.64 | | A24 |
| FYSKVSEFRW | 65 | HPV31.E6.69 | | A24 |
| VYGTTLEKL | 66 | HPV31.E6.83 | | A24 |
| LQDKILDHY | 67 | HPV45.E2.17 | | A01 |
| NTGILTVTY | 68 | HPV45.E2.332 | | A01 |
| LTDVSIACVY | 69 | HPV45.E6.25.T2 | LQDVSIACVY | A01 |
| NTELYNLLI | 70 | HPV45.E6.95 | | A01 |
| ELDPVDLLCY | 71 | HPV45.E7.20 | | A01 |
| TLYAHIQCL | 72 | HPV45.E1.252 | | A02 |
| YVVWDSIYYI | 73 | HPV45.E2.137 | | A02 |
| SLVFLLCFSV | 74 | HPV45.E5.3 | | A02 |
| FLLCFSVCL | 75 | HPV45.E5.6 | | A02 |
| YQFAFKDLCV | 76 | HPV45.E6.45.V10 | YQFAFKDLCI | A02 |
| TLQEIVLHV | 77 | HPV45.E7.7.V9 | TLQEIVLHL | A02 |
| AVMCRHYKR | 78 | HPV45.E1.399 | | A11 |
| RQMNMSQWIK | 79 | HPV45.E1.411 | | A11 |
| STWHWTGCNK | 80 | HPV45.E2.322 | | A11 |
| VTTRYPLLR | 81 | HPV45.E4.8 | | A11 |
| RTEVYQFAFR | 82 | HPV45.E6.41.R10 | RTEVYQFAFK | A11 |
| SVYGETLEK | 83 | HPV45.E6.84 | | A11 |
| VFTFPHAFPF | 84 | HPV45.E1.578 | | A24 |
| YYITETGIW | 85 | HPV45.E2.144 | | A24 |
| VYVCAFAWLL | 86 | HPV45.E5.26 | | A24 |
| VYQFAFKDL | 87 | HPV45.E6.44 | | A24 |
| FYSRIRELRF | 88 | HPV45.E6.71.F10 | FYSRIRELRY | A24 |

Column 1 contains the analoged epitope when no WT sequence is indicated in column 4.

TABLE 2

HPV HTL epitopes

| Epitope sequence | source | SEQ ID NO |
|---|---|---|
| LYWYKTGISNISEVY | HPV16.E1.319 | 89 |
| PEWIQRQTVLQHSFN | HPV16.E1.337 | 90 |
| WKHMRLECAIYYKAR | HPV16.E2.033 | 91 |
| LQAIELQLTLETIYN | HPV16.E2.070 | 92 |
| GLYYVHEGIRTYFVQ | HPV16.E2.156 | 93 |
| QRFHNIRGRWTGRCM | HPV16.E6.130 | 94 |
| LDLQPETTDLYCYEQ | HPV16.E7.13 | 95 |
| LCTELQTTIHDIILE | HPV16.E6.22 | 96 |
| IRTLEDLLMGTLGIV | HPV16.E7.76 | 97 |
| FKTLIQPFILYAHIQ | HPV18.E1.258 | 98 |
| IEFITFLGALKSFLK | HPV18.E1.458 | 99 |
| FLNTVAIPDSVQILV | HPV18.E2.346 | 100 |
| HKAIELQMALQGLAQ | HPV18.E2.074 | 101 |
| EVFEFAFKDLFVVYR | HPV18.E6.43 | 102 |

TABLE 2-continued

HPV HTL epitopes

| Epitope sequence | source | SEQ ID NO |
|---|---|---|
| LFVVYRDSIPHAACHK | HPV18.E6.52 | 103 |
| TNTGLYNLLIRCLRCQ | HPV18.E6.94 | 104 |
| FQQLFLNTLSFVCPW | HPV18.E7.86 | 105 |
| NGWFYVEAVIDRQTG | HPV31.E1.15 | 106 |
| PEWIERQTVLQHSFN | HPV31.E1.317 | 107 |
| WKHIRLECVLMYKAR | HPV31.E2.033 | 108 |
| TTPIIHLKGDANILK | HPV31.E2.292 | 109 |
| TGRCIACWRRPRTET | HPV31.E6.132 | 110 |
| VLDFAFTDLTIVYRD | HPV31.E6.42 | 111 |
| IRILQELLMGSFGIV | HPV31.E7.76 | 112 |
| PRKLHELSSALEIPY | HPV31.E6.9 | 113 |
| DWVMAIFGVNPTVAEGF | HPV45.E1.228 | 114 |
| FKTLIKPATLYAHIQ | HPV45.E1.244 | 115 |
| PINISKSKAHKAIEL | HPV45.E2.67 | 116 |
| TIPNSVQISVGYMTI | HPV45.E2.354 | 117 |
| LCIVYRDCIAYAACH | HPV45.E6.52 | 118 |
| FHSIAGQYRGQCNTC | HPV45.E6.127 | 119 |
| EIVLHLEPQNELDPV | HPV45.E7.10 | 120 |
| LRTLQQLFLSTLSFV | HPV45.E7.84 | 121 |
| AKFVAAWTLKAAA | PADRE | 122 |

The present invention is illustrated by the following Examples, which should not be understood to limit the scope of the invention to the specific embodiments therein.

EXAMPLES

Example 1

HLA Class I Competition Binding Assays Using Soluble HLA

The following example of peptide binding to soluble HLA molecules demonstrates quantification of binding affinities of HLA class I and class II peptides.

Epstein-Barr virus (EBV)-transformed homozygous cell lines, fibroblasts or transfectants were used as sources of HLA class I molecules. Cell lysates were prepared and HLA molecules purified in accordance with disclosed protocols (Sidney et al., 1998; Sidney et al., 1995; Sette, et al., 1994).

HLA molecules were purified from lysates by affinity chromatography. The lysate was passed over a column of Sepharose CL-4B beads coupled to an appropriate antibody. The antibodies used for the extraction of HLA from cell lysates are W6/32 (for HLA-A), and LB3.1 (for HLA-DR).

The anti-HLA column was then washed with 10 mM Tris-HCL, pH8, in 1% NP-40, PBS, and PBS containing 0.4% n-octylglucoside and HLA molecules were eluted with 50 mM diethylamine in 0.15M NaCl containing 0.4% n-octylglucoside, pH 11.5. A 1/25 volume of 2M Tris, pH6.8, was added to the eluate to reduce the pH to +/−pH8. Eluates were then concentrated by centrifugation in Centriprep 30 concentrators (Amicon, Beverly, Mass.). Protein content was evaluated by a BCA protein assay (Pierce Chemical Co., Rockford, Ill.) and confirmed by SDS-PAGE.

A detailed description of the protocol utilized to measure the binding of peptides to Class I and Class II MHC has been published (Sette et al., 1994; Sidney et al., 1998). Briefly, purified MHC molecules (5 to 500 nM) were incubated with various unlabeled peptide inhibitors and 1-10 nM 125I-radiolabeled probe peptides for 48 h in PBS containing 0.05% Nonidet P-40 (NP40) in the presence of a protease inhibitor cocktail. All assays were at pH7 with the exception of DRB1*0301, which was performed at pH4.5, and DRB1*1601 (DR2w21 1) and DRB4*0101 (DRw53), which were performed at pH5.

Following incubation, MHC-peptide complexes were separated from free peptide by gel filtration on 7.8 mm×15 cm TSK200 columns (TosoHaas 16215, Montgomeryville, Pa.). The eluate from the TSK columns was passed through a Beckman 170 radioisotope detector, and radioactivity was plotted and integrated using a Hewlett-Packard 3396A integrator, and the fraction of peptide bound was determined. Alternatively, MHC-peptide complexes were separated from free peptide by capturing onto ELISA plates coated with anti-HLA antibodies. After free peptide has been washed away, remaining reactivities were measured using the same method as above.

Radio labeled peptides were iodinated using the chloramine-T method.

Typically, in preliminary experiments, each MHC preparation was titered in the presence of fixed amounts of radiolabeled peptides to determine the concentration of HLA molecules necessary to bind 10-20% of the total radioactivity. All subsequent inhibition and direct binding assays were performed using these HLA concentrations.

Since under these conditions [label]<[HLA] and IC50≥ [HLA], the measured IC50 values are reasonable approximations of the true KD values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the IC50 of a positive control for inhibition by the IC50 for each tested peptide (typically unlabeled versions of the radiolabeled probe peptide). For database purposes, and inter-experiment comparisons, relative binding values are compiled. These values can subsequently be converted back into IC50 nM values by dividing the IC50 nM of the positive controls for inhibition by the relative binding of the peptide of interest. This method of data compilation has proven to be the most accurate and consistent for comparing peptides that have been tested on different days, or with different lots of purified MHC. Table 3-6 contain the IC 50 values for the CTL epitopes.

Because the antibody used for HLA-DR purification (LB3.1) is alpha-chain specific, beta-1 molecules are not separated from beta-3 (and/or beta-4 and beta-5) molecules. The beta-1 specificity of the binding assay is obvious in the cases of DRB1*0101 (DR1), DRB1*0802 (DR8w2), and DRB1*0803 (DR8w3), where no beta-3 is expressed. It has also been demonstrated for DRB1*0301 (DR3) and DRB3*0101 (DR52a), DRB1*0401 (DR4w4), DRB1*0404 (DR4w14), DRB1*0405 (DR4w15), DRB1*1101 (DR5), DRB1*1201 (DR5w12), DRB1*1302 (DR6w19) and DRB1*0701 (DR7). The problem of beta chain specificity for DRB1*1501 (DR2w2beta-1), DRB5*0101 (DR2w2beta-2), DRB1*1601 (DR2w21beta-1), DRB5*0201 (DR51Dw21), and DRB4*0101 (DRw53) assays is circumvented by the use of fibroblasts. Development and validation of assays with regard to DRbeta molecule specificity have been described previously (see, e.g., Southwood et al., 1998). Table 7 contains the IC50 values for the HTL epitopes.

TABLE 3

Binding of HLA A01-restricted peptides

| SEQ ID | Sequence | source | HLA A0101 (nM) | A2601 (nM) | A2902 (nM) | A3002 (nM) |
|---|---|---|---|---|---|---|
| 23 | GTGCNGWFY | HPV18/31.E1.11 | 136 | 3081 | 116 | 9.1 |
| 24 | LQDKIIDHY | HPV18.E2.15 | 68 | — | — | 2770 |
| 25 | ATCVSHRGLY | HPV18.E2.154 | 421 | 646 | 4212 | 28 |
| 26 | TLEKLTNTGLY | HPV18.E6.89 | 174 | 265 | 2378 | 476 |
| 2 | QVDYYGLYY | HPV16.E2.151 | 2.7 | 251 | 25 | 160 |
| 3 | STDLRDHIDY | HPV16.E2.23 | 113 | 758 | — | 17 |
| 4 | KSAIVTLTY | HPV16.E2.329 | 9 | — | 96 | 6 |
| 5 | ISDYRHYCY | HPV16.E6.80.D3 | 10 | — | 10 | 192 |
| 1 | LSQMVQWAY | HPV16/31.E1.357 | 21 | 6448 | 122 | 0.93 |
| 45 | VMDDSEIAY | HPV31.E1.349 | 18 | — | 95 | 2551 |
| 46 | LSSALEIPY | HPV31.E6.15 | 35 | 4107 | 261 | 175 |
| 47 | AFTDLTIVY | HPV31.E6.46 | 31 | | 36 | 71 |
| 48 | QTEPDTSNY | HPV31.E7.44.T2 | 19 | — | — | 2322 |
| 67 | LQDKILDHY | HPV45.E2.17 | 32 | 5000 | — | 836 |
| 68 | NTGILTVTY | HPV45.E2.332 | 337 | 3147 | 1403 | 8722 |
| 69 | LTDVSIACVY | HPV45.E6.25.T2 | 2.9 | 8201 | 764 | 72 |
| 70 | NTELYNLLI | HPV45.E6.95 | 32 | 17294 | — | — |
| 71 | ELDPVDLLCY | HPV45.E7.20 | 26 | 2107 | 4291 | — |

—: IC50 > 20 μM
Empty field: no data available

TABLE 4

Binding of HLA A02-restricted peptides

| SEQ ID | Sequence | Source | HLA A0201 (nM) | A0202 (nM) | A0203 (nM) | A0206 (nM) | A6802 (nM) |
|---|---|---|---|---|---|---|---|
| 27 | ILYAHIQCL | HPV18.E1.266 | 33 | 8.5 | 10.2 | 236 | — |
| 28 | VAWDSVYYM | HPV18.E2.136 | 172 | 603 | 1332 | 790 | 5154 |
| 29 | TVYVFCFLL | HPV18.E5.51 | 175 | 587 | 769 | 26 | 41 |
| 30 | SLQDIEITCV | HPV18.E6.24 | 153 | 25 | 38 | 205 | — |
| 31 | KLTNTGLYNV | HPV18.E6.92.V10 | 106 | 2.9 | 4.7 | 83 | 688 |
| 6 | CLYLHIQSL | HPV16.E1.259 | 73 | 45 | 21 | 100 | 1777 |
| 7 | KLLSKLLCV | HPV16.E1.292 | 31 | 67.7 | 23 | 124.6 | — |
| 8 | FVYIPLFLI | HPV16.E5.66 | 206 | 323 | 63 | 59 | 251 |

TABLE 4-continued

Binding of HLA A02-restricted peptides

| SEQ ID | Sequence | Source | HLA A0201 (nM) | A0202 (nM) | A0203 (nM) | A0206 (nM) | A6802 (nM) |
|---|---|---|---|---|---|---|---|
| 9 | TLHDIILECV | HPV16.E6.29.L2 | 3.6 | 0.54 | 1.9 | 92 | 2947 |
| 10 | YMLDLQPETV | HPV16.E7.11.V10 | 19 | 1.9 | 4.5 | 86 | 5446 |
| 11 | GTLGIVCPV | HPV16.E7.85.V9 | 20 | 49 | 68 | 33 | 32 |
| 49 | KLLEKLLCI | HPV31.E1.272 | 19 | 21 | 2.4 | 51 | — |
| 50 | YTNWKFIYL | HPV31.E2.131 | 69 | 14 | 31 | 84 | 146 |
| 51 | FLLCFCVLL | HPV31.E5.15 | 9.6 | 13 | 34 | 2.6 | 237 |
| 52 | FIYIPLFVI | HPV31.E5.66 | 26 | 97 | 47 | 8.1 | 157 |
| 53 | FLFTDLTIV | HPV31.E6.45.L2 | 17 | 1.3 | 3.5 | 20 | 1904 |
| 54 | KLTNKGICDL | HPV31.E6.90 | 205 | 440 | 585 | 484 | — |
| 72 | TLYAHIQCL | HPV45.E1.252 | 34 | 4.9 | 6.2 | 417 | 1613 |
| 73 | YVVWDSIYYI | HPV45.E2.137 | 77 | 27 | 248 | 20 | 30 |
| 74 | SLVFLLCFSV | HPV45.E5.3 | 8.5 | 27 | 49 | 7.9 | 20 |
| 75 | FLLCFSVCL | HPV45.E5.6 | 38 | 81 | 66 | 59 | 353 |
| 76 | YQFAFKDLCV | HPV45.E6.45.V10 | 15 | 1.3 | 4.2 | 10 | 3698 |
| 77 | TLQEIVLHV | HPV45.E7.7.V9 | 19 | 30 | 5.1 | 309 | 2457 |

—: IC50 > 20 μM

TABLE 5

Binding of HLA A11-restricted peptides

| SEQ ID | Sequence | Source | HLA A0301 (nM) | A1101 (nM) | A3101 (nM) | A3301 (nM) | A6801 (nM) |
|---|---|---|---|---|---|---|---|
| 32 | KQGAMLAVFK | HPV18.E1.210 | 35 | 11 | 519 | — | 235 |
| 33 | TVSATQLVK | HPV18.E2.211 | 7 | 4 | 6137 | — | 31 |
| 34 | STVSVGTAK | HPV18.E2.230 | 34 | 6 | 1760 | — | 10 |
| 35 | QVVPAYNISK | HPV18.E2.61 | 308 | 14 | 6665 | — | 8 |
| 36 | FVVYRDSIPK | HPV18.E6.53.K10 | 3437 | 2504 | 8 | 473 | 176 |
| 37 | DSVYGDTLER | HPV18.E6.83.R10 | 193 | 73 | 246 | 1425 | 44 |
| 38 | ATLQDIVLH | HPV18.E7.6 | 211 | 11 | 543 | — | — |
| 12 | WLLLVRYK | HPV16.E1.274 | 6.3 | 4.1 | 0.1 | 6.1 | 76 |
| 13 | STAAALYWYK | HPV16.E1.314 | 5 | 2 | 35 | 128 | 6 |
| 14 | ATMCRHYKR | HPV16.E1.406 | 90 | 14 | 10 | 17 | 35 |
| 15 | KSLFGMSLMK | HPV16.E1.483 | 3.9 | 2 | 230 | — | 887 |
| 16 | SVICFVNSK | HPV16.E1.497 | 109 | 2.2 | 25 | 51 | 5.4 |
| 17 | AATKYPLLK | HPV16.E4.9 | 59 | 20 | — | — | — |
| 55 | MVMLMLVRFK | HPV31.E1.253 | 10 | 16 | 53 | 20 | 10 |
| 56 | STAAALYWYR | HPV31.E1.294 | 198 | 10 | 5.6 | 47 | 12 |

TABLE 5-continued

Binding of HLA A11-restricted peptides

| SEQ ID | Sequence | Source | HLA A0301 (nM) | A1101 (nM) | A3101 (nM) | A3301 (nM) | A6801 (nM) |
|---|---|---|---|---|---|---|---|
| 57 | ISFAGIVTK | HPV31.E2.205 | 17 | 1.6 | 115 | 4366 | 16 |
| 58 | ATTPIIHLK | HPV31.E2.291 | 10 | 1.2 | 34 | — | 2.5 |
| 59 | KVSEFRWYRY | HPV31.E6.72 | 213 | 25 | 3 | 338 | 192 |
| 60 | SVYGTTLER | HPV31.E6.82.R9 | 22 | 7 | 75 | 853 | 4 |
| 78 | AVMCRHYKR | HPV45.E1.399 | 311 | 38 | 52 | 24 | 29 |
| 79 | RQMNMSQWIK | HPV45.E1.411 | 15 | 11 | 45 | — | 2557 |
| 80 | STWHWTGCNK | HPV45.E2.322 | 14 | 2.8 | 54 | 428 | 18 |
| 81 | VTTRYPLLR | HPV45.E4.8 | 158 | 18 | 483 | — | 3147 |
| 82 | RTEVYQFAFR | HPV45.E6.41.R10 | 755 | 211 | 8 | 696 | 439 |
| 83 | SVYGETLEK | HPV45.E6.84 | 21 | 9.5 | 6506 | — | 7.2 |

—: IC50 > 20 μM

TABLE 6

Binding of HLA A24-restricted peptides

| SEQ ID | Sequence | Source | HLA A2302 (nM) | A2402 (nM) | A2902 (nM) | A3002 (nM) |
|---|---|---|---|---|---|---|
| 39 | SYFGMSFIHF | HPV18/45.E1.491 | 4.3 | 17.5 | 62 | 1544 |
| 40 | YYMTDAGTW | HPV18.E2.142 | 14 | 3.2 | 3411 | 2151 |
| 41 | GYNTFYIEF | HPV18.E2.168 | 13 | 16 | 835 | 1264 |
| 42 | MYVCCHVPL | HPV18.E5.14 | 24 | 15 | 9442 | 4717 |
| 43 | VYVFCFLLPM | HPV18.E5.52 | 57 | 178 | 5276 | — |
| 44 | LYNLLIRCF | HPV18.E6.98.F9 | 10 | 32 | — | 2255 |
| 18 | LYGVSFSEL | HPV16.E1.214 | 7.2 | 3.1 | — | — |
| 19 | RFHNIRGRF | HPV16.E6.131.F9 | 2.4 | 29 | 346 | 0.69 |
| 20 | VYDFAFRDLCI | HPV16.E6.49 | 8.9 | 22 | — | — |
| 21 | PYAVCDKCF | HPV16.E6.66.F9 | 6.1 | 7.2 | 641 | 157 |
| 22 | CYSLYGTTF | HPV16.E6.87.F9 | 11 | 28 | 2088 | 7823 |
| 61 | PYLHSRLVVF | HPV31.E1.557 | 2.8 | 38.7 | 4365 | 2229 |
| 62 | VFTFPNPFPF | HPV31.E1.565 | 12 | 17 | 603 | — |
| 63 | HYTNWKFIF | HPV31.E2.130.F9 | 16 | 8.5 | 433 | 4847 |
| 64 | VVFIYIPLF | HPV31.E5.64 | 108 | 276 | 302 | 268 |
| 65 | FYSKVSEFRW | HPV31.E6.69 | 8.8 | 4.5 | 1777 | 1361 |
| 66 | VYGTTLEKL | HPV31.E6.83 | 8.2 | 26 | — | 1237 |
| 84 | VFTFPHAFPF | HPV45.E1.578 | 15.9 | 90.4 | 57 | — |
| 85 | YYITETGIW | HPV45.E2.144 | 2 | 8.5 | — | — |

TABLE 6-continued

Binding of HLA A24-restricted peptides

| SEQ ID | Sequence | Source | HLA A2302 (nM) | A2402 (nM) | A2902 (nM) | A3002 (nM) |
|---|---|---|---|---|---|---|
| 86 | VYVCAFAWLL | HPV45.E5.26 | 8.1 | 8.4 | 2346 | — |
| 87 | VYQFAFKDL | HPV45.E6.44 | 1.1 | 4 | — | 165 |
| 88 | FYSRIRELRF | HPV45.E6.71.F10 | 1 | 3.2 | 83 | — |

—: IC50 > 20 μM

TABLE 7

Binding data of HTL epitopes

| SEQ ID | Sequence | Source | IC$_{50}$ nM to purified HLA | | | | | | |
|---|---|---|---|---|---|---|---|---|---|
| | | | DRB1 *0101 | DRB1 *0301 | DRB1 *0401 | DRB1 *0404 | DRB1 *0405 | DRB1 *0701 | DRB1 *0802 |
| 89 | LYWYKTGISNISEVY | HPV16.E1.319 | 13 | 12.000 | 6.2 | 3543 | 96 | 25 | 2965 |
| 90 | PEWIQRQTVLQHSFN | HPV16.E1.337 | 2086 | 11.052 | 14 | 21 | 101 | — | 137 |
| 91 | WKHMRLECAIYYKAR | HPV16.E2.033 | 701 | 437 | 245 | 6858 | 557 | 504 | 90 |
| 95 | LQAIELQLTLETIYN(2) | HPV16.E2.070 | 42 | 534 | 37 | 282 | 384 | 3280 | 7612 |
| 93 | GLYYVHEGIRTYFVQ | HPV16.E2.156 | 67 | 17.706 | 322 | — | 1870 | 55 | 3143 |
| 94 | QRFHNIRGRWTGRCM | HPV16.E6.130 | 36 | — | 2897 | 4110 | 4469 | 277 | 894 |
| 95 | LDLQPETTDLYCYEQ | HPV16.E7.13 | — | 590 | 1904 | — | — | — | — |
| 96 | LCTELQTTIHDIILE | HPV16.E6.22 | 2714 | 80 | 3662 | 7966 | | | — |
| 97 | IRTLEDLLMGTLGIV | HPV16.E7.76 | 142 | 449 | 677 | 277 | 2008 | 4018 | — |
| 98 | FKTLIQPFILYAHIQ | HPV18.E1.258 | 54 | — | 949 | 111 | 3255 | 1690 | 6006 |
| 99 | IEFITFLGALKSFLK | HPV18.E1.458 | 30 | — | 108 | 32 | 3645 | — | 11.001 |
| 100 | FLNTVAIPDSVQILV | HPV18.E2.346 | 718 | 68 | 209 | 555 | 616 | 15 | — |
| 101 | HKAIELQMALQGLAQ | HPV18.E2.074 | 41 | 5648 | 50 | 27 | — | — | 811 |
| 105 | FQQLFLNTLSFVCPW | HPV18.E7.86 | 204 | 6522 | 139 | 496 | 376 | 237 | 8996 |
| 106 | LFVVYRDSIPHAACHK(1) | HPV18.E6.52 | 356 | 73 | 4.7 | 28 | 2159 | 2600 | 108 |
| 102 | EVFEFAFKDLFVVYR | HPV18.E6.43 | 2865 | 73 | 347 | 553 | 1320 | 14.415 | 1415 |
| 107 | TNTGLYNLLIRCLRCQ(1) | HPV18.E6.94 | 367 | 9439 | 1485 | 62 | 406 | 4038 | 41 |
| 106 | NGWFYVEAVIDRQTG | HPV31.E1.15 | 1859 | 2797 | 845 | 18.761 | 178 | 1459 | — |
| 107 | PEWIERQTVLQHSFN | HPV31.E1.317 | 5969 | 3857 | 35 | 23 | 127 | — | 954 |
| 108 | WKHIRLECVLMYKAR | HPV31.E2.033 | 1444 | 146 | 263 | 307 | 71 | 16449 | 476 |
| 109 | TTPIIHLKGDANILK | HPV31.E2.292 | 168 | 74 | 8823 | 627 | 19514 | 3714 | 4480 |
| 112 | IRILQELLMGSFGIV | HPV31.E7.76 | 50 | 5376 | 361 | 143 | 3068 | 267 | 7543 |
| 111 | VLDFAFTDLTIVYRD | HPV31.E6.42 | 7561 | 30 | 938 | 3309 | 2839 | 209 | 14.078 |
| 110 | TGRCIACWRRPRTET | HPV31.E6.132 | 3167 | 1033 | 758 | 1146 | 733 | 11.460 | 512 |
| 113 | PRKLHELSSALEIPY | HPV31.E6.9 | 183 | 1435 | 1557 | 117 | 32 | 62 | 17.333 |
| 114 | DWVMAIFGVNPTVAEGF | HPV45.E1.228 | 487 | 3749 | 91 | 20 | 92 | 52 | 4265 |
| 115 | FKTLIKPATLYAHIQ | HPV45.E1.244 | 269 | 5197 | 316 | 111 | 2234 | 148 | 11 |

TABLE 7-continued

Binding data of HTL epitopes

| | | | | | | | | | |
|---|---|---|---|---|---|---|---|---|---|
| 116 | PINISKSKAHKAIEL | HPV45.E2.67 | 122 | 1.068 | 255 | 97 | 1912 | 17 | 3172 |
| 117 | TIPNSVQISVGYMTI | HPV45.E2.354 | 52 | 483 | 515 | 18 | 196 | 9 | 6226 |
| 118 | LCIVYRDCIAYAACH | HPV45.E6.52 | 402 | 904 | 481 | 1043 | 702 | 1080 | 1104 |
| 119 | FHSIAGQYRGQCNTC | HPV45.E6.127 | 107 | — | 8.6 | 3305 | 358 | 2403 | 7644 |
| 120 | EIVLHLEPQNELDPV | HPV45.E7.10 | 967 | 354 | 12.052 | 947 | 273 | 3490 | — |
| 121 | LRTLQQLFLSTLSFV | HPV45.E7.84 | 41 | 3388 | 127 | 19 | 106 | 39 | 4101 |

| | IC$_{50}$ nM to purified HLA | | | | | | | | No. |
|---|---|---|---|---|---|---|---|---|---|
| SEQ ID | DRB1 *0901 | DRB1 *1101 | DRB1 *1201 | DRB1 *1302 | DRB1 *1501 | DRB3 *0101 | DRB4 *0101 | DRB5 *0101 | alleles bound |
| 89 | 90 | 2757 | | 938 | 1754 | | 19.572 | 588 | 7 |
| 90 | 3181 | 117 | | 662 | 9450 | | 4.3 | 1528 | 7 |
| 91 | 6335 | 2401 | | 248 | 1393 | | 766 | 280 | 9 |
| 95 | 1433 | 4378 | 268 | 17 | 688 | | 2 | — | 9 |
| 93 | 431 | 5331 | | — | 156 | | — | 1000 | 6 |
| 94 | — | 574 | 14.595 | 4308 | 17.214 | — | 4553 | 919 | 5 |
| 95 | — | — | — | — | — | — | 17 | — | 2 |
| 96 | — | — | — | 5529 | — | — | 1044 | — | 1 |
| 97 | — | — | 950 | 1548 | 10.272 | 4236 | 923 | — | 6 |
| 98 | 1226 | 6695 | | 4286 | 7.9 | | 317 | 11.878 | 5 |
| 99 | — | 1613 | | — | 49 | | 1229 | 664 | 5 |
| 100 | 534 | — | | 90 | 8957 | 91 | 446 | — | 10 |
| 101 | 12.764 | 844 | | 3536 | 573 | | 3 | 126 | 8 |
| 105 | 1325 | 6522 | | 11 | 555 | | 586 | 17.298 | 8 |
| 106 | 8598 | 786 | | 566 | 64 | | 15.242 | 3770 | 8 |
| 102 | — | 6079 | 624 | 165 | 1522 | — | 316 | — | 6 |
| 107 | 13.620 | 17 | 4057 | 719 | 36 | 19.877 | 366 | 3656 | 8 |
| 106 | 3670 | — | | — | — | | 627 | 1203 | 3 |
| 107 | 1707 | 535 | | 2855 | 13.492 | | 23 | 6231 | 6 |
| 108 | 11831 | 81 | | 54 | 134 | | 102 | 412 | 10 |
| 109 | 17365 | 7331 | | 527 | 205 | 4755 | 49 | — | 6 |
| 112 | 141 | 4037 | | 398 | 94 | | 24 | 5383 | 8 |
| 111 | 790 | 13.000 | NT | 753 | 2622 | NT | 307 | — | 6 |
| 110 | 13.556 | 158 | 4949 | 2771 | 84 | 5961 | 225 | 6047 | 6 |
| 113 | 342 | 2126 | | 59 | 299 | | 835 | 13.207 | 8 |
| 114 | 17945 | 4957 | | 68 | 108 | | 571 | 387 | 9 |
| 115 | 8103 | 24 | | 164 | 195 | | 69 | 1004 | 9 |
| 116 | 170 | 327 | | 309 | 231 | — | 1724 | 452 | 9 |
| 117 | 91 | 487 | | 14 | 10 | 10775 | 16 | 8328 | 11 |

TABLE 7-continued

Binding data of HTL epitopes

| | | | | | | | | | |
|---|---|---|---|---|---|---|---|---|---|
| 118 | 2150 | 1867 | | 965 | 262 | | 1525 | 673 | 7 |
| 119 | 1992 | 416 | 10.126 | — | 574 | — | 1296 | 43 | 6 |
| 120 | — | — | — | 5352 | — | — | 713 | — | 5 |
| 121 | 394 | 1675 | | 33 | 17 | | 21 | 1254 | 9 |

(1) binding data shown for the 15-mer (1AA less at the carboxy-terminus)
(2) binding data for crude peptide batch

Example 2

Polyepitope Construct Design

Each designed DNA construct contains HLA-restricted epitopes which bind to at least one HLA molecule with an affinity <500 nM and preferably less than 100 nM (tables 3-6 in Example 1). Most of these epitopes were demonstrated to be immunogenic in the respective HLA transgenic mice when administered as a pool of peptides emulsified in IFA (tables 8-9 in Example 3).

The epitope order and amino acid spacers in the constructs were designed to avoid generation of junctional epitopes and to maximize proteosomal processing. The amino acid sequences were back-translated using a mammalian codon usage table and the on-line back-translation tool both provided by Entelechon (Germany). The DNA sequences were inserted into pMB75.6 vector using PstI and BamHI restriction sites. A Kozak sequence, a mouse Igkappa signal sequence (MGMQVQIQSLFLLLLWVPGSRG, SEQ ID NO 131), and a stop codon were also included. The respective amino acid and DNA sequences of the constructs ICCG6137, ICCG6138, ICCG6149 and ICCG6150 are given in FIGS. 5-8.

Example 3

Immunogenicity of HPV-Derived HLA-Class I-Restricted Epitopes Encoded in a HPV DNA Polyepitope Construct The immunogenicity of HPV HLA class I-restricted epitopes encoded in the DNA constructs was tested in the relevant HLA transgenic mice. The evaluation of the immunogenicity of HPV-derived HLA-A02-, HLA-A11- and HLA-A24 and HLA-A01-restricted epitopes encoded in different DNA constructs was done using the following protocol. HLA transgenic mice (F1 HLA-A02/KbxBalb/c, HLA-A11/Kb, HLA A01/Kb and HLA-A24/Kb transgenic mice) were immunised with one of the selected DNA constructs. To ensure an equal distribution of mice between different groups, a randomisation procedure based on body weight was performed. Female and male mice (age between 8 and 24 weeks) were ranked by body weight, extreme light or heavy animals were excluded. The remaining animals were grouped by sequentially assigning animals for the 2 experiments.

DNA Immunization

Mice were pre-treated with cardiotoxin (Sigma, C9759) on day −4 by bilateral intramuscular injection of 100 μl (2×50 μl) of a 10 μM cardiotoxin solution. Four days later, all mice were immunised with 100 μg HPV-DNA plasmid (diluted to 1 mg/ml in PBS) by bilateral injection of 50 μg in the m. tibialis anterior. Mice were euthanised between 13 and 15 days after the DNA immunisation.

Peptide Immunization

Peptides were dissolved in DMSO at a concentration of 10 mg/mL. For each of the 4 DNA constructs, the corresponding HLA-restricted peptides were pooled per HLA type (5 to 7 CTL peptides/pool). A known HTL peptide (TPPAYRPP-NAPIL) was added and the peptide pools were diluted in PBS to the required peptide concentration (i.e. 25 μg of each CTL peptide and 120 μg HTL peptide in 50 μl). After adding an equal volume of IFA (Pierce, lot DG56079), the mixture was emulsified by forcing it through a small orifice. Mice were immunized subcutaneously at the base of the tail with 50 μl peptide/IFA mixture.

Immunization Scheme

From each line, 4 groups of 12 mice (HLA-A02 and HLA-A24) or 6 mice (HLA-A11) were immunized intramuscularly with one of the 4 HPV DNA constructs (ICCG6149, ICCG6150, ICCG6137, ICCG6138) respectively. For HLA A01, only 2 constructs were evaluated. To this, 2 groups of 12 mice were immunized intramuscularly with either ICCG6150 or ICCG6138. A final group of 12 mice was not DNA-immunized nor peptide-immunized and was included as a negative control (CT treatment only)

For the evaluation of the peptide immunogenicity, 4 groups of 12 mice (HLA-A01), 6 mice (HLA-A02 and HLA-A24) or 3 mice (HLA-A11) were injected subcutaneously with one of the HLA-restricted peptide pools in IFA. As negative control for the peptide-immunized mice, 18 mice (in total) were injected with a PBS/IFA mixture.

In Vitro Experimental Set-Up

Mice were euthanized and spleen cells (SPC) were isolated 13 days after immunization. SPC of DNA- and peptide-immunized HLA-A01/Kb, F1 HLA-A02/KbxBalb/c and HLA-A24/Kb mice were pooled per 2 mice, resulting in 6, 6 and 3 data points per condition, respectively. Spleen cells of DNA- and peptide-immunized HLA-A11/Kb mice were analyzed individually. SPC of all negative control mice were pooled per 2 mice, resulting in 3 data points for each peptide tested. CD8+ cells were purified by positive magnetic bead selection on SPC, using CD8a MicroBeads (MACS 130-049-401) according to the manufacturer's protocol.

A direct ex vivo IFNγ ELISPOT assay was used as surrogate CTL readout. Basically, purified CD8+ cells were incubated with the individual HPV-specific HLA-restricted peptides (10 μg/mL) loaded on the appropriate antigen presenting cells (APC), in anti-mouse IFNγ antibody-coated ELISPOT plates. Because of the limited availability, purified CD8+ cells of peptide-immunized HLA-A11/Kb mice were seeded in the coated ELISPOT plates at $10^5$ cells/well, whereas for all other treatment groups, $2×10^5$ CD8+ cells/well were used. After 20 h incubation, IFNγ-producing cells were visualized by further developing the plates with biotinylated anti-mouse IFNγ antibody, streptavidin-HRP and AEC as substrate. APC used for the different HLA-restricted peptides were spleen cells from non-immunized HLA-A01/Kb mice for HLA-A01, JA2.1 Kb cells (2×10⁴ cells/well) for HLA-A02, LCL 721.221HLA A11/Kb (10⁴ cells/well) for HLA-A11, and LCL 721.221HLA A24/Kb (10⁴ cells/well) for HLA-A24.

Some of the CTL epitopes included in the DNA constructs are analoged sequences of the wild type viral epitopes. For these particular epitopes, only the wild type sequences were used as in vitro stimulus for CTL readout. In addition, 3 HLA-A24-restricted sequence variant epitopes were used as in vitro stimulus to check for potential cross-variant reactivity. Baseline responses towards all HLA-restricted peptides used for in vitro readout were evaluated in naïve HLA-A01/Kb, F1 HLA-A02/KbxBalb/c, HLA-A11/Kb, or HLA-A24/Kb transgenic mice. No significant responses could be detected (results not shown).

Data Analysis

Peptides eliciting a specific delta CTL response of 30 specific spots/$10^6$ CD8 cells and a response ratio ≥2 in at least one pool are categorised as immunogenic. A minimum of 2 pools is to be tested.

Results

The results for the different HPV constructs are shown in table 8 and 9.

The majority of epitopes that bind with high affinity to the HLA (IC50 less than 500 nM and preferably less than 100 nM) are able to induce positive T cell responses in the respective HLA transgenic mice, indicating that HLA binding affinity is a proper selection criterion for identifying potential immunogenic epitopes. These immunogenic responses can be induced with the isolated peptides and/or with a plasmid DNA encoding these peptides.

TABLE 8

Immunogenicity data for HLA class-I-restricted HPV 16 and HPV 18 epitopes encoded in constructs ICCG 6149 and ICCG 6150

| | HLA-A01 | | | | | | | | |
|---|---|---|---|---|---|---|---|---|---|
| | Sequence of WT | ICCG6149 | | | ICCG6150 | | | Peptide Pool | |
| SEQ ID | peptide used for CTL read-out | Delta SFC/$10^6$ cells[b] | Ratio[b] | Immun Y/N | Delta SFC/$10^6$ cells[a] | Ratio[b] | Immun Y/N | Delta SFC/$10^6$ cells[b] | Ratio[b] | Immun Y/N |
| 1 | LSQMVQWAY | | | | 1 (1-10) | 0.7 (0.5-2.0) | N | 2 (1-13) | 1.3 (0.8-2.0) | N |
| 2 | QVDYYGLYY | | | | 12 (1-25) | 1.8 (0.8-2.5) | N | 20 (7-92) | 2.6 (1.5-15.0) | Y |
| 3 | STDLRDHIDY | | | | 1 (1-20) | 1.0 (0.8-3.0) | N | 1 (1-3) | 1.0 (0.6-1.5) | N |
| 4 | KSAIVTLTY | | | | 1 (1-85) | 1.0 (0.7-5.3) | Y | 68 (30-205) | 5.4 (3.0-30.5) | Y |
| 132 | ISEYRHYCY | | | | 3 (1-10) | 1.1 (0.4-2.0) | N | 2 (1-13) | 1.1 (0.8-3.0) | N |
| 23 | GTGCNGWFY | | | | 1 (1-7) | 0.7 (0.3-1.5) | N | 6 (3-20) | 1.4 (1.3-1.5) | N |
| 24 | LQDKJIDHY | | | | 3 (1-7) | 1.1 (0.4-1.5) | N | 8 (1-13) | 1.3 (1.0-1.8) | N |
| 25 | ATCVSHRGLY | | | | 3 (1-27) | 1.1 (0.2-3.0) | N | 2 (1-23) | 1.1 (0.5-1.9) | N |
| 26 | TLEKLTNTGLY | | | | 6 (1-20) | 1.3 (0.0-2.0) | N | 1 (1-13) | 1.0 (0.7-2.3) | N |
| | HLA-A02 | | | | | | | | | |
| 8 | FVYIPLFLI | 5 (1-5) | 1.4 (1.0-5.0) | N | 3 (1-20) | 1.1 (1.0-5.0) | N | 145 (30-195) | 15.5 (7.0-20.5) | Y |
| 29 | TVYVFCFLL | 1 (1-9) | 1.0 (1.0-10.0) | N | 3 (1-45) | 2.1 (1.0-5.0) | Y | 25 (20-25) | 3.5 (2.7-5.0) | N |
| 6 | CLYLHIQSL | 32 (1-55) | 4.1 (1.0-40.0) | Y | 10 (1-90) | 3.6 (1.7-20.0) | Y | 65 (35-100) | 11.0 (4.5-14.0) | Y |
| 7 | KLLSKLLCV | 62 (5-125) | 6.2 (1.3-95.0) | Y | 15 (4-120) | 4.2 (1.07-15.0) | Y | 95 (75-110) | 12.0 (10.5-16.0) | Y |
| 27 | ILYAHIQCL | 358 (155-720) | 41.3 (7.2-525.0) | Y | 613 (440-849) | 49.5 (30.3-850.0) | Y | 655 (440-865) | 66.5 (30.3-174.0) | Y |
| 28 | VAWDSVYYM | 290 (150-640) | 34.3 (7.0-435.0) | Y | 450 (299-784) | 39.0 (22.3-785.0) | Y | 495 (335-675) | 50.5 (23.3-136.0) | Y |
| 30 | SLQDIEITCV | 3 (1-10) | 1.3 (1.0-5.0) | | 1 (1-5) | 1.0 (1.0-5.0) | | 1 (1-5) | 1.0 (1.0-2.0) | |
| 133 | YMLDLQPETT | 5 (1-34) | 1.4 (1.0-35.0) | Y | 10 (4-245) | 3.3 (1.3-15.0) | Y | 1 (1-15) | 1.0 (1.0-4.0) | N |
| 134 | GTLGIVCPI | 1 (1-5) | 1.0 (1.0-5.0) | N | 3 (1-20) | 1.7 (1.0-10.0) | N | 55 (55-70) | 8.0 (6.5-12.0) | Y |
| 135 | TIHDIILECV | 562 (55-1520) | 86.7 (3.2-525.0) | Y | 358 (135-844) | 24.8 (10.0-845.0) | Y | 80 (45-155) | 10.0 (9.0-16.5) | Y |
| 136 | KLTNTGLYNL | 6 (1-30) | 2.0 (1.0-30.0) | Y | 20 (5-39) | 2.7 (1.3-40.0) | Y | 280 (115-420) | 29.0 (8.7-85.0) | Y |

TABLE 8-continued

Immunogenicity data for HLA class-I-restricted HPV 16 and HPV 18 epitopes encoded in constructs ICCG 6149 and ICCG 6150

| | HLA-A01 | | | | | | | | |
|---|---|---|---|---|---|---|---|---|---|
| | Sequence of WT | ICCG6149 | | | ICCG6150 | | | Peptide Pool | |
| SEQ ID | peptide used for CTL read-out | Delta SFC/10⁶ cells($^b$) | Ratio($^b$) | Immun Y/N | Delta SFC/10⁶ cells($^a$) | Ratio($^b$) | Immun Y/N | Delta SFC/10⁶ cells($^b$) | Ratio($^b$) | Immun Y/N |
| | HLA-A11 | | | | | | | | | |
| 17 | AATKYPLLK | 40 (1-140) | 1.5 (1.0-4.5) | Y | 45 (1-310) | 1.5 (1.0-16.5) | Y | 630 (200-680) | 16.8 (11.0-69.0) | Y |
| 13 | STAAALYWYK | 710 (480-2040) | 9.6 (3.8-52.0) | Y | 1305 (200-1970) | 21.4 (5.2-81.0) | Y | 950 (720-1010) | 37.0 (24.8-102.0) | Y |
| 14 | ATMCRHYKR | 1 (1-80) | 1.0 (1.0-5.0) | Y | 6 (1-80) | 1.0 (1.0-1.5) | N | 60 (1-100) | 4.0 (1.0-11.0) | Y |
| 15 | KSLFGMSLMK | 1 (1-1) | 1.0 (1.0-1.0) | N | 1 (1-50) | 1.0 (1.0-2.3) | Y | 620 (370-630) | 32.0 (10.3-64.0) | Y |
| 33 | TVSATQLVK | 15 (1-40) | 1.1 (1.0-2.0) | N | 11 (1-70) | 1.1 (1.0-3.0) | Y | 20 (1-90) | 1.1 (1.0-1.4) | N |
| 34 | STVSVGTAK | 435 (90-1600) | 5.1 (3.1-12.0) | Y | 245 (100-670) | 4.7 (2.6-14.5) | Y | 440 (60-1510) | 2.3 (1.2-7.0) | Y |
| 35 | QVVPAYNISK | 1 (1-10) | 1.0 (1.0-1.5) | N | 1 (1-20) | 1.0 (1.0-1.5) | N | 10 (1-100) | 1.0 (1.0-1.3) | N |
| 137 | DSVYGDTLEK | 15 (1-110) | 1.2 (1.0-3.2) | Y | 1 (1-10) | 1.0 (1.0-1.5) | N | 40 (1-70) | 1.1 (1.0-1.3) | N |
| 38 | ATLQDIVLH | 775 (10-1290) | 7.8 (1.1-40.5) | Y | 115 (1-1420) | 4.9 (1.0-36.5) | Y | 170 (1-440) | 1.7 (1.0-2.2) | Y |
| 12 | VVLLLVRYK | 1 (1-40) | 1.0 (1.0-2.0) | N | 15 (1-40) | 1.4 (1.0-2.0) | Y | 540 (420-630) | 22.0 (14.5-64.0) | Y |
| 16 | SVICFVNSK | 1 (1-20) | 1.0 (1.0-2.0) | N | 40 (1-110) | 1.6 (1.0-5.0) | Y | 320 (320-620) | 17.0 (9.0-63.0) | Y |
| 32 | KQGAMLAVFK | 1 ((1-20) | 1.0 (1.0-1.4) | N | 10 (1-150) | 1.3 (1.0-1.5) | N | 170 (1-220) | 1.5 (1.0-1.9) | N |
| 138 | FVVYRDSIPH | 1 (1-20) | 1.0 (1.0-2.0) | N | 1 (1-90) | 1.0 (1.0-5.5) | N | 110 (1-310) | 1.3 (1.0-2.2) | Y |
| | HLA-A24 | | | | | | | | | |
| 18 | LYGVSFSEL | 1200 (915-1510) | 21.1 (17.6-25.3) | Y | 1120 (250-1565) | 20.7 (4.8-33.8) | Y | 685 (590-1070) | 13.5 (10.1-31.6) | Y |
| 40 | YYMTDAGTW | 5 (1-15) | 1.1 (1.0-1.2) | N | 3 (1-20) | 1.1 (1.0-1.3) | N | 135 (1-135) | 2.7 (1.0-3.3) | Y |
| 41 | GYNTFYIEF | 80 (1-230) | 2.2 (1.0-5.6) | Y | 113 (1-435) | 3.0 (1.0-9.7) | Y | 110 (50-110) | 2.2 (1.6-2.8) | Y |
| 39 | SYFGMSFIHF | 808 (245-1070) | 14.1 (5.5-19.7) | Y | 498 (81-1150) | 8.3 (3.2-24.0) | Y | 65 (45-175) | 1.8 (1.5-3.9) | Y |
| 139 | CYSLYGTTL | 3 (1-5) | 1.0 (1.0-1.1) | N | 1 (1-10) | 1.0 (1.0-1.3) | N | 1 (1-1) | 1.0 (1.0-1.0) | N |
| 20 | VYDFAFRDLCI | 435 (285-1005) | 8.0 (5.3-21.1) | Y | 760 (155-1075) | 14.0 (3.6-20.4) | Y | 1 (1-110) | 1.0 (1.0-4.1) | N |
| 140 | PYAVCDKCL | 3 (1-25) | 1.1 (1.0-1.4) | N | 1 (1-5) | 1.0 (1.0-1.1) | N | 150 (35-175) | 4.2 (1.5-5.3) | Y |
| 141 | RFHNIRGRW | 3 (1-35) | 1.1 (1.0-1.5) | N | 1 (1-20) | 1.0 (1.0-1.4) | N | 205 (75-325) | 6.9 (2.2-6.9) | Y |
| 42 | MYVCCHVPL | 1 (1-15) | 1.0 (1.0-1.2) | N | 1 (1-25) | 1.0 (1.0-1.4) | N | 1 (1-1) | 1.0 (1.0-1.0) | N |
| 43 | VYVFCFLLPM | 1 (1-1) | 1.0 (1.0-1.0) | N | 1 (1-6) | 1.0 (1.0-1.2) | N | 365 (345-505) | 5.3 (5.1-9.4) | Y |
| 142 | LYNLLIRCL | 1 (1-10) | 1.0 (1.0-1.2) | N | 1 (1-1) | 1.0 (1.0-1.0) | N | 170 (100-450) | 3.8 (2.3-6.0) | Y |
| 143 | LYNLLIRWL | 3 (1-10) | 1.0 (1.0-1.2) | N | 1 (1-1) | 1.0 (1.0-1.0) | N | 30 (10-40) | 1.5 (1.1-1.5) | N |
| 144 | LYGVSFTEL | 3 (1-5) | 1.0 (1.0-1.1) | N | 1 (1-20) | 1.0 (1.0-1.4) | N | 5 (1-15) | 1.1 (1.0-1.2) | N |
| 145 | CYSVYGTTL | 23 (10-35) | 1.4 (1.2-1.6) | N | 90 (1-865) | 2.6 (1.0-13.4) | Y | 55 (1-150) | 1.8 (1.0-5.3) | Y |

($^b$)results expressed as: $\dfrac{\text{median}}{(\text{min} - \text{max})}$:

median, minimum and maximum CTL responses from the individual mouse pools
Immun = Immunogenic

TABLE 9

Immunogenicity data for HLA class-I-restricted HPV 31 and HPV 45 epitopes encoded in constructs ICCG 6137 and ICCG 6138

| SEQ ID | Sequence of WT peptide used for CTL read-out | ICCG6137 Delta | SFC/10⁶ cells Ratio | Immun Y/N | ICCG6138 Delta | SFC/10⁶ cells Ratio |
|---|---|---|---|---|---|---|
| | HLA-A01 | | | | | |
| 1 | LSQMVQWAY | | | | 13 (1-20) | 1.5 (0.3-3.0) |
| 23 | GTGCNGWFY | | | | 1 (1-25) | 1.0 (0.8-3.5) |
| 45 | VMDDSEIAY | | | | 238 (5-945) | 15.0 (1.5-64.0) |
| 46 | LSSALEIPY | | | | 3 (1-10) | 1.1 (0.5-2.0) |
| 47 | AFTDLTIVY | | | | 55 (15-770) | 3.9 (2.4-52.3) |
| 146 | QAEPDTSNY | | | | 23 (1-35) | 2.5 (0.5-4.5) |
| 67 | LQDKILDHY | | | | 3 (1-15) | 1.3 (0.3-1.6) |
| 68 | NTGILTVTY | | | | 6 (1-15) | 1.3 (0.8-2.5) |
| 147 | LQDVSIACVY | | | | 6 (1-20) | 1.4 (0.8-3.0) |
| 70 | NTELYNLLI | | | | 5 (1-15) | 1.4 (1.0-2.5) |
| 71 | ELDPVDLLCY | | | | 6 (1-10) | 1.4 (0.8-2.0) |
| | HLA-A02 | | | | | |
| 52 | FIYIPLFVI | 3 (1-15) | 1.1 (1.0-4.0) | N | 1 (1-10) | 1.0 (1.0-3.0) |
| 73 | YVVWDSIYYI | 3 (1-10) | 1.2 (1.0-2.0) | N | 1 (1-5) | 1.0 (1.0-2.0) |
| 49 | KLLEKLLCI | 1 (1-50) | 1.0 (1.0-11.0) | Y | 3 (1-35) | 1.5 (1.0-8.0) |
| 50 | YTNWKFIYL | 1 (1-20) | 1.0 (1.0-2.0) | N | 1 (1-5) | 1.0 (1.0-2.0) |
| 54 | KLTNKGICDL | 5 (1-25) | 2.0 (1.0-3.0) | Y | 7 (1-57) | 1.3 (1.0-7.0) |
| 72 | TLYAHIQCL | 1990 (1875-2185) | 259.0 (76.0-438.0) | Y | 1820 (1431-2369) | 159.4 (64.6-387.0) |
| 148 | FAFTDLTIV | 1 (1-5) | 1.0 (1.0-2.0) | N | 1 (1-5) | 1.0 (1.0-2.0) |
| 149 | YQFAFKDLCI | 3 (1-5) | 1.1 (1.0-2.0) | Y | 1 (1-30) | 1.0 (1.0-7.0) |
| 150 | TLQEIVLHL | 5 (1-42) | 2.0 (1.0-9.0) | Y | 3 (1-35) | 1.3 (1.0-3.3) |
| 74 | SLVFLLCFSV | 1 (1-10) | 1.0 (1.0-3.0) | N | 1 (1-5) | 1.0 (1.0-2.0) |
| 75 | FLLCFSVCL | 1 (1-10) | 1.0 (1.0-3.0) | N | 1 (1-5) | 1.0 (1.0-2.0) |
| 51 | FLLCFCVLL | 8 (1-30) | 2.0 (1.0-3.0) | Y | 8 (1-18) | 1.7 (1.0-4.0) |

TABLE 9-continued

Immunogenicity data for HLA class-I-restricted HPV 31 and HPV 45 epitopes encoded in constructs ICCG 6137 and ICCG 6138

| | HLA-A11 | | | | | |
|---|---|---|---|---|---|---|
| 151 | RTEVYQFAFK | 1 (1-90) | 1.0 (1.0-1.8) | N | 1 (1-90) | 1.0 (1.0-1.8) |
| 81 | VTTRYPLLR | 160 (72-1830) | 2.2 (1.4-15.1) | Y | 400 (50-720) | 4.0 (1.1-15.4) |
| 55 | MVMLMLVRFK | 10 (1-90) | 1.1 (1.0-1.6) | N | 1 (1-80) | 1.3 (1.0-2.6) |
| 56 | STAAALYWYR | 410 (210-1503) | 3.2 (1.5-10.8) | Y | 30 (1-100) | 1.1 (1.0-3.0) |
| 57 | ISFAGIVTK | 1 (1-330) | 1.0 (1.0-3.1) | Y | 120 (1-280) | 2.2 (1.0-3.4) |
| 58 | ATTPIIHLK | 920 (739-1500) | 5.8 (3.0-9.6) | Y | 1110 (540-1400) | 5.2 (2.9-11.8) |
| 59 | KVSEFRWYRY | 15 (1-110) | 1.0 (1.0-1.7) | N | 20 (1-90) | 1.3 (1.0-1.8) |
| 78 | AVMCRHYKR | 100 (27-250) | 1.6 (1.2-2.0) | Y | 20 (1-180) | 1.4 (1.0-1.8) |
| 79 | RQMNMSQWIK | 10 (1-110) | 1.0 (1.0-1.9) | N | 10 (1-130) | 1.2 (1.0-1.6) |
| 83 | SVYGETLEK | 50 (1-1230) | 1.2 (1.0-10.5) | Y | 130 (1-1250) | 2.3 (1.0-3.1) |
| 152 | SVYGTTLEK | 1050 (190-1660) | 5.4 (1.4-13.8) | Y | 1150 (450-2000) | 9.7 (1.8-26.4) |
| 80 | STWHWTGCNK | 70 (1-110) | 1.2 (1.0-1.9) | N | 70 (1-170) | 1.6 (1.0-1.8) |
| | HLA-A24 | | | | | |
| 65 | FYSKVSEFRW | 5 (1-12) | 1.2 (1.0-1.2) | N | 1 (1-35) | 1.0 (1.0-1.4) |
| 87 | VYQFAFKDL | 23 (1-340) | 1.5 (1.0-14.6) | Y | 1 (1-45) | 1.0 (1.0-1.5) |
| 39 | SYFGMSFIHF | 10 (1-10) | 1.2 (1.0-1.4) | N | 3 (1-85) | 1.0 (1.0-1.5) |
| 153 | HYTNWKFIY | 19 (5-65) | 1.3 (1.1-3.2) | Y | 58 (1-485) | 1.3 (1.0-6.7) |
| 62 | VFTFPNPFPF | 1543 (1490-2003) | 40.2 (20.9-61.4) | Y | 600 (310-790) | 5.3 (2.6-7.8) |
| 85 | YYITETGIW | 8 (1-15) | 1.2 (1.0-1.3) | N | 28 (1-640) | 1.2 (1.0-5.0) |
| 84 | VFTFPHAFPF | 10 (1-15) | 1.2 (1.0-1.6) | N | 3 (1-280) | 1.0 (1.0-2.8) |
| 66 | VYGTTLEKL | 77 (55-810) | 3.6 (2.2-11.8) | Y | 55 (1-530) | 1.4 (1.0-4.3) |
| 61 | PYLHSRLVVF | 17 (1-20) | 1.3 (1.0-1.7) | N | 1 (1-5) | 1.0 (1.0-1.1) |
| 64 | VVFIYIPLF | 46 (1-65) | 1.9 (1.0-2.8) | Y | 93 (5-555) | 1.3 (1.0-7.5) |
| 86 | VYVCAFAWLL | 712 (535-870) | 16.4 (11.8-29.2) | Y | 75 (35-410) | 1.4 (1.2-5.8) |
| 154 | FYSRIRELRY | 45 (1-210) | 2.0 (1.0-9.4) | Y | 33 (1-420) | 1.3 (1.0-5.9) |

TABLE 9-continued

Immunogenicity data for HLA class-I-restricted HPV 31 and HPV 45 epitopes encoded in constructs ICCG 6137 and ICCG 6138

| SEQ ID | Sequence of WT peptide used for CTL read-out | Immun Y/N | Peptide Pool Delta | SFC/10$^6$ cells Ratio | Immun Y/N |
|---|---|---|---|---|---|
| | HLA-A01 | | | | |
| 1 | LSQMVQWAY | N | 4 (1-13) | 1.3 (0.5-1.5) | N |
| 23 | GTGCNGWFY | N | 1 (1-7) | 0.7 (0.5-2.0) | N |
| 45 | VMDDSEIAY | Y | 53 (26-201) | 5.3 (2.6-13.2) | Y |
| 46 | LSSALEIPY | N | 1 (1-3) | 1.0 (0.8-1.3) | N |
| 47 | AFTDLTIVY | Y | 133 (23-201) | 10.8 (2.4-21.5) | Y |
| 146 | QAEPDTSNY | Y | 4 (1-10) | 1.2 (0.2-2.0) | N |
| 67 | LQDKILDHY | N | 2 (1-56) | 1.0 (0.6-4.4) | Y |
| 68 | NTGILTVTY | N | 2 (1-7) | 1.1 (0.6-1.5) | N |
| 147 | LQDVSIACVY | N | 1 (1-10) | 1.0 (0.6-2.0) | N |
| 70 | NTELYNLLI | N | 4 (1-10) | 1.2 (0.6-2.0) | N |
| 71 | ELDPVDLLCY | N | 1 (1-10) | 0.9 (0.4-2.0) | N |
| | HLA-A02 | | | | |
| 52 | FIYIPLFVI | N | 50 (40-65) | 5.0 (3.5-7.5) | Y |
| 73 | YVVWDSIYYI | N | 1 (1-5) | 1.0 (1.0-2.0) | N |
| 49 | KLLEKLLCI | Y | 40 (10-100) | 5.0 (2.0-6.0) | Y |
| 50 | YTNWKFIYL | N | 75 (65-170) | 8.5 (7.5-9.5) | Y |
| 54 | KLTNKGICDL | Y | 10 (10-105) | 2.0 (2.0-6.3) | Y |
| 72 | TLYAHIQCL | Y | 780 (440-780) | 79.0 (45.0-132.0) | Y |
| 148 | FAFTDLTIV | N | 100 (55-150) | 8.5 (6.5-11.0) | Y |
| 149 | YQFAFKDLCI | Y | 10 (5-85) | 2.0 (2.0-9.5) | Y |
| 150 | TLQEIVLHL | Y | 70 (35-310) | 8.0 (8.0-32.0) | Y |
| 74 | SLVFLLCFSV | N | 1 (1-1) | 1.0 (1.0-1.0) | N |
| 75 | FLLCFSVCL | N | 75 (70-85) | 8.5 (8.0-18.0) | Y |
| 51 | FLLCFCVLL | N | 195 (100-236) | 11.0 (10.8-24.5) | Y |

TABLE 9-continued

Immunogenicity data for HLA class-I-restricted HPV 31 and HPV 45 epitopes encoded in constructs ICCG 6137 and ICCG 6138

| | | | | | |
|---|---|---|---|---|---|
| HLA-A11 | | | | | |
| 151 | RTEVYQFAFK | N | 1 (1-1) | 1.0 (1.0-1.0) | N |
| 81 | VTTRYPLLR | Y | 430 (360-500) | 3.3 (3.3-3.3) | Y |
| 55 | MVMLMLVRFK | Y | 510 (490-1100) | 4.9 (3.9-8.9) | Y |
| 56 | STAAALYWYR | Y | 710 (410-990) | 6.5 (3.4-8.1) | Y |
| 57 | ISFAGIVTK | Y | 1350 (960-1530) | 10.6 (6.6-12.8) | Y |
| 58 | ATTPIIHLK | Y | 1810 (1220-1880) | 13.9 (8.2-15.5) | Y |
| 59 | KVSEFRWYRY | N | 20 (10-110) | 1.1 (1.1-1.6) | N |
| 78 | AVMCRHYKR | N | 31 (1-60) | 1.1 (1.0-1.4) | N |
| 79 | RQMNMSQWIK | N | 435 (380-490) | 3.3 (3.2-3.4) | Y |
| 83 | SVYGETLEK | Y | 1080 (730-1430) | 7.1 (4.3-9.9) | Y |
| 152 | SVYGTTLEK | Y | 730 (120-1560) | 6.2 (1.9-10.2) | Y |
| 80 | STWHWTGCNK | N | 635 (560-710) | 4.4 (4.2-4.5) | Y |
| HLA-A24 | | | | | |
| 65 | FYSKVSEFRW | N | 1 (1-60) | 1.0 (1.0-2.7) | Y |
| 87 | VYQFAFKDL | N | 105 (75-165) | 4.5 (4.0-5.7) | Y |
| 39 | SYFGMSFIHF | N | 45 (35-160) | 2.8 (2.2-5.6) | Y |
| 153 | HYTNWKFIY | Y | 155 (60-485) | 2.7 (2.7-4.6) | Y |
| 62 | VFTFPNPFPF | Y | 940 (815-1195) | 14.3 (8.0-24.3) | Y |
| 85 | YYITETGIW | Y | 15 (1-25) | 1.4 (1.0-2.0) | N |
| 84 | VFTFPHAFPF | Y | 75 (25-165) | 4.0 (1.8-5.7) | Y |
| 66 | VYGTTLEKL | Y | 105 (25-275) | 4.0 (1.2-4.1) | Y |
| 61 | PYLHSRLVVF | N | 1 (1-40) | 1.0 (1.0-2.1) | Y |
| 64 | VVFIYIPLF | Y | 715 (710-1055) | 12.8 (6.3-21.4) | Y |
| 86 | VYVCAFAWLL | Y | 125 (105-295) | 6.0 (4.5-9.4) | Y |
| 154 | FYSRIRELRY | Y | 165 (115-220) | 7.3 (4.8-7.6) | Y |

Immun = Immunogenic

Example 4

HTL Epitope Recall Responses in HPV Infected Women

The purpose of this set of experiments is to demonstrate in vitro human recall HTL responses in a panel of HPV-infected subjects towards the final selection of HTL epitopes comprised in the HPV polyepitope constructs, using an optimized human T-cell proliferation assay.

Following table 10 gives an overview of the peptides used in the T-cell proliferation assay. Peptide sequence and source are listed. All peptides are dissolved in 100% dimethyl sulfoxide (DMSO) at a concentration of 5, 10, or 20 mg/ml and stored at −20° C. Peptides were used in the T-cell proliferation assay at a final concentration of 10 μg/ml. As a positive control antigen, Tetanus Toxoid (TT) was used at a final concentration of 3 μg/ml.

TABLE 10

| Sequence | Source | SEQ ID |
|---|---|---|
| LYWYKTGISNISEVY | HPV16.E1.319 | 89 |
| PEWIQRQTVLQHSFN | HPV16.E1.337 | 90 |
| WKHMRLECAIYYKAR | HPV16.E2.033 | 91 |
| LQAIELQLTLETIYN | HPV16.E2.070 | 92 |
| GLYYVHEGIRTYFVQ | HPV16.E2.156 | 93 |
| QRFHNIRGRWTGRCM | HPV16.E6.130 | 94 |
| LDLQPETTDLYCYEQ | HPV16.E7.13 | 95 |
| LCTELQTTIHDIILE | HPV16.E6.22 | 96 |
| IRTLEDLLMGTLGIV | HPV16.E7.76 | 97 |
| FKTLIQPFILYAHIQ | HPV18.E1.258 | 98 |
| IEFITFLGALKSFLK | HPV18.E1.458 | 99 |
| FLNTVAIPDSVQILV | HPV18.E2.346 | 100 |
| HKAIELQMALQGLAQ | HPV18.E2.074 | 101 |
| EVFEFAFKDLFVVYR | HPV18.E6.43 | 102 |
| LFVVYRDSIPHAACHK | HPV18.E6.52 | 103 |
| TNTGLYNLLIRCLRCQ | HPV18.E6.94 | 104 |
| FQQLFLNTLSFVCPW | HPV18.E7.86 | 105 |
| NGWFYVEAVIDRQTG | HPV31.E1.15 | 106 |
| PEWIERQTVLQHSFN | HPV31.E1.317 | 107 |
| WKHIRLECVLMYKAR | HPV31.E2.033 | 108 |
| TTPIIHLKGDANILK | HPV31.E2.292 | 109 |
| TGRCIACWRRPRTET | HPV31.E6.132 | 110 |
| VLDFAFTDLTIVYRD | HPV31.E6.42 | 111 |
| IRILQELLMGSFGIV | HPV31.E7.76 | 112 |
| PRKLHELSSALEIPY | HPV31.E6.9 | 113 |
| DWVMAIFGVNPTVAEGF | HPV45.E1.228 | 114 |
| FKTLIKPATLYAHIQ | HPV45.E1.244 | 115 |

TABLE 10-continued

| Sequence | Source | SEQ ID |
|---|---|---|
| PINISKSKAHKAIEL | HPV45.E2.67 | 116 |
| TIPNSVQISVGYMTI | HPV45.E2.354 | 117 |
| LCIVYRDCIAYAACH | HPV45.E6.52 | 118 |
| FHSIAGQYRGQCNTC | HPV45.E6.127 | 119 |
| EIVLHLEPQNELDPV | HPV45.E7.10 | 120 |
| LRTLQQLFLSTLSFV | HPV45.E7.84 | 121 |

PBMC from HPV-infected subjects, currently or previously diagnosed with cervical intra-epithelial neoplasia (CIN) 1, 2, or 3, and preferentially HPV-genotyped were used to determine the HPV-specific HTL responses. PBMC were thawed following standard procedures for use in the T-cell proliferation assay.

PBMC samples from HPV-infected subjects were screened for in vitro recall HTL responses towards the whole panel of HTL peptides using a T-cell proliferation assay. Briefly, $5 \times 10^4$ cells/well were seeded in 5-fold replicates, in round bottom plates in RPMI total (=RPMIbic+non essential amino acids (NEAA)+sodium pyruvate+gentamycine+beta mercapto ethanol (βME)), supplemented with 5% heat-inactivated human AB serum (ihuAB), and incubated with 10 μg/ml HTL peptide or 3 μg/ml TT during 6 days in a CO2 incubator at 37° C. After this incubation period, $^3$H-thymidine (1 μCi/well) was added for overnight labeling (18 hours). Then cells were harvested and the amount of incorporated $^3$H-thymidine was measured. TT was included as a positive control, as most people are expected to show a response towards this antigen. Additionally, cells from a healthy control PBMC sample were seeded ($5 \times 10^4$ c/well, 5-fold replicates) and stimulated with TT and Varicella Zoster in order to have an internal assay control on each plate and to evaluate inter and intra assay variability.

Data Analysis

All raw data points, calculated and reported values are collected in an Excel database per experimental setup.

The magnitude of the antigen-specific response as determined in the T-cell proliferation assay is expressed as stimulation index (the median cpm of stimulated/non-stimulated cultures) and delta cpm (the median cpm value of stimulated wells subtracted from the median cpm value of non-stimulated wells).

A response is considered positive when the delta cpm values ≥200 cpm and the stimulation index is ≥2.

The highest, positive responses per HTL epitope are shown (SI values only) in FIG. 9. These data clearly show that—although tested in only a limited set of blood samples from HPV infected patients—T cell reactivity can be picked up for the majority of the selected HTL epitopes.

REFERENCES

Alexander, J. et al., J. Immunol. 159:4753, 1997
Alexander J. et al., Hum Immunol 64(2): 211-223, 2003
An, L. and Whitton, J. L., J. Virol. 71:2292, 1997
Bertoni, R. et al., J. Clin. Invest. 100:503, 1997
Beaucage & Caruthers, Tetrahedron Letts. 22:1859-1862, 1981
Bowen, D G and Walker, M W, Nature, 436:946, 2005
Celis, E. et al., Proc. Natl. Acad. Sci. USA 91:2105, 1994
Diepolder, H. M. et al., J. Virol. 71:6011, 1997

Donnelly J J, et al. Annu Rev Immunol. 1997; 15:617-48.
Donnelly J J, Ulmer J B, Liu M A. DNA vaccines. Life Sci. 1997a; 60(3):163-72.
Doolan, D. L. et al., Immunity 7:97-112, 1997
Doorbar J., J Clin Virol 32S:S7-S15, 2005
Felgner, et al., Proc. Nat'l Acad. Sci. USA 84:7413, 1987
Gaberc-Porekar V. et al., J. Biochem. Biophys. Methods 49: 335-360, 2001
Gruters R A, van Baalen C A, Osterhaus A D. Vaccine. 2002 May 6; 20(15):2011-5. The advantage of early recognition of HIV-infected cells by cytotoxic T-lymphocytes.
Hanke, R. et al., Vaccine 16:426, 1998
Houssaint E, Saulquin X, Scotet E, Bonneville M Biomed Pharmacother. 2001 September; 55(7): 373-80. Immunodominant CD8 T cell response to Epstein-Barr virus.
Ishioka, et al., J. Immunol. (1999) 162(7):3915-3925
Kawashima, I. et al., Human Immunol. 59:1, 1998
Kriegler M. Gene transfer and expression: a laboratory manual. W.H. Freeman and Company, New York, 1991: 60-61 and 165-172.
Lichty J. J. et al., Protein Expression and Protein Purification 41: 98-105, 2005
Mannino & Gould-Fogerite, BioTechniques 6(7): 682, 1988
Mateo et al., J Immunol, 163(7): 4058-63, 1999
Murray N, McMichael A. Curr Opin Immunol. 1992 August; 4(4):401-7. Antigen presentation in virus infection.
Pearson & Reanier, J. Chrom. 255:137-149, 1983
Rehermann, B. et al., J. Exp. Med. 181:1047, 1995
Rowen, P. and Lacey, C., Dermatologic Clinics 16 (4): 835-838, 1998
Sette, et al, J Immunol 153:5586-5592, 1994
Sette, et al., Mol. Immunol. 31: 813 (1994).
Sidney et al., Current Protocols in Immunology, Ed., John Wiley & Sons, NY, Section 18.3 (1998)
Sidney, et al., J. Immunol. 154: 247 (1995)
Southwood et al. J Immunology 160:3363-3373, 1998
Stemmer W P et al. Gene 164: 49-53, 1995
Stover et al., Nature 351:456-460, 1991
Threlkeld, S. C. et al., J. Immunol. 159:1648, 1997
Tigges M A, et al., J. Virol.; 66(3):1622-34 1992
Thomson et al., Proc Natl Acad Sci USA, 92(13):5845-9, 1995
Thomson, S. A. et al., J. Immunol. 157:822, 1996
Tsai S L, Huang S N. J Gastroenterol Hepatol. 1997 October; 12(9-10):S227-35. T cell mechanisms in the immuno-pathogenesis of viral hepatitis B and C.
Tsai, V. et al., J. Immunol. 158:1796, 1997
Van Devanter et. al., Nucleic Acids Res. 12:6159-616S, 1984
Velders M P et al. J Immunol, 166(9): 5366-73, 2001
Wentworth, P. A. et al., Mol. Immunol. 32:603, 1995
Wentworth, P. A. et al., J. Immunol. 26:97, 1996
Whitton, J. L. et al., J. Prol. 67:348, 1993
Woodberry et al, J Virol, 73(7):5320-5, 1999

The invention claimed is:

1. An isolated polynucleotide construct which comprises nucleic acids that encode an amino acid sequence selected from the group consisting of: SEQ ID NO:160, SEQ ID NO:162, SEQ ID NO:127, and SEQ ID NO:129.

2. The isolated polynucleotide construct of claim 1, wherein the amino acid sequence is SEQ ID NO: 127.

3. A vector comprising the isolated polynucleotide construct of claim 1.

4. The vector of claim 3, wherein said vector is an expression vector.

5. The vector of claim 4, wherein said expression vector is a vaccinia virus.

6. A cell comprising the vector of claim 3.

7. An isolated polypeptide encoded by the polynucleotide construct of claim 1.

8. A pharmaceutical composition comprising the isolated polynucleotide construct of claim 1 and a pharmaceutically acceptable excipient.

9. A pharmaceutical composition comprising the isolated polypeptide of claim 7 and a pharmaceutically acceptable excipient.

10. A method of inducing an immune response against human papillomavirus virus (HPV) in an individual, comprising administering to said individual an effective amount of the isolated polynucleotide construct of claim 1.

11. A method of inducing an immune response against human papillomavirus virus (HPV) in an individual, comprising administering to said individual an effective amount of the isolated polypeptide of claim 7.

12. A method of treating HPV infection or HPV-related disease in an individual, comprising administering to said individual a therapeutically effective amount of the isolated polynucleotide construct of claim 1.

13. A method of treating HPV infection or HPV-related disease in an individual, comprising administering to said individual a therapeutically effective amount of the isolated polypeptide of claim 7.

* * * * *

SEQUENCE LISTING

```
<160> NUMBER OF SEQ ID NOS: 163

<210> SEQ ID NO 1
<211> LENGTH: 9
<212> TYPE: PRT
<213> ORGANISM: Human papillomavirus type 16

<400> SEQUENCE: 1

Leu Ser Gln Met Val Gln Trp Ala Tyr
1               5

<210> SEQ ID NO 2
<211> LENGTH: 9
<212> TYPE: PRT
<213> ORGANISM: Human papillomavirus type 16

<400> SEQUENCE: 2

Gln Val Asp Tyr Tyr Gly Leu Tyr Tyr
1               5

<210> SEQ ID NO 3
<211> LENGTH: 10
<212> TYPE: PRT
<213> ORGANISM: Human papillomavirus type 16

<400> SEQUENCE: 3

Ser Thr Asp Leu Arg Asp His Ile Asp Tyr
1               5                   10

<210> SEQ ID NO 4
<211> LENGTH: 9
<212> TYPE: PRT
<213> ORGANISM: Human papillomavirus type 16

<400> SEQUENCE: 4

Lys Ser Ala Ile Val Thr Leu Thr Tyr
1               5
```

```
<210> SEQ ID NO 5
<211> LENGTH: 9
<212> TYPE: PRT
<213> ORGANISM: Artificial
<220> FEATURE:
<223> OTHER INFORMATION: Human papillomavirus type 16-derived epitope

<400> SEQUENCE: 5

Ile Ser Asp Tyr Arg His Tyr Cys Tyr
1               5

<210> SEQ ID NO 6
<211> LENGTH: 9
<212> TYPE: PRT
<213> ORGANISM: Human papillomavirus type 16

<400> SEQUENCE: 6

Cys Leu Tyr Leu His Ile Gln Ser Leu
1               5

<210> SEQ ID NO 7
<211> LENGTH: 9
<212> TYPE: PRT
<213> ORGANISM: Human papillomavirus type 16

<400> SEQUENCE: 7

Lys Leu Leu Ser Lys Leu Leu Cys Val
1               5

<210> SEQ ID NO 8
<211> LENGTH: 9
<212> TYPE: PRT
<213> ORGANISM: Human papillomavirus type 16

<400> SEQUENCE: 8

Phe Val Tyr Ile Pro Leu Phe Leu Ile
1               5

<210> SEQ ID NO 9
<211> LENGTH: 10
<212> TYPE: PRT
<213> ORGANISM: Artificial
<220> FEATURE:
<223> OTHER INFORMATION: Human papillomavirus type 16-derived epitope

<400> SEQUENCE: 9

Thr Leu His Asp Ile Ile Leu Glu Cys Val
1               5                   10

<210> SEQ ID NO 10
<211> LENGTH: 10
<212> TYPE: PRT
<213> ORGANISM: Artificial
<220> FEATURE:
<223> OTHER INFORMATION: Human papillomavirus type 16-derived epitope

<400> SEQUENCE: 10

Tyr Met Leu Asp Leu Gln Pro Glu Thr Val
1               5                   10

<210> SEQ ID NO 11
<211> LENGTH: 9
<212> TYPE: PRT
<213> ORGANISM: Artificial
<220> FEATURE:
```

```
<223> OTHER INFORMATION: Human papillomavirus type 16-derived epitope

<400> SEQUENCE: 11

Gly Thr Leu Gly Ile Val Cys Pro Val
1               5

<210> SEQ ID NO 12
<211> LENGTH: 9
<212> TYPE: PRT
<213> ORGANISM: Human papillomavirus type 16

<400> SEQUENCE: 12

Val Val Leu Leu Leu Val Arg Tyr Lys
1               5

<210> SEQ ID NO 13
<211> LENGTH: 10
<212> TYPE: PRT
<213> ORGANISM: Human papillomavirus type 16

<400> SEQUENCE: 13

Ser Thr Ala Ala Ala Leu Tyr Trp Tyr Lys
1               5                   10

<210> SEQ ID NO 14
<211> LENGTH: 9
<212> TYPE: PRT
<213> ORGANISM: Human papillomavirus type 16

<400> SEQUENCE: 14

Ala Thr Met Cys Arg His Tyr Lys Arg
1               5

<210> SEQ ID NO 15
<211> LENGTH: 10
<212> TYPE: PRT
<213> ORGANISM: Human papillomavirus type 16

<400> SEQUENCE: 15

Lys Ser Leu Phe Gly Met Ser Leu Met Lys
1               5                   10

<210> SEQ ID NO 16
<211> LENGTH: 9
<212> TYPE: PRT
<213> ORGANISM: Human papillomavirus type 16

<400> SEQUENCE: 16

Ser Val Ile Cys Phe Val Asn Ser Lys
1               5

<210> SEQ ID NO 17
<211> LENGTH: 9
<212> TYPE: PRT
<213> ORGANISM: Human papillomavirus type 16

<400> SEQUENCE: 17

Ala Ala Thr Lys Tyr Pro Leu Leu Lys
1               5

<210> SEQ ID NO 18
<211> LENGTH: 9
<212> TYPE: PRT
<213> ORGANISM: Human papillomavirus type 16
```

```
<400> SEQUENCE: 18

Leu Tyr Gly Val Ser Phe Ser Glu Leu
1               5

<210> SEQ ID NO 19
<211> LENGTH: 9
<212> TYPE: PRT
<213> ORGANISM: Artificial
<220> FEATURE:
<223> OTHER INFORMATION: Human papillomavirus type 16-derived epitope

<400> SEQUENCE: 19

Arg Phe His Asn Ile Arg Gly Arg Phe
1               5

<210> SEQ ID NO 20
<211> LENGTH: 11
<212> TYPE: PRT
<213> ORGANISM: Human papillomavirus type 16

<400> SEQUENCE: 20

Val Tyr Asp Phe Ala Phe Arg Asp Leu Cys Ile
1               5                   10

<210> SEQ ID NO 21
<211> LENGTH: 9
<212> TYPE: PRT
<213> ORGANISM: Artificial
<220> FEATURE:
<223> OTHER INFORMATION: Human papillomavirus type 16-derived epitope

<400> SEQUENCE: 21

Pro Tyr Ala Val Cys Asp Lys Cys Phe
1               5

<210> SEQ ID NO 22
<211> LENGTH: 9
<212> TYPE: PRT
<213> ORGANISM: Artificial
<220> FEATURE:
<223> OTHER INFORMATION: Human papillomavirus type 16-derived epitope

<400> SEQUENCE: 22

Cys Tyr Ser Leu Tyr Gly Thr Thr Phe
1               5

<210> SEQ ID NO 23
<211> LENGTH: 9
<212> TYPE: PRT
<213> ORGANISM: Human papillomavirus type 18

<400> SEQUENCE: 23

Gly Thr Gly Cys Asn Gly Trp Phe Tyr
1               5

<210> SEQ ID NO 24
<211> LENGTH: 9
<212> TYPE: PRT
<213> ORGANISM: Human papillomavirus type 18

<400> SEQUENCE: 24

Leu Gln Asp Lys Ile Ile Asp His Tyr
1               5

<210> SEQ ID NO 25
```

```
<211> LENGTH: 10
<212> TYPE: PRT
<213> ORGANISM: Human papillomavirus type 18

<400> SEQUENCE: 25

Ala Thr Cys Val Ser His Arg Gly Leu Tyr
1               5                   10

<210> SEQ ID NO 26
<211> LENGTH: 11
<212> TYPE: PRT
<213> ORGANISM: Human papillomavirus type 18

<400> SEQUENCE: 26

Thr Leu Glu Lys Leu Thr Asn Thr Gly Leu Tyr
1               5                   10

<210> SEQ ID NO 27
<211> LENGTH: 9
<212> TYPE: PRT
<213> ORGANISM: Human papillomavirus type 18

<400> SEQUENCE: 27

Ile Leu Tyr Ala His Ile Gln Cys Leu
1               5

<210> SEQ ID NO 28
<211> LENGTH: 9
<212> TYPE: PRT
<213> ORGANISM: Human papillomavirus type 18

<400> SEQUENCE: 28

Val Ala Trp Asp Ser Val Tyr Tyr Met
1               5

<210> SEQ ID NO 29
<211> LENGTH: 9
<212> TYPE: PRT
<213> ORGANISM: Human papillomavirus type 18

<400> SEQUENCE: 29

Thr Val Tyr Val Phe Cys Phe Leu Leu
1               5

<210> SEQ ID NO 30
<211> LENGTH: 10
<212> TYPE: PRT
<213> ORGANISM: Human papillomavirus type 18

<400> SEQUENCE: 30

Ser Leu Gln Asp Ile Glu Ile Thr Cys Val
1               5                   10

<210> SEQ ID NO 31
<211> LENGTH: 10
<212> TYPE: PRT
<213> ORGANISM: Artificial
<220> FEATURE:
<223> OTHER INFORMATION: Human papillomavirus type 18-derived epitope

<400> SEQUENCE: 31

Lys Leu Thr Asn Thr Gly Leu Tyr Asn Val
1               5                   10

<210> SEQ ID NO 32
```

```
<211> LENGTH: 10
<212> TYPE: PRT
<213> ORGANISM: Human papillomavirus type 18

<400> SEQUENCE: 32

Lys Gln Gly Ala Met Leu Ala Val Phe Lys
1               5                   10

<210> SEQ ID NO 33
<211> LENGTH: 9
<212> TYPE: PRT
<213> ORGANISM: Human papillomavirus type 18

<400> SEQUENCE: 33

Thr Val Ser Ala Thr Gln Leu Val Lys
1               5

<210> SEQ ID NO 34
<211> LENGTH: 9
<212> TYPE: PRT
<213> ORGANISM: Human papillomavirus type 18

<400> SEQUENCE: 34

Ser Thr Val Ser Val Gly Thr Ala Lys
1               5

<210> SEQ ID NO 35
<211> LENGTH: 10
<212> TYPE: PRT
<213> ORGANISM: Human papillomavirus type 18

<400> SEQUENCE: 35

Gln Val Val Pro Ala Tyr Asn Ile Ser Lys
1               5                   10

<210> SEQ ID NO 36
<211> LENGTH: 10
<212> TYPE: PRT
<213> ORGANISM: Artificial
<220> FEATURE:
<223> OTHER INFORMATION: Human papillomavirus type 18-derived epitope

<400> SEQUENCE: 36

Phe Val Val Tyr Arg Asp Ser Ile Pro Lys
1               5                   10

<210> SEQ ID NO 37
<211> LENGTH: 10
<212> TYPE: PRT
<213> ORGANISM: Artificial
<220> FEATURE:
<223> OTHER INFORMATION: Human papillomavirus type 18-derived epitope

<400> SEQUENCE: 37

Asp Ser Val Tyr Gly Asp Thr Leu Glu Arg
1               5                   10

<210> SEQ ID NO 38
<211> LENGTH: 9
<212> TYPE: PRT
<213> ORGANISM: Human papillomavirus type 18

<400> SEQUENCE: 38

Ala Thr Leu Gln Asp Ile Val Leu His
1               5
```

```
<210> SEQ ID NO 39
<211> LENGTH: 10
<212> TYPE: PRT
<213> ORGANISM: Human papillomavirus type 18

<400> SEQUENCE: 39

Ser Tyr Phe Gly Met Ser Phe Ile His Phe
1               5                   10

<210> SEQ ID NO 40
<211> LENGTH: 9
<212> TYPE: PRT
<213> ORGANISM: Human papillomavirus type 18

<400> SEQUENCE: 40

Tyr Tyr Met Thr Asp Ala Gly Thr Trp
1               5

<210> SEQ ID NO 41
<211> LENGTH: 9
<212> TYPE: PRT
<213> ORGANISM: Human papillomavirus type 18

<400> SEQUENCE: 41

Gly Tyr Asn Thr Phe Tyr Ile Glu Phe
1               5

<210> SEQ ID NO 42
<211> LENGTH: 9
<212> TYPE: PRT
<213> ORGANISM: Human papillomavirus type 18

<400> SEQUENCE: 42

Met Tyr Val Cys Cys His Val Pro Leu
1               5

<210> SEQ ID NO 43
<211> LENGTH: 10
<212> TYPE: PRT
<213> ORGANISM: Human papillomavirus type 18

<400> SEQUENCE: 43

Val Tyr Val Phe Cys Phe Leu Leu Pro Met
1               5                   10

<210> SEQ ID NO 44
<211> LENGTH: 9
<212> TYPE: PRT
<213> ORGANISM: Artificial
<220> FEATURE:
<223> OTHER INFORMATION: Human papillomavirus type 18-derived epitope

<400> SEQUENCE: 44

Leu Tyr Asn Leu Leu Ile Arg Cys Phe
1               5

<210> SEQ ID NO 45
<211> LENGTH: 9
<212> TYPE: PRT
<213> ORGANISM: Human papillomavirus type 31

<400> SEQUENCE: 45

Val Met Asp Asp Ser Glu Ile Ala Tyr
1               5
```

```
<210> SEQ ID NO 46
<211> LENGTH: 9
<212> TYPE: PRT
<213> ORGANISM: Human papillomavirus type 31

<400> SEQUENCE: 46

Leu Ser Ser Ala Leu Glu Ile Pro Tyr
1               5

<210> SEQ ID NO 47
<211> LENGTH: 9
<212> TYPE: PRT
<213> ORGANISM: Human papillomavirus type 31

<400> SEQUENCE: 47

Ala Phe Thr Asp Leu Thr Ile Val Tyr
1               5

<210> SEQ ID NO 48
<211> LENGTH: 9
<212> TYPE: PRT
<213> ORGANISM: Artificial
<220> FEATURE:
<223> OTHER INFORMATION: Human papillomavirus type 31-derived epitope

<400> SEQUENCE: 48

Gln Thr Glu Pro Asp Thr Ser Asn Tyr
1               5

<210> SEQ ID NO 49
<211> LENGTH: 9
<212> TYPE: PRT
<213> ORGANISM: Human papillomavirus type 31

<400> SEQUENCE: 49

Lys Leu Leu Glu Lys Leu Leu Cys Ile
1               5

<210> SEQ ID NO 50
<211> LENGTH: 9
<212> TYPE: PRT
<213> ORGANISM: Human papillomavirus type 31

<400> SEQUENCE: 50

Tyr Thr Asn Trp Lys Phe Ile Tyr Leu
1               5

<210> SEQ ID NO 51
<211> LENGTH: 9
<212> TYPE: PRT
<213> ORGANISM: Human papillomavirus type 31

<400> SEQUENCE: 51

Phe Leu Leu Cys Phe Cys Val Leu Leu
1               5

<210> SEQ ID NO 52
<211> LENGTH: 9
<212> TYPE: PRT
<213> ORGANISM: Human papillomavirus type 31

<400> SEQUENCE: 52

Phe Ile Tyr Ile Pro Leu Phe Val Ile
1               5
```

```
<210> SEQ ID NO 53
<211> LENGTH: 9
<212> TYPE: PRT
<213> ORGANISM: Artificial
<220> FEATURE:
<223> OTHER INFORMATION: Human papillomavirus type 31-derived epitope

<400> SEQUENCE: 53

Phe Leu Phe Thr Asp Leu Thr Ile Val
1               5

<210> SEQ ID NO 54
<211> LENGTH: 10
<212> TYPE: PRT
<213> ORGANISM: Human papillomavirus type 31

<400> SEQUENCE: 54

Lys Leu Thr Asn Lys Gly Ile Cys Asp Leu
1               5                   10

<210> SEQ ID NO 55
<211> LENGTH: 10
<212> TYPE: PRT
<213> ORGANISM: Human papillomavirus type 31

<400> SEQUENCE: 55

Met Val Met Leu Met Leu Val Arg Phe Lys
1               5                   10

<210> SEQ ID NO 56
<211> LENGTH: 10
<212> TYPE: PRT
<213> ORGANISM: Human papillomavirus type 31

<400> SEQUENCE: 56

Ser Thr Ala Ala Ala Leu Tyr Trp Tyr Arg
1               5                   10

<210> SEQ ID NO 57
<211> LENGTH: 9
<212> TYPE: PRT
<213> ORGANISM: Human papillomavirus type 31

<400> SEQUENCE: 57

Ile Ser Phe Ala Gly Ile Val Thr Lys
1               5

<210> SEQ ID NO 58
<211> LENGTH: 9
<212> TYPE: PRT
<213> ORGANISM: Human papillomavirus type 31

<400> SEQUENCE: 58

Ala Thr Thr Pro Ile Ile His Leu Lys
1               5

<210> SEQ ID NO 59
<211> LENGTH: 10
<212> TYPE: PRT
<213> ORGANISM: Human papillomavirus type 31

<400> SEQUENCE: 59

Lys Val Ser Glu Phe Arg Trp Tyr Arg Tyr
1               5                   10
```

<210> SEQ ID NO 60
<211> LENGTH: 9
<212> TYPE: PRT
<213> ORGANISM: Artificial
<220> FEATURE:
<223> OTHER INFORMATION: Human papillomavirus type 31-derived epitope

<400> SEQUENCE: 60

Ser Val Tyr Gly Thr Thr Leu Glu Arg
1               5

<210> SEQ ID NO 61
<211> LENGTH: 10
<212> TYPE: PRT
<213> ORGANISM: Human papillomavirus type 31

<400> SEQUENCE: 61

Pro Tyr Leu His Ser Arg Leu Val Val Phe
1               5                   10

<210> SEQ ID NO 62
<211> LENGTH: 10
<212> TYPE: PRT
<213> ORGANISM: Human papillomavirus type 31

<400> SEQUENCE: 62

Val Phe Thr Phe Pro Asn Pro Phe Pro Phe
1               5                   10

<210> SEQ ID NO 63
<211> LENGTH: 9
<212> TYPE: PRT
<213> ORGANISM: Artificial
<220> FEATURE:
<223> OTHER INFORMATION: Human papillomavirus type 31-derived epitope

<400> SEQUENCE: 63

His Tyr Thr Asn Trp Lys Phe Ile Phe
1               5

<210> SEQ ID NO 64
<211> LENGTH: 9
<212> TYPE: PRT
<213> ORGANISM: Human papillomavirus type 31

<400> SEQUENCE: 64

Val Val Phe Ile Tyr Ile Pro Leu Phe
1               5

<210> SEQ ID NO 65
<211> LENGTH: 10
<212> TYPE: PRT
<213> ORGANISM: Human papillomavirus type 31

<400> SEQUENCE: 65

Phe Tyr Ser Lys Val Ser Glu Phe Arg Trp
1               5                   10

<210> SEQ ID NO 66
<211> LENGTH: 9
<212> TYPE: PRT
<213> ORGANISM: Human papillomavirus type 31

<400> SEQUENCE: 66

Val Tyr Gly Thr Thr Leu Glu Lys Leu

```
<210> SEQ ID NO 67
<211> LENGTH: 9
<212> TYPE: PRT
<213> ORGANISM: Human papillomavirus type 45

<400> SEQUENCE: 67

Leu Gln Asp Lys Ile Leu Asp His Tyr
1               5

<210> SEQ ID NO 68
<211> LENGTH: 9
<212> TYPE: PRT
<213> ORGANISM: Human papillomavirus type 45

<400> SEQUENCE: 68

Asn Thr Gly Ile Leu Thr Val Thr Tyr
1               5

<210> SEQ ID NO 69
<211> LENGTH: 10
<212> TYPE: PRT
<213> ORGANISM: Artificial
<220> FEATURE:
<223> OTHER INFORMATION: Human papillomavirus type 45-derived epitope

<400> SEQUENCE: 69

Leu Thr Asp Val Ser Ile Ala Cys Val Tyr
1               5                   10

<210> SEQ ID NO 70
<211> LENGTH: 9
<212> TYPE: PRT
<213> ORGANISM: Human papillomavirus type 45

<400> SEQUENCE: 70

Asn Thr Glu Leu Tyr Asn Leu Leu Ile
1               5

<210> SEQ ID NO 71
<211> LENGTH: 10
<212> TYPE: PRT
<213> ORGANISM: Human papillomavirus type 45

<400> SEQUENCE: 71

Glu Leu Asp Pro Val Asp Leu Leu Cys Tyr
1               5                   10

<210> SEQ ID NO 72
<211> LENGTH: 9
<212> TYPE: PRT
<213> ORGANISM: Human papillomavirus type 45

<400> SEQUENCE: 72

Thr Leu Tyr Ala His Ile Gln Cys Leu
1               5

<210> SEQ ID NO 73
<211> LENGTH: 10
<212> TYPE: PRT
<213> ORGANISM: Human papillomavirus type 45

<400> SEQUENCE: 73

Tyr Val Val Trp Asp Ser Ile Tyr Tyr Ile
```

```
1               5                   10

<210> SEQ ID NO 74
<211> LENGTH: 10
<212> TYPE: PRT
<213> ORGANISM: Human papillomavirus type 45

<400> SEQUENCE: 74

Ser Leu Val Phe Leu Leu Cys Phe Ser Val
1               5                   10

<210> SEQ ID NO 75
<211> LENGTH: 9
<212> TYPE: PRT
<213> ORGANISM: Human papillomavirus type 45

<400> SEQUENCE: 75

Phe Leu Leu Cys Phe Ser Val Cys Leu
1               5

<210> SEQ ID NO 76
<211> LENGTH: 10
<212> TYPE: PRT
<213> ORGANISM: Artificial
<220> FEATURE:
<223> OTHER INFORMATION: Human papillomavirus type 45-derived epitope

<400> SEQUENCE: 76

Tyr Gln Phe Ala Phe Lys Asp Leu Cys Val
1               5                   10

<210> SEQ ID NO 77
<211> LENGTH: 9
<212> TYPE: PRT
<213> ORGANISM: Artificial
<220> FEATURE:
<223> OTHER INFORMATION: Human papillomavirus type 45-derived epitope

<400> SEQUENCE: 77

Thr Leu Gln Glu Ile Val Leu His Val
1               5

<210> SEQ ID NO 78
<211> LENGTH: 9
<212> TYPE: PRT
<213> ORGANISM: Human papillomavirus type 45

<400> SEQUENCE: 78

Ala Val Met Cys Arg His Tyr Lys Arg
1               5

<210> SEQ ID NO 79
<211> LENGTH: 10
<212> TYPE: PRT
<213> ORGANISM: Human papillomavirus type 45

<400> SEQUENCE: 79

Arg Gln Met Asn Met Ser Gln Trp Ile Lys
1               5                   10

<210> SEQ ID NO 80
<211> LENGTH: 10
<212> TYPE: PRT
<213> ORGANISM: Human papillomavirus type 45

<400> SEQUENCE: 80
```

Ser Thr Trp His Trp Thr Gly Cys Asn Lys
1               5                   10

<210> SEQ ID NO 81
<211> LENGTH: 9
<212> TYPE: PRT
<213> ORGANISM: Human papillomavirus type 45

<400> SEQUENCE: 81

Val Thr Thr Arg Tyr Pro Leu Leu Arg
1               5

<210> SEQ ID NO 82
<211> LENGTH: 10
<212> TYPE: PRT
<213> ORGANISM: Artificial
<220> FEATURE:
<223> OTHER INFORMATION: Human papillomavirus type 45-derived epitope

<400> SEQUENCE: 82

Arg Thr Glu Val Tyr Gln Phe Ala Phe Arg
1               5                   10

<210> SEQ ID NO 83
<211> LENGTH: 9
<212> TYPE: PRT
<213> ORGANISM: Human papillomavirus type 45

<400> SEQUENCE: 83

Ser Val Tyr Gly Glu Thr Leu Glu Lys
1               5

<210> SEQ ID NO 84
<211> LENGTH: 10
<212> TYPE: PRT
<213> ORGANISM: Human papillomavirus type 45

<400> SEQUENCE: 84

Val Phe Thr Phe Pro His Ala Phe Pro Phe
1               5                   10

<210> SEQ ID NO 85
<211> LENGTH: 9
<212> TYPE: PRT
<213> ORGANISM: Human papillomavirus type 45

<400> SEQUENCE: 85

Tyr Tyr Ile Thr Glu Thr Gly Ile Trp
1               5

<210> SEQ ID NO 86
<211> LENGTH: 10
<212> TYPE: PRT
<213> ORGANISM: Human papillomavirus type 45

<400> SEQUENCE: 86

Val Tyr Val Cys Ala Phe Ala Trp Leu Leu
1               5                   10

<210> SEQ ID NO 87
<211> LENGTH: 9
<212> TYPE: PRT
<213> ORGANISM: Human papillomavirus type 45

<400> SEQUENCE: 87

```
Val Tyr Gln Phe Ala Phe Lys Asp Leu
1               5
```

<210> SEQ ID NO 88
<211> LENGTH: 10
<212> TYPE: PRT
<213> ORGANISM: Artificial
<220> FEATURE:
<223> OTHER INFORMATION: Human papillomavirus type 45-derived epitope

<400> SEQUENCE: 88

```
Phe Tyr Ser Arg Ile Arg Glu Leu Arg Phe
1               5                   10
```

<210> SEQ ID NO 89
<211> LENGTH: 15
<212> TYPE: PRT
<213> ORGANISM: Human papillomavirus type 16

<400> SEQUENCE: 89

```
Leu Tyr Trp Tyr Lys Thr Gly Ile Ser Asn Ile Ser Glu Val Tyr
1               5                   10                  15
```

<210> SEQ ID NO 90
<211> LENGTH: 15
<212> TYPE: PRT
<213> ORGANISM: Human papillomavirus type 16

<400> SEQUENCE: 90

```
Pro Glu Trp Ile Gln Arg Gln Thr Val Leu Gln His Ser Phe Asn
1               5                   10                  15
```

<210> SEQ ID NO 91
<211> LENGTH: 15
<212> TYPE: PRT
<213> ORGANISM: Human papillomavirus type 16

<400> SEQUENCE: 91

```
Trp Lys His Met Arg Leu Glu Cys Ala Ile Tyr Tyr Lys Ala Arg
1               5                   10                  15
```

<210> SEQ ID NO 92
<211> LENGTH: 15
<212> TYPE: PRT
<213> ORGANISM: Human papillomavirus type 16

<400> SEQUENCE: 92

```
Leu Gln Ala Ile Glu Leu Gln Leu Thr Leu Glu Thr Ile Tyr Asn
1               5                   10                  15
```

<210> SEQ ID NO 93
<211> LENGTH: 15
<212> TYPE: PRT
<213> ORGANISM: Human papillomavirus type 16

<400> SEQUENCE: 93

```
Gly Leu Tyr Tyr Val His Glu Gly Ile Arg Thr Tyr Phe Val Gln
1               5                   10                  15
```

<210> SEQ ID NO 94
<211> LENGTH: 15
<212> TYPE: PRT
<213> ORGANISM: Human papillomavirus type 16

<400> SEQUENCE: 94

```
Gln Arg Phe His Asn Ile Arg Gly Arg Trp Thr Gly Arg Cys Met
1               5                   10                  15

<210> SEQ ID NO 95
<211> LENGTH: 15
<212> TYPE: PRT
<213> ORGANISM: Human papillomavirus type 16

<400> SEQUENCE: 95

Leu Asp Leu Gln Pro Glu Thr Thr Asp Leu Tyr Cys Tyr Glu Gln
1               5                   10                  15

<210> SEQ ID NO 96
<211> LENGTH: 15
<212> TYPE: PRT
<213> ORGANISM: Human papillomavirus type 16

<400> SEQUENCE: 96

Leu Cys Thr Glu Leu Gln Thr Thr Ile His Asp Ile Ile Leu Glu
1               5                   10                  15

<210> SEQ ID NO 97
<211> LENGTH: 15
<212> TYPE: PRT
<213> ORGANISM: Human papillomavirus type 16

<400> SEQUENCE: 97

Ile Arg Thr Leu Glu Asp Leu Leu Met Gly Thr Leu Gly Ile Val
1               5                   10                  15

<210> SEQ ID NO 98
<211> LENGTH: 15
<212> TYPE: PRT
<213> ORGANISM: Human papillomavirus type 18

<400> SEQUENCE: 98

Phe Lys Thr Leu Ile Gln Pro Phe Ile Leu Tyr Ala His Ile Gln
1               5                   10                  15

<210> SEQ ID NO 99
<211> LENGTH: 15
<212> TYPE: PRT
<213> ORGANISM: Human papillomavirus type 18

<400> SEQUENCE: 99

Ile Glu Phe Ile Thr Phe Leu Gly Ala Leu Lys Ser Phe Leu Lys
1               5                   10                  15

<210> SEQ ID NO 100
<211> LENGTH: 15
<212> TYPE: PRT
<213> ORGANISM: Human papillomavirus type 18

<400> SEQUENCE: 100

Phe Leu Asn Thr Val Ala Ile Pro Asp Ser Val Gln Ile Leu Val
1               5                   10                  15

<210> SEQ ID NO 101
<211> LENGTH: 15
<212> TYPE: PRT
<213> ORGANISM: Human papillomavirus type 18

<400> SEQUENCE: 101

His Lys Ala Ile Glu Leu Gln Met Ala Leu Gln Gly Leu Ala Gln
```

-continued

```
1               5                   10                  15
```

<210> SEQ ID NO 102
<211> LENGTH: 15
<212> TYPE: PRT
<213> ORGANISM: Human papillomavirus type 18

<400> SEQUENCE: 102

```
Glu Val Phe Glu Phe Ala Phe Lys Asp Leu Phe Val Val Tyr Arg
1               5                   10                  15
```

<210> SEQ ID NO 103
<211> LENGTH: 16
<212> TYPE: PRT
<213> ORGANISM: Human papillomavirus type 18

<400> SEQUENCE: 103

```
Leu Phe Val Val Tyr Arg Asp Ser Ile Pro His Ala Ala Cys His Lys
1               5                   10                  15
```

<210> SEQ ID NO 104
<211> LENGTH: 16
<212> TYPE: PRT
<213> ORGANISM: Human papillomavirus type 18

<400> SEQUENCE: 104

```
Thr Asn Thr Gly Leu Tyr Asn Leu Leu Ile Arg Cys Leu Arg Cys Gln
1               5                   10                  15
```

<210> SEQ ID NO 105
<211> LENGTH: 15
<212> TYPE: PRT
<213> ORGANISM: Human papillomavirus type 18

<400> SEQUENCE: 105

```
Phe Gln Gln Leu Phe Leu Asn Thr Leu Ser Phe Val Cys Pro Trp
1               5                   10                  15
```

<210> SEQ ID NO 106
<211> LENGTH: 15
<212> TYPE: PRT
<213> ORGANISM: Human papillomavirus type 31

<400> SEQUENCE: 106

```
Asn Gly Trp Phe Tyr Val Glu Ala Val Ile Asp Arg Gln Thr Gly
1               5                   10                  15
```

<210> SEQ ID NO 107
<211> LENGTH: 15
<212> TYPE: PRT
<213> ORGANISM: Human papillomavirus type 31

<400> SEQUENCE: 107

```
Pro Glu Trp Ile Glu Arg Gln Thr Val Leu Gln His Ser Phe Asn
1               5                   10                  15
```

<210> SEQ ID NO 108
<211> LENGTH: 15
<212> TYPE: PRT
<213> ORGANISM: Human papillomavirus type 31

<400> SEQUENCE: 108

```
Trp Lys His Ile Arg Leu Glu Cys Val Leu Met Tyr Lys Ala Arg
1               5                   10                  15
```

```
<210> SEQ ID NO 109
<211> LENGTH: 15
<212> TYPE: PRT
<213> ORGANISM: Human papillomavirus type 31

<400> SEQUENCE: 109

Thr Thr Pro Ile Ile His Leu Lys Gly Asp Ala Asn Ile Leu Lys
1               5                   10                  15

<210> SEQ ID NO 110
<211> LENGTH: 15
<212> TYPE: PRT
<213> ORGANISM: Human papillomavirus type 31

<400> SEQUENCE: 110

Thr Gly Arg Cys Ile Ala Cys Trp Arg Arg Pro Arg Thr Glu Thr
1               5                   10                  15

<210> SEQ ID NO 111
<211> LENGTH: 15
<212> TYPE: PRT
<213> ORGANISM: Human papillomavirus type 31

<400> SEQUENCE: 111

Val Leu Asp Phe Ala Phe Thr Asp Leu Thr Ile Val Tyr Arg Asp
1               5                   10                  15

<210> SEQ ID NO 112
<211> LENGTH: 15
<212> TYPE: PRT
<213> ORGANISM: Human papillomavirus type 31

<400> SEQUENCE: 112

Ile Arg Ile Leu Gln Glu Leu Leu Met Gly Ser Phe Gly Ile Val
1               5                   10                  15

<210> SEQ ID NO 113
<211> LENGTH: 15
<212> TYPE: PRT
<213> ORGANISM: Human papillomavirus type 31

<400> SEQUENCE: 113

Pro Arg Lys Leu His Glu Leu Ser Ser Ala Leu Glu Ile Pro Tyr
1               5                   10                  15

<210> SEQ ID NO 114
<211> LENGTH: 17
<212> TYPE: PRT
<213> ORGANISM: Human papillomavirus type 45

<400> SEQUENCE: 114

Asp Trp Val Met Ala Ile Phe Gly Val Asn Pro Thr Val Ala Glu Gly
1               5                   10                  15
Phe

<210> SEQ ID NO 115
<211> LENGTH: 15
<212> TYPE: PRT
<213> ORGANISM: Human papillomavirus type 45

<400> SEQUENCE: 115

Phe Lys Thr Leu Ile Lys Pro Ala Thr Leu Tyr Ala His Ile Gln
1               5                   10                  15
```

```
<210> SEQ ID NO 116
<211> LENGTH: 15
<212> TYPE: PRT
<213> ORGANISM: Human papillomavirus type 45

<400> SEQUENCE: 116

Pro Ile Asn Ile Ser Lys Ser Lys Ala His Lys Ala Ile Glu Leu
1               5                   10                  15

<210> SEQ ID NO 117
<211> LENGTH: 15
<212> TYPE: PRT
<213> ORGANISM: Human papillomavirus type 45

<400> SEQUENCE: 117

Thr Ile Pro Asn Ser Val Gln Ile Ser Val Gly Tyr Met Thr Ile
1               5                   10                  15

<210> SEQ ID NO 118
<211> LENGTH: 15
<212> TYPE: PRT
<213> ORGANISM: Human papillomavirus type 45

<400> SEQUENCE: 118

Leu Cys Ile Val Tyr Arg Asp Cys Ile Ala Tyr Ala Ala Cys His
1               5                   10                  15

<210> SEQ ID NO 119
<211> LENGTH: 15
<212> TYPE: PRT
<213> ORGANISM: Human papillomavirus type 45

<400> SEQUENCE: 119

Phe His Ser Ile Ala Gly Gln Tyr Arg Gly Gln Cys Asn Thr Cys
1               5                   10                  15

<210> SEQ ID NO 120
<211> LENGTH: 15
<212> TYPE: PRT
<213> ORGANISM: Human papillomavirus type 45

<400> SEQUENCE: 120

Glu Ile Val Leu His Leu Glu Pro Gln Asn Glu Leu Asp Pro Val
1               5                   10                  15

<210> SEQ ID NO 121
<211> LENGTH: 15
<212> TYPE: PRT
<213> ORGANISM: Human papillomavirus type 45

<400> SEQUENCE: 121

Leu Arg Thr Leu Gln Gln Leu Phe Leu Ser Thr Leu Ser Phe Val
1               5                   10                  15

<210> SEQ ID NO 122
<211> LENGTH: 13
<212> TYPE: PRT
<213> ORGANISM: Artificial
<220> FEATURE:
<223> OTHER INFORMATION: PADRE universal T cell epitope

<400> SEQUENCE: 122

Ala Lys Phe Val Ala Ala Trp Thr Leu Lys Ala Ala Ala
1               5                   10
```

<210> SEQ ID NO 123
<211> LENGTH: 894
<212> TYPE: PRT
<213> ORGANISM: Artificial
<220> FEATURE:
<223> OTHER INFORMATION: Human papillomavirus polyepitope construct

<400> SEQUENCE: 123

```
Met Gly Met Gln Val Gln Ile Gln Ser Leu Phe Leu Leu Leu Leu Trp
1               5                   10                  15

Val Pro Gly Ser Arg Gly Ala Phe Thr Asp Leu Thr Ile Val Tyr Asn
            20                  25                  30

Ser Thr Trp His Trp Thr Gly Cys Asn Lys Ala Ala Ala Lys Leu
        35                  40                  45

Leu Glu Lys Leu Leu Cys Ile Asn Ala Tyr Gln Phe Ala Phe Lys Asp
    50                  55                  60

Leu Cys Val Lys Met Val Met Leu Met Leu Val Arg Phe Lys Asn Ala
65                  70                  75                  80

Ala Leu Gln Asp Lys Ile Leu Asp His Tyr Lys Ala Ala Phe Leu Leu
                85                  90                  95

Cys Phe Cys Val Leu Leu Asn Ser Val Tyr Gly Thr Thr Leu Glu Arg
            100                 105                 110

Asn Ala Ala Val Thr Thr Arg Tyr Pro Leu Leu Arg Asn Ala Thr Leu
        115                 120                 125

Gln Glu Ile Val Leu His Val Asn Tyr Tyr Ile Thr Glu Thr Gly Ile
130                 135                 140

Trp Lys Val Val Phe Ile Tyr Ile Pro Leu Phe Asn Gln Thr Glu Pro
145                 150                 155                 160

Asp Thr Ser Asn Tyr Gly Ala Ala Glu Leu Asp Pro Val Asp Leu Leu
                165                 170                 175

Cys Tyr Lys Ala Ala Ala Leu Thr Asp Val Ser Ile Ala Cys Val Tyr
            180                 185                 190

Asn Ala Ala Arg Thr Glu Val Tyr Gln Phe Ala Phe Arg Asn Pro Tyr
        195                 200                 205

Leu His Ser Arg Leu Val Val Phe Asn Ile Ser Phe Ala Gly Ile Val
210                 215                 220

Thr Lys Lys Val Met Asp Asp Ser Glu Ile Ala Tyr Asn Ala Phe Tyr
225                 230                 235                 240

Ser Arg Ile Arg Glu Leu Arg Phe Lys Ala Ala Ala Phe Ile Tyr Ile
                245                 250                 255

Pro Leu Phe Val Ile Lys Ala Val Phe Thr Phe Pro His Ala Phe Pro
            260                 265                 270

Phe Asn Ala Phe Tyr Ser Lys Val Ser Glu Phe Arg Trp Lys Ser Leu
        275                 280                 285

Val Phe Leu Leu Cys Phe Ser Val Asn Ala Ser Thr Ala Ala Ala Leu
290                 295                 300

Tyr Trp Tyr Arg Lys Ala Thr Leu Tyr Ala His Ile Gln Cys Leu Asn
305                 310                 315                 320

Ala Ala His Tyr Thr Asn Trp Lys Phe Ile Phe Asn Ala Ala Asn Thr
                325                 330                 335

Glu Leu Tyr Asn Leu Leu Ile Asn Ala Ser Tyr Phe Gly Met Ser Phe
            340                 345                 350

Ile His Phe Lys Leu Thr Asn Lys Gly Ile Cys Asp Leu Asn Ser Val
        355                 360                 365
```

```
Tyr Gly Glu Thr Leu Glu Lys Asn Val Tyr Val Cys Ala Phe Ala Trp
    370                 375                 380

Leu Leu Asn Val Tyr Gly Thr Thr Leu Glu Lys Leu Lys Leu Ser Gln
385                 390                 395                 400

Met Val Gln Trp Ala Tyr Lys Ala Ala Tyr Val Val Trp Asp Ser
                405                 410                 415

Ile Tyr Tyr Ile Asn Gly Thr Gly Cys Asn Gly Trp Phe Tyr Gly Ala
                420                 425                 430

Ala Ala Val Met Cys Arg His Tyr Lys Arg Asn Phe Leu Leu Cys Phe
            435                 440                 445

Ser Val Cys Leu Asn Ala Val Tyr Gln Phe Ala Phe Lys Asp Leu Lys
450                 455                 460

Ala Ala Lys Val Ser Glu Phe Arg Trp Tyr Arg Tyr Lys Tyr Thr Asn
465                 470                 475                 480

Trp Lys Phe Ile Tyr Leu Asn Ala Ala Leu Ser Ser Ala Leu Glu Ile
                485                 490                 495

Pro Tyr Lys Ala Ala Phe Leu Phe Thr Asp Leu Thr Ile Val Asn Ala
                500                 505                 510

Ala Thr Thr Pro Ile Ile His Leu Lys Asn Ala Ala Arg Gln Met
            515                 520                 525

Asn Met Ser Gln Trp Ile Lys Asn Thr Gly Ile Leu Thr Val Thr Tyr
530                 535                 540

Asn Val Phe Thr Phe Pro Asn Pro Phe Pro Phe Lys Ala Ala Ala Glu
545                 550                 555                 560

Ile Val Leu His Leu Glu Pro Gln Asn Glu Leu Asp Pro Val Gly Pro
                565                 570                 575

Gly Pro Gly Ile Arg Ile Leu Gln Glu Leu Leu Met Gly Ser Phe Gly
                580                 585                 590

Ile Val Gly Pro Gly Pro Gly Thr Gly Arg Cys Ile Ala Cys Trp Arg
                595                 600                 605

Arg Pro Arg Thr Glu Thr Gly Pro Gly Pro Gly Trp Lys His Ile Arg
            610                 615                 620

Leu Glu Cys Val Leu Met Tyr Lys Ala Arg Gly Pro Gly Pro Gly Leu
625                 630                 635                 640

Cys Ile Val Tyr Arg Asp Cys Ile Ala Tyr Ala Ala Cys His Gly Pro
                645                 650                 655

Gly Pro Gly Pro Glu Trp Ile Glu Arg Gln Thr Val Leu Gln His Ser
                660                 665                 670

Phe Asn Gly Pro Gly Pro Gly Pro Ile Asn Ile Ser Lys Ser Lys Ala
                675                 680                 685

His Lys Ala Ile Glu Leu Gly Pro Gly Pro Gly Leu Arg Thr Leu Gln
            690                 695                 700

Gln Leu Phe Leu Ser Thr Leu Ser Phe Val Gly Pro Gly Pro Gly Phe
705                 710                 715                 720

His Ser Ile Ala Gly Gln Tyr Arg Gly Gln Cys Asn Thr Cys Gly Pro
                725                 730                 735

Gly Pro Gly Thr Thr Pro Ile Ile His Leu Lys Gly Asp Ala Asn Ile
                740                 745                 750

Leu Lys Gly Pro Gly Pro Gly Asp Trp Val Met Ala Ile Phe Gly Val
            755                 760                 765

Asn Pro Thr Val Ala Glu Gly Phe Gly Pro Gly Pro Gly Pro Arg Lys
770                 775                 780

Leu His Glu Leu Ser Ser Ala Leu Glu Ile Pro Tyr Gly Pro Gly Pro
```

```
                   785                 790                 795                 800
Gly Phe Lys Thr Leu Ile Lys Pro Ala Thr Leu Tyr Ala His Ile Gln
                805                 810                 815

Gly Pro Gly Pro Gly Thr Ile Pro Asn Ser Val Gln Ile Ser Val Gly
                820                 825                 830

Tyr Met Thr Ile Gly Pro Gly Pro Gly Asn Gly Trp Phe Tyr Val Glu
                835                 840                 845

Ala Val Ile Asp Arg Gln Thr Gly Gly Pro Gly Pro Gly Val Leu Asp
850                 855                 860

Phe Ala Phe Thr Asp Leu Thr Ile Val Tyr Arg Asp Gly Pro Gly Pro
865                 870                 875                 880

Gly Ala Lys Phe Val Ala Ala Trp Thr Leu Lys Ala Ala Ala
                885                 890

<210> SEQ ID NO 124
<211> LENGTH: 2685
<212> TYPE: DNA
<213> ORGANISM: artificial
<220> FEATURE:
<223> OTHER INFORMATION: Human papillomavirus polyepitope construct

<400> SEQUENCE: 124
atgggcatgc aggtgcagat ccagagcctg ttcctgctgc tgctgtgggt gcccggcagc      60
aggggcgctt tcaccgacct gaccatcgtg tacaacagca cctggcactg gaccggctgc     120
aacaagaaag ccgctgccaa gctgctggaa aagctgctgt gcatcaacgc ctatcagttt     180
gccttcaagg acctgtgcgt gaagatggtg atgctgatgc tggtgcggtt caagaatgcc     240
gctctccagg acaagatcct ggaccactac aaggccgcct ttctgctgtg cttctgcgtg     300
ctgctgaaca cgctgtacgg caccaccctg aacggaacg ccgccgtgac caccagatac     360
cccctgctgc ggaatgccac cctccaggaa atcgtcctgc acgtcaatta ctacatcacc     420
gagaccggca tctggaaggt ggtgttcatc tacatccccc tgttcaacca gaccgagccc     480
gacaccagca actacggagc cgccgaactc gatccgtgg acctgctgtg ctacaaagcc     540
gctgccctga ccgacgtgag catcgcctgc gtgtacaacg ccgccaggac cgaggtgtac     600
cagtttgcct tcggaaccc ctacctgcac agcagactgg tggtgtttaa catcagcttc     660
gccggcatcg tgaccaagaa agtgatggac acagcgaga tcgcctacaa cgccttctac     720
agccggatca gagagctgag gttcaaagcc gctgccttta tctacattcc tctgttcgtg     780
atcaaggccg tgttcaccttt cccccacgcc ttccctttca atgccttcta ctccaaggtg     840
tccgagttcc ggtggaagag cctggtgttc ctgctgtgtt tcagcgtgaa cgccagcacc     900
gccgctgccc tgtactggta caggaaggcc accctgtacg cccatatcca gtgcctgaat     960
gccgcccact acaccaactg gaagttcatc ttcaatgccg ccaacaccga gctgtacaac    1020
ctgctgatca cgccagcta cttcggcatg agcttcatcc acttcaagct gaccaacaag    1080
ggcatctgcg acctgaactc cgtgtacggc gagacactgg aaaagaacgt gtacgtgtgc    1140
gccttcgcct ggctgctgaa cgtgtatggc acaacactgg aaaaactgaa gctgtcccag    1200
atggtgcagt gggcctataa agccgccgcc tacgtggtgt gggacagcat ctactatatc    1260
aacggcaccg gctgtaacgg ctggttttac ggcgccgctg ccgtgatgtg ccggcactac    1320
aagcggaatt ttctgctgtg tttttccgtg tgcctgaacg ccgtgtatca gttcgccttt    1380
aaggatctga aggctgccaa agtgtctgag ttcagatggt acaggtacaa gtacacaaat    1440
tggaagttta tctatctgaa cgccgccctg agcagcgccc tggaaatccc ctataaggct    1500
```

```
gccttcctgt tcaccgatct gactattgtg aacgccgcca ccaccccat catccacctg    1560 aaaaacgccg ctgccaggca gatgaacatg agccagtgga tcaagaacac cggcatcctg    1620
accgtgacct acaacgtgtt tacctttccc aaccctttcc cctttaaagc cgctgccgag    1680
atcgtgctgc acctggaacc ccagaacgag ctggaccctg tgggccctgg ccctggcatc    1740
agaatcctcc aggaactgct gatgggcagc ttcggcatcg tgggcccagg ccccggaacc    1800
ggccggtgca tcgcctgttg gcggaggccc cggaccgaga caggccctgg accccggctgg    1860 aagcacatcc ggctggaatg cgtgctgatg tacaaggcca ggggacccgg ccctggcctc    1920
tgtatcgtgt accgcgactg catcgcctac gccgcctgcc acggcccagg acctggcccc    1980
gagtggatcg agcggcagac cgtgctccag catagcttca acggaccccgg accaggcccc    2040 atcaacatca gcaagagcaa ggcccacaag gccatcgagc tgggccctgg gcccggactg    2100
cggaccctcc agcagctgtt cctgagcacc ctgagcttcg tgggacctgg gccaggcttc    2160
cacagcatcg ccggccagta ccggggccag tgcaacacct gcggcccagg gccaggcacc    2220
acacctatta ttcacctgaa gggcgacgcc aacatcctga aggggccagg acccggcgac    2280
tgggtgatgg ccatcttcgg cgtgaacccc accgtggccg agggcttcgg acctggacct    2340
gggcctagga agctgcacga gctgtcctct gccctggaaa ttccttacgg ccctggccca    2400
ggcttcaaga ccctgatcaa gcccgccaca ctgtatgccc acattcaggg ccctggacca    2460
ggcaccatcc ccaacagcgt gcagatcagc gtgggctaca tgaccatcgg accagggcct    2520
ggcaatggct ggttctacgt ggaggccgtg atcgacaggc agaccggcgg acctggccca    2580
ggggtgctgg acttcgcctt tacagacctg acaattgtgt accgggacgg ccctgggcct    2640
ggcgccaagt tcgtggccgc ctggaccctg aaggccgctg cctga                     2685
```

<210> SEQ ID NO 125
<211> LENGTH: 894
<212> TYPE: PRT
<213> ORGANISM: Artificial
<220> FEATURE:
<223> OTHER INFORMATION: Human papillomavirus polyepitope construct

<400> SEQUENCE: 125

```
Met Gly Met Gln Val Gln Ile Gln Ser Leu Phe Leu Leu Leu Leu Trp
1               5                   10                  15

Val Pro Gly Ser Arg Gly Phe Tyr Ser Lys Val Ser Glu Phe Arg Trp
            20                  25                  30

Lys Ala Ala Arg Thr Glu Val Tyr Gln Phe Ala Phe Arg Asn Ala Ala
        35                  40                  45

Val Thr Thr Arg Tyr Pro Leu Leu Arg Asn Val Phe Thr Phe Pro Asn
    50                  55                  60

Pro Phe Pro Phe Asn Tyr Thr Asn Trp Lys Phe Ile Tyr Leu Asn Ala
65                  70                  75                  80

Ser Val Tyr Gly Glu Thr Leu Glu Lys Gly Ala Ala Val Met Cys Arg
                85                  90                  95

His Tyr Lys Arg Asn Ala Val Tyr Gly Thr Thr Leu Glu Lys Leu Lys
            100                 105                 110

Val Val Phe Ile Tyr Ile Pro Leu Phe Gly Ala Ala Lys Leu Leu Glu
        115                 120                 125

Lys Leu Leu Cys Ile Asn Gly Thr Gly Cys Asn Gly Trp Phe Tyr Asn
    130                 135                 140

Gln Thr Glu Pro Asp Thr Ser Asn Tyr Asn Ala Ala Ala Pro Tyr Leu
```

-continued

```
            145                 150                 155                 160
        His Ser Arg Leu Val Val Phe Gly Ala Ala Leu Thr Asp Val Ser
                        165                 170                 175
        Ile Ala Cys Val Tyr Asn Ala His Tyr Thr Asn Trp Lys Phe Ile Phe
                        180                 185                 190
        Gly Ala Ala Phe Ile Tyr Ile Pro Leu Phe Val Ile Lys Ala Ala Ala
                        195                 200                 205
        Met Val Met Leu Met Leu Val Arg Phe Lys Asn Ala Ala Asn Thr Glu
        210                 215                 220
        Leu Tyr Asn Leu Leu Ile Asn Phe Leu Phe Thr Asp Leu Thr Ile Val
        225                 230                 235                 240
        Asn Phe Leu Leu Cys Phe Cys Val Leu Leu Asn Ala Ala Thr Thr Pro
                        245                 250                 255
        Ile Ile His Leu Lys Gly Ala Ala Lys Leu Thr Asn Lys Gly Ile Cys
                        260                 265                 270
        Asp Leu Asn Ala Leu Gln Asp Lys Ile Leu Asp His Tyr Lys Asn Thr
                        275                 280                 285
        Gly Ile Leu Thr Val Thr Tyr Gly Ala Ala Ala Val Met Asp Asp Ser
                        290                 295                 300
        Glu Ile Ala Tyr Asn Ser Thr Trp His Trp Thr Gly Cys Asn Lys Lys
        305                 310                 315                 320
        Ala Ala Ser Tyr Phe Gly Met Ser Phe Ile His Phe Lys Leu Ser Ser
                        325                 330                 335
        Ala Leu Glu Ile Pro Tyr Lys Leu Ser Gln Met Val Gln Trp Ala Tyr
                        340                 345                 350
        Asn Ser Leu Val Phe Leu Leu Cys Phe Ser Val Asn Ala Thr Leu Tyr
                        355                 360                 365
        Ala His Ile Gln Cys Leu Asn Val Phe Thr Phe Pro His Ala Phe Pro
                        370                 375                 380
        Phe Asn Ala Ala Ala Arg Gln Met Asn Met Ser Gln Trp Ile Lys Asn
        385                 390                 395                 400
        Ala Thr Leu Gln Glu Ile Val Leu His Val Asn Ala Ala Phe Thr Asp
                        405                 410                 415
        Leu Thr Ile Val Tyr Asn Ile Ser Phe Ala Gly Ile Val Thr Lys Lys
                        420                 425                 430
        Tyr Val Val Trp Asp Ser Ile Tyr Tyr Ile Asn Tyr Tyr Ile Thr Glu
                        435                 440                 445
        Thr Gly Ile Trp Lys Ala Ala Ala Phe Tyr Ser Arg Ile Arg Glu Leu
                        450                 455                 460
        Arg Phe Lys Val Tyr Gln Phe Ala Phe Lys Asp Leu Lys Ala Phe Leu
        465                 470                 475                 480
        Leu Cys Phe Ser Val Cys Leu Asn Ala Ala Tyr Gln Phe Ala Phe Lys
                        485                 490                 495
        Asp Leu Cys Val Lys Ser Val Tyr Gly Thr Thr Leu Glu Arg Asn Lys
                        500                 505                 510
        Val Ser Glu Phe Arg Trp Tyr Arg Tyr Lys Ala Ala Glu Leu Asp Pro
                        515                 520                 525
        Val Asp Leu Leu Cys Tyr Lys Ser Thr Ala Ala Ala Leu Tyr Trp Tyr
                        530                 535                 540
        Arg Lys Ala Ala Ala Val Tyr Val Cys Ala Phe Ala Trp Leu Leu Glu
        545                 550                 555                 560
        Ile Val Leu His Leu Glu Pro Gln Asn Glu Leu Asp Pro Val Gly Pro
                        565                 570                 575
```

```
Gly Pro Gly Ile Arg Ile Leu Gln Glu Leu Met Gly Ser Phe Gly
            580                 585                 590

Ile Val Gly Pro Gly Pro Gly Thr Gly Arg Cys Ile Ala Cys Trp Arg
        595                 600                 605

Arg Pro Arg Thr Glu Thr Gly Pro Gly Pro Gly Trp Lys His Ile Arg
610                 615                 620

Leu Glu Cys Val Leu Met Tyr Lys Ala Arg Gly Pro Gly Pro Gly Leu
625                 630                 635                 640

Cys Ile Val Tyr Arg Asp Cys Ile Ala Tyr Ala Ala Cys His Gly Pro
                645                 650                 655

Gly Pro Gly Pro Glu Trp Ile Glu Arg Gln Thr Val Leu Gln His Ser
            660                 665                 670

Phe Asn Gly Pro Gly Pro Gly Pro Ile Asn Ile Ser Lys Ser Lys Ala
        675                 680                 685

His Lys Ala Ile Glu Leu Gly Pro Gly Pro Gly Leu Arg Thr Leu Gln
690                 695                 700

Gln Leu Phe Leu Ser Thr Leu Ser Phe Val Gly Pro Gly Pro Gly Phe
705                 710                 715                 720

His Ser Ile Ala Gly Gln Tyr Arg Gly Gln Cys Asn Thr Cys Gly Pro
                725                 730                 735

Gly Pro Gly Thr Thr Pro Ile Ile His Leu Lys Gly Asp Ala Asn Ile
            740                 745                 750

Leu Lys Gly Pro Gly Pro Gly Asp Trp Val Met Ala Ile Phe Gly Val
        755                 760                 765

Asn Pro Thr Val Ala Glu Gly Phe Gly Pro Gly Pro Gly Pro Arg Lys
770                 775                 780

Leu His Glu Leu Ser Ser Ala Leu Glu Ile Pro Tyr Gly Pro Gly Pro
785                 790                 795                 800

Gly Phe Lys Thr Leu Ile Lys Pro Ala Thr Leu Tyr Ala His Ile Gln
                805                 810                 815

Gly Pro Gly Pro Gly Thr Ile Pro Asn Ser Val Gln Ile Ser Val Gly
            820                 825                 830

Tyr Met Thr Ile Gly Pro Gly Pro Gly Asn Gly Trp Phe Tyr Val Glu
        835                 840                 845

Ala Val Ile Asp Arg Gln Thr Gly Gly Pro Gly Pro Gly Val Leu Asp
850                 855                 860

Phe Ala Phe Thr Asp Leu Thr Ile Val Tyr Arg Asp Gly Pro Gly Pro
865                 870                 875                 880

Gly Ala Lys Phe Val Ala Ala Trp Thr Leu Lys Ala Ala Ala
                885                 890
```

<210> SEQ ID NO 126
<211> LENGTH: 2685
<212> TYPE: DNA
<213> ORGANISM: artificial
<220> FEATURE:
<223> OTHER INFORMATION: Human papillomavirus polyepitope construct

<400> SEQUENCE: 126

```
atgggcatgc aggtgcagat ccagagcctg ttcctgctgc tgctgtgggt gcccggcagc    60
cggggcttct acagcaaggt gtccgagttc cggtggaagg ccgccaggac cgaggtgtac   120
cagttcgcct tccggaacgc cgccgtgacc accagatacc ccctgctgcg gaacgtgttc   180
accttcccca ccccttccc tttcaactac accaactgga agttcatcta cctgaacgcc   240
```

-continued

| | |
|---|---|
| agcgtgtacg gcgagaccct ggaaaaggga gcagccgtga tgtgccggca ctacaagcgg | 300 |
| aacgccgtgt acggcaccac actggaaaag ctgaaggtgg tgttcatcta catcccctg | 360 |
| ttcggagccg ccaagctgct ggaaaaactg ctgtgcatca acggcaccgg ctgcaacggc | 420 |
| tggttctaca accagaccga gcccgacacc agcaactaca atgctgccgc ccctacctg | 480 |
| cacagcagac tggtggtgtt tggggctgcc gccctgaccg acgtgagcat cgcctgcgtg | 540 |
| tacaacgccc actacacaaa ttggaaattc attttggag ccgccttcat ctatattcct | 600 |
| ctgttcgtga tcaaagccgc cgctatggtg atgctgatgc tggtgcggtt caagaacgcc | 660 |
| gccaacaccg agctgtacaa cctgctgatc aacttcctgt tcaccgacct gaccatcgtg | 720 |
| aactttctcc tgtgtttctg cgtgctcctg aatgccgcca caccccat catccacctg | 780 |
| aagggagccg ccaaactgac caacaagggc atctgcgacc tgaatgccct ccaggacaag | 840 |
| atcctggacc actacaagaa caccggcatc ctgaccgtga cctatggagc cgctgccgtg | 900 |
| atggacgaca gcgagatcgc ctacaacagc acctggcact ggaccggctg taacaagaag | 960 |
| gccgcctcct acttcggcat gagcttcatc cacttcaagc tgtccagcgc cctggaaatc | 1020 |
| ccctacaagc tgtcccagat ggtgcagtgg gcctacaact ccctggtgtt cctgctgtgt | 1080 |
| ttcagcgtga acgcaaccct ctatgccac atccagtgcc tgaatgtgtt taccttccct | 1140 |
| cacgcctttc ccttcaatgc cgccgccaga cagatgaaca tgagccagtg gatcaagaat | 1200 |
| gccaccctcc aggagattgt cctgcacgtc aatgccgcct ttactgatct gactatcgtg | 1260 |
| tacaacatca gcttcgccgg catcgtgacc aagaaatacg tggtgtggga cagcatctac | 1320 |
| tacatcaatt actacatcac cgagaccggc atctggaaag ctgccgcctt ctacagccgg | 1380 |
| atcagggagc tgaggttcaa agtgtatcag tttgctttca aagacctgaa agccttcctg | 1440 |
| ctgtgctttt ccgtgtgcct gaacgccgcc taccagtttg cctttaagga tctgtgcgtg | 1500 |
| aagagcgtgt atggcacaac cctggaacgg aacaaagtgt ctgagttccg ctggtacagg | 1560 |
| tataaggccg ccgaactcga tcccgtggat ctgctgtgtt acaagagcac tgccgccgca | 1620 |
| ctgtactggt ataggaaggc tgccgccgtg tacgtgtgcg ccttcgcctg gctgctggag | 1680 |
| atcgtgctgc acctggaacc ccagaacgag ctggaccctg tgggccctgg ccctggcatc | 1740 |
| agaatcctcc aggaactgct gatgggcagc ttcggcatcg tgggcccagg ccccggaacc | 1800 |
| ggccggtgca tcgcctgttg gcggaggccc cggaccgaga caggccctgg acccggctgg | 1860 |
| aagcacatcc ggctggaatg cgtgctgatg tacaaggcca ggggaccgg ccctggcctc | 1920 |
| tgtatcgtgt accgcgactg catcgcctac gccgctgcc acgcccagg acctggcccc | 1980 |
| gagtggatcg agcggcagac cgtgctccag catagcttca acggaccgg accaggcccc | 2040 |
| atcaacatca gcaagagcaa ggcccacaag gccatcgagc tgggccctgg gcccggactg | 2100 |
| cggaccctcc agcagctgtt cctgagcacc ctgagcttcg tgggacctgg gccaggcttc | 2160 |
| cacagcatcg ccggccagta ccggggccag tgcaacacct gcggcccagg gcaggcacc | 2220 |
| acacctatta ttcacctgaa gggcgacgcc aacatcctga ggggccagg acccggcgac | 2280 |
| tgggtgatgg ccatcttcgg cgtgaacccc accgtggccg agggcttcgg acctggacct | 2340 |
| gggcctagga gctgcacga gctgtcctct gccctggaaa ttccttacgg ccctggccca | 2400 |
| ggcttcaaga ccctgatcaa gcccgccaca ctgtatgccc acattcaggg ccctggacca | 2460 |
| ggcaccatcc ccaacagcgt gcagatcagc gtgggctaca tgaccatcgg accagggcct | 2520 |
| ggcaatggct ggttctacgt ggaggccgtg atcgacaggc agaccggcgg acctggccca | 2580 |
| ggggtgctgg acttcgcctt tacagacctg acaattgtgt accgggacgg ccctgggcct | 2640 | ggcgccaagt tcgtggccgc ctggaccctg aaggccgctg cctga 2685

<210> SEQ ID NO 127
<211> LENGTH: 891
<212> TYPE: PRT
<213> ORGANISM: Artificial
<220> FEATURE:
<223> OTHER INFORMATION: Human papillomavirus polyepitope construct

<400> SEQUENCE: 127

```
Met Gly Met Gln Val Gln Ile Gln Ser Leu Phe Leu Leu Leu Leu Trp
1               5                   10                  15

Val Pro Gly Ser Arg Gly Lys Ser Leu Phe Gly Met Ser Leu Met Lys
            20                  25                  30

Asn Ser Thr Ala Ala Ala Leu Tyr Trp Tyr Lys Lys Ala Ala Cys Tyr
        35                  40                  45

Ser Leu Tyr Gly Thr Thr Phe Lys Ala Ala Val Ala Trp Asp Ser
    50                  55                  60

Val Tyr Tyr Met Lys Ser Thr Asp Leu Arg Asp His Ile Asp Tyr Asn
65                  70                  75                  80

Ile Ser Asp Tyr Arg His Tyr Cys Tyr Lys Ala Ala Gln Val Val Pro
                85                  90                  95

Ala Tyr Asn Ile Ser Lys Asn Gly Tyr Asn Thr Phe Tyr Ile Glu Phe
            100                 105                 110

Lys Leu Gln Asp Lys Ile Ile Asp His Tyr Lys Ala Ala Cys Leu Tyr
        115                 120                 125

Leu His Ile Gln Ser Leu Asn Ala Ala Ala Thr Leu Gln Asp Ile
    130                 135                 140

Val Leu His Gly Thr Val Tyr Val Phe Cys Phe Leu Leu Asn Ala Ile
145                 150                 155                 160

Leu Tyr Ala His Ile Gln Cys Leu Asn Ala Ala Leu Tyr Asn Leu Leu
                165                 170                 175

Ile Arg Cys Phe Lys Ala Ala Phe Val Tyr Ile Pro Leu Phe Leu Ile
            180                 185                 190

Asn Thr Val Ser Ala Thr Gln Leu Val Lys Asn Gly Thr Gly Cys Asn
        195                 200                 205

Gly Trp Phe Tyr Asn Ala Ala Thr Lys Tyr Pro Leu Leu Lys Asn Val
    210                 215                 220

Tyr Val Phe Cys Phe Leu Leu Pro Met Asn Ala Thr Leu His Asp Ile
225                 230                 235                 240

Ile Leu Glu Cys Val Lys Ala Ala Ala Leu Tyr Gly Val Ser Phe Ser
                245                 250                 255

Glu Leu Lys Gln Val Asp Tyr Tyr Gly Leu Tyr Tyr Gly Ala Tyr Tyr
            260                 265                 270

Met Thr Asp Ala Gly Thr Trp Asn Ala Ala Pro Tyr Ala Val Cys Asp
        275                 280                 285

Lys Cys Phe Lys Gln Gly Ala Met Leu Ala Val Phe Lys Lys Ala Ala
    290                 295                 300

Ala Val Val Leu Leu Leu Val Arg Tyr Lys Asn Ala Ala Ala Ser Tyr
305                 310                 315                 320

Phe Gly Met Ser Phe Ile His Phe Lys Ala Ala Lys Leu Leu Ser Lys
                325                 330                 335

Leu Leu Cys Val Asn Ala Ala Ala Ala Thr Met Cys Arg His Tyr Lys
            340                 345                 350
```

```
Arg Asn Ala Ala Ala Ser Thr Val Ser Val Gly Thr Ala Lys Asn Ala
            355                 360                 365

Ala Leu Ser Gln Met Val Gln Trp Ala Tyr Lys Leu Thr Asn Thr Gly
    370                 375                 380

Leu Tyr Asn Val Asn Ala Ala Thr Cys Val Ser His Arg Gly Leu
385                 390                 395                 400

Tyr Asn Ala Ala Lys Ser Ala Ile Val Thr Leu Thr Tyr Lys Ala Ala
                405                 410                 415

Ala Asp Ser Val Tyr Gly Asp Thr Leu Glu Arg Asn Met Tyr Val Cys
            420                 425                 430

Cys His Val Pro Leu Asn Ala Ala Arg Phe His Asn Ile Arg Gly Arg
        435                 440                 445

Phe Lys Ala Ala Phe Val Val Tyr Arg Asp Ser Ile Pro Lys Asn Ala
    450                 455                 460

Ser Leu Gln Asp Ile Glu Ile Thr Cys Val Lys Ala Val Tyr Asp Phe
465                 470                 475                 480

Ala Phe Arg Asp Leu Cys Ile Lys Tyr Met Leu Asp Leu Gln Pro Glu
                485                 490                 495

Thr Val Asn Ala Ala Gly Thr Leu Gly Ile Val Cys Pro Val Asn
            500                 505                 510

Ser Val Ile Cys Phe Val Asn Ser Lys Asn Ala Thr Leu Glu Lys Leu
    515                 520                 525

Thr Asn Thr Gly Leu Tyr Asn Ala Gly Leu Tyr Tyr Val His Glu Gly
    530                 535                 540

Ile Arg Thr Tyr Phe Val Gln Gly Pro Gly Pro Gly Phe Leu Asn Thr
545                 550                 555                 560

Val Ala Ile Pro Asp Ser Val Gln Ile Leu Val Gly Pro Gly Pro Gly
                565                 570                 575

Gln Arg Phe His Asn Ile Arg Gly Arg Trp Thr Gly Arg Cys Met Gly
            580                 585                 590

Pro Gly Pro Gly Thr Asn Thr Gly Leu Tyr Asn Leu Leu Ile Arg Cys
        595                 600                 605

Leu Arg Cys Gln Gly Pro Gly Pro Gly Ile Glu Phe Ile Thr Phe Leu
    610                 615                 620

Gly Ala Leu Lys Ser Phe Leu Lys Gly Pro Gly Pro Gly Pro Glu Trp
625                 630                 635                 640

Ile Gln Arg Gln Thr Val Leu Gln His Ser Phe Asn Gly Pro Gly Pro
                645                 650                 655

Gly Leu Phe Val Val Tyr Arg Asp Ser Ile Pro His Ala Ala Cys His
            660                 665                 670

Lys Gly Pro Gly Pro Gly Ile Arg Thr Leu Glu Asp Leu Leu Met Gly
        675                 680                 685

Thr Leu Gly Ile Val Gly Pro Gly Pro Gly Leu Asp Leu Gln Pro Glu
    690                 695                 700

Thr Thr Asp Leu Tyr Cys Tyr Glu Gln Gly Pro Gly Pro Gly Leu Gln
705                 710                 715                 720

Ala Ile Glu Leu Gln Leu Thr Leu Glu Thr Ile Tyr Asn Gly Pro Gly
                725                 730                 735

Pro Gly Phe Gln Gln Leu Phe Leu Asn Thr Leu Ser Phe Val Cys Pro
            740                 745                 750

Trp Gly Pro Gly Pro Gly Trp Lys His Met Arg Leu Glu Cys Ala Ile
        755                 760                 765

Tyr Tyr Lys Ala Arg Gly Pro Gly Pro Gly Leu Cys Thr Glu Leu Gln
```

```
                    770                 775                 780
Thr Thr Ile His Asp Ile Ile Leu Glu Gly Pro Gly Pro Gly Phe Lys
785                 790                 795                 800

Thr Leu Ile Gln Pro Phe Ile Leu Tyr Ala His Ile Gln Pro Gly
                805                 810                 815

Pro Gly Leu Tyr Trp Tyr Lys Thr Gly Ile Ser Asn Ile Ser Glu Val
                820                 825                 830

Tyr Gly Pro Gly Pro Glu Val Phe Glu Phe Ala Phe Lys Asp Leu
                835                 840                 845

Phe Val Val Tyr Arg Gly Pro Gly Pro Gly His Lys Ala Ile Glu Leu
                850                 855                 860

Gln Met Ala Leu Gln Gly Leu Ala Gln Gly Pro Gly Pro Gly Ala Lys
865                 870                 875                 880

Phe Val Ala Ala Trp Thr Leu Lys Ala Ala Ala
                885                 890

<210> SEQ ID NO 128
<211> LENGTH: 2676
<212> TYPE: DNA
<213> ORGANISM: artificial
<220> FEATURE:
<223> OTHER INFORMATION: Human papillomavirus polyepitope construct

<400> SEQUENCE: 128
atgggcatgc aggtgcagat ccagagcctg ttcctgctgc tgctgtgggt gcccggcagc    60
cggggcaaga gcctgtttgg catgagcctg atgaagaaca gcaccgccgc tgccctctat   120
tggtacaaaa aggccgcctg ctacagcctg tacggcacca ccttcaaggc tgctgccgtg   180
gcctgggaca cgtgtactac catgaagagc accgacctgc gggaccacat cgactacaac   240
atcagcgact accggcacta ctgctacaag gccgcccagg tggtgcccgc ctacaacatc   300
tccaagaacg ctacaacac cttctacatc gagttcaagc tccaggacaa gatcatcgac   360
cactacaaag ccgcctgcct gtacctgcac atccagagtc tgaacgcagc cgctgcaacc   420
ctccaggaca tcgtgctgca cggcaccgtg tacgtgttct gcttcctgct gaacgccatc   480
ctgtacgccc acatccagtg tctgaatgcc gccctgtaca acctgctgat ccggtgcttt   540
aaggccgcct tcgtgtacat cccctgttt ctgatcaaca ccgtgagcgc cacccagctg   600
gtgaagaatg gcaccggctg caacggctgg ttctacaatg ccgccaccaa gtacccctg   660 ctgaagaacg tgtatgtgtt ttgttttctg ctgcccatga acgccacact gcacgacatt   720
atcctggaat gcgtcaaggc cgctgccctg tatggcgtga cttcagcga gctgaagcag   780 gtggactact acggcctgta ctacggcgcc tactacatga ccgacgccgg cacctggaat   840 gccgccccctt acgccgtgtg cgacaagtgc ttcaagcagg cgccatgct ggccgtgttc   900 aagaaagccg ctgccgtggt gctgctgctg gtgcggtata agaatgccgc cgccagctac   960
ttcggcatga gcttcatcca ctttaaagcc gccaagctgc tgtctaagct gctgtgcgtg  1020
aatgccgctg ctgccacaat gtgccggcac tacaagagaa atgccgctgc cagcaccgtg  1080
agcgtgggca ccgccaagaa cgccgccctg agccagatgg tgcagtgggc ctacaagctg  1140
accaacaccg gctgtacaa cgtgaacgcc gctgccacct gcgtgagcca ccggggcctg  1200
tataacgccg ccaagagcgc catcgtgacc ctgacctata aggccgctgc cgacagcgtg  1260
tacgccgaca ccctggaacg gaacatgtac gtgtgctgcc acgtgccct gaatgccgcc  1320 aggttccaca acatccgggg caggttcaaa gccgcctttg tggtgtaccg ggacagcatc  1380
```

```
cccaagaatg ccagcctcca ggatattgag atcacctgtg tgaaggccgt gtacgacttc   1440
gccttccggg acctgtgcat caagtacatg ctggacctcc agcccgagac agtgaacgcc   1500
gccgctggca cactgggcat cgtgtgcccc gtgaacagcg tgatctgctt cgtgaacagc   1560
aaaaacgcca ccctggaaaa gctgacaaat acagggctgt acaatgccgg cctgtattac   1620
gtgcacgagg gcatccggac ctacttcgtg cagggcccag ggccaggctt cctgaacacc   1680
gtggccatcc ccgactccgt gcagatcctg gtcggcccag gaccagggca gcggttccac   1740
aatatcagag gccggtggac cggcagatgc atgggcccag acctggcaca aaataccgga   1800
ctgtataatc tgctgattcg ctgcctgcgg tgccagggtc caggaccagg catcgagttt   1860
atcacctttc tgggcgccct gaagagcttc ctgaaaggac ctggaccagg acccgagtgg   1920
attcagcggc agaccgtgct ccagcacagc ttcaacggac ccggaccggg cctgttcgtg   1980
gtgtacagag actccatccc ccacgccgcc tgtcacaagg acctggacc aggcatcagg   2040 accctggagg acctgctgat gggcacccctg gcattgtgg ggcctggacc tggactggat   2100
ctccagcctg aaaccaccga cctgtactgc tacgagcagg ggccaggacc tgggctccag   2160
gctatcgaac tccagctgac cctggaaacc atctacaatg ccccggacc aggcttccag   2220 cagctgttcc tgaataccct gagcttcgtg tgcccttggg accagggcc cggatggaag   2280 cacatgcggc tggaatgcgc catctactac aaggccagag gccaggacc cggactgtgc   2340 accgaactcc agaccaccat ccacgacatc attctggaag accagggcc aggctttaag   2400 accctgatcc agcccttcat tctgtatgcc cacattcagg acctgggcc tggcctgtat   2460 tggtataaga ccggcatcag caacatctcc gaggtgtacg gcctggacc aggcgaggtg   2520 ttcgagttcg ccttcaagga tctgtttgtg gtgtatagag ccccggacc tggccacaag   2580 gccattgaac tccagatggc cctccagggg ctggcccagg accaggccc tggcgccaag   2640 ttcgtggccg cctggaccct gaaagccgcc gcctga                             2676
```

<210> SEQ ID NO 129
<211> LENGTH: 907
<212> TYPE: PRT
<213> ORGANISM: artificial
<220> FEATURE:
<223> OTHER INFORMATION: Human papillomavirus polyepitope construct

<400> SEQUENCE: 129

```
Met Gly Met Gln Val Gln Ile Gln Ser Leu Phe Leu Leu Leu Leu Trp
1               5                   10                  15

Val Pro Gly Ser Arg Gly Ala Thr Cys Val Ser His Arg Gly Leu Tyr
            20                  25                  30

Asn Ala Ala Ser Thr Asp Leu Arg Asp His Ile Asp Tyr Asn Ala Ala
        35                  40                  45

Ala Ala Thr Met Cys Arg His Tyr Lys Arg Asn Ala Ile Leu Tyr Ala
    50                  55                  60

His Ile Gln Cys Leu Asn Ala Ala Ala Gly Thr Leu Gly Ile Val Cys
65                  70                  75                  80

Pro Val Asn Ala Ala Ala Cys Tyr Ser Leu Tyr Gly Thr Thr Phe Lys
                85                  90                  95

Ala Ala Ala Asp Ser Val Tyr Gly Asp Thr Leu Glu Arg Asn Gln Val
            100                 105                 110

Val Pro Ala Tyr Asn Ile Ser Lys Asn Ala Ala Leu Tyr Asn Leu Leu
        115                 120                 125

Ile Arg Cys Phe Lys Ala Ala Phe Val Tyr Ile Pro Leu Phe Leu Ile
```

-continued

```
            130             135             140
Asn Tyr Tyr Met Thr Asp Ala Gly Thr Trp Gly Ala Val Leu Leu
145             150             155             160

Leu Val Arg Tyr Lys Asn Ala Ala Ile Ser Asp Tyr Arg His Tyr Cys
            165             170             175

Tyr Lys Ala Ala Thr Val Ser Ala Thr Gln Leu Val Lys Lys Ala Ser
            180             185             190

Thr Ala Ala Leu Tyr Trp Tyr Lys Lys Ala Phe Val Val Tyr
            195             200             205

Arg Asp Ser Ile Pro Lys Asn Ala Ser Tyr Phe Gly Met Ser Phe Ile
            210             215             220

His Phe Lys Ala Ala Tyr Met Leu Asp Leu Gln Pro Glu Thr Val Asn
225             230             235             240

Ala Ala Val Tyr Asp Phe Ala Phe Arg Asp Leu Cys Ile Lys Ala Ala
            245             250             255

Leu Gln Asp Lys Ile Ile Asp His Tyr Lys Ala Ala Thr Leu His Asp
            260             265             270

Ile Ile Leu Glu Cys Val Lys Lys Leu Thr Asn Thr Gly Leu Tyr Asn
            275             280             285

Val Gly Ala Ala Ser Val Ile Cys Phe Val Asn Ser Lys Gly Ala
            290             295             300

Ala Ala Met Tyr Val Cys Cys His Val Pro Leu Asn Ala Ser Leu Gln
305             310             315             320

Asp Ile Glu Ile Thr Cys Val Lys Cys Leu Tyr Leu His Ile Gln Ser
            325             330             335

Leu Asn Ala Ala Thr Lys Tyr Pro Leu Leu Lys Asn Val Tyr Val Phe
            340             345             350

Cys Phe Leu Leu Pro Met Asn Ala Lys Gln Gly Ala Met Leu Ala Val
            355             360             365

Phe Lys Lys Ala Ala Leu Ser Gln Met Val Gln Trp Ala Tyr Lys Ala
            370             375             380

Ala Pro Tyr Ala Val Cys Asp Lys Cys Phe Lys Ala Ala Thr Val Tyr
385             390             395             400

Val Phe Cys Phe Leu Leu Asn Ala Ala Ala Thr Leu Gln Asp Ile
            405             410             415

Val Leu His Gly Ala Lys Ser Leu Phe Gly Met Ser Leu Met Lys Asn
            420             425             430

Gly Thr Gly Cys Asn Gly Trp Phe Tyr Asn Ala Arg Phe His Asn Ile
            435             440             445

Arg Gly Arg Phe Lys Ala Ala Lys Leu Leu Ser Lys Leu Leu Cys Val
            450             455             460

Asn Ala Ala Ala Ser Thr Val Ser Val Gly Thr Ala Lys Asn Val Ala
465             470             475             480

Trp Asp Ser Val Tyr Tyr Met Lys Ala Ala Gly Tyr Asn Thr Phe
            485             490             495

Tyr Ile Glu Phe Lys Ala Ala Leu Tyr Gly Val Ser Phe Ser Glu
            500             505             510

Leu Lys Gln Val Asp Tyr Gly Leu Tyr Tyr Asn Ala Ala Lys Ser
            515             520             525

Ala Ile Val Thr Leu Tyr Lys Ala Ala Thr Leu Glu Lys Leu
            530             535             540

Thr Asn Thr Gly Leu Tyr Asn Ala Gly Leu Tyr Tyr Val His Glu Gly
545             550             555             560
```

Ile Arg Thr Tyr Phe Val Gln Gly Pro Gly Pro Phe Leu Asn Thr
            565                 570                 575
Val Ala Ile Pro Asp Ser Val Gln Ile Leu Val Gly Pro Gly Pro Gly
            580                 585                 590
Gln Arg Phe His Asn Ile Arg Gly Arg Trp Thr Gly Arg Cys Met Gly
        595                 600                 605
Pro Gly Pro Gly Thr Asn Thr Gly Leu Tyr Asn Leu Leu Ile Arg Cys
    610                 615                 620
Leu Arg Cys Gln Gly Pro Gly Pro Gly Ile Glu Phe Ile Thr Phe Leu
625                 630                 635                 640
Gly Ala Leu Lys Ser Phe Leu Lys Gly Pro Gly Pro Gly Pro Glu Trp
            645                 650                 655
Ile Gln Arg Gln Thr Val Leu Gln His Ser Phe Asn Gly Pro Gly Pro
        660                 665                 670
Gly Leu Phe Val Val Tyr Arg Asp Ser Ile Pro His Ala Ala Cys His
    675                 680                 685
Lys Gly Pro Gly Pro Gly Ile Arg Thr Leu Glu Asp Leu Leu Met Gly
690                 695                 700
Thr Leu Gly Ile Val Gly Pro Gly Pro Gly Leu Asp Leu Gln Pro Glu
705                 710                 715                 720
Thr Thr Asp Leu Tyr Cys Tyr Glu Gln Gly Pro Gly Pro Gly Leu Gln
                725                 730                 735
Ala Ile Glu Leu Gln Leu Thr Leu Glu Thr Ile Tyr Asn Gly Pro Gly
            740                 745                 750
Pro Gly Phe Gln Gln Leu Phe Leu Asn Thr Leu Ser Phe Val Cys Pro
            755                 760                 765
Trp Gly Pro Gly Pro Gly Trp Lys His Met Arg Leu Glu Cys Ala Ile
        770                 775                 780
Tyr Tyr Lys Ala Arg Gly Pro Gly Pro Gly Leu Cys Thr Glu Leu Gln
785                 790                 795                 800
Thr Thr Ile His Asp Ile Ile Leu Glu Gly Pro Gly Pro Gly Phe Lys
                805                 810                 815
Thr Leu Ile Gln Pro Phe Ile Leu Tyr Ala His Ile Gln Gly Pro Gly
            820                 825                 830
Pro Gly Leu Tyr Trp Tyr Lys Thr Gly Ile Ser Asn Ile Ser Glu Val
            835                 840                 845
Tyr Gly Pro Gly Pro Gly Glu Val Phe Glu Phe Ala Phe Lys Asp Leu
        850                 855                 860
Phe Val Val Tyr Arg Gly Pro Gly Pro Gly His Lys Ala Ile Glu Leu
865                 870                 875                 880
Gln Met Ala Leu Gln Gly Leu Ala Gln Gly Pro Gly Pro Gly Ala Lys
                885                 890                 895
Phe Val Ala Ala Trp Thr Leu Lys Ala Ala Ala
            900                 905

<210> SEQ ID NO 130
<211> LENGTH: 2724
<212> TYPE: DNA
<213> ORGANISM: artificial
<220> FEATURE:
<223> OTHER INFORMATION: Human papillomavirus polyepitope construct

<400> SEQUENCE: 130
atgggcatgc aggtgcagat ccagagcctg ttcctgctgc tgctgtgggt gcccggcagc    60

```
agaggcgcca cctgcgtgag ccacaggggc tctctacaacg ccgccagcac cgacctgcgg      120
gaccacatcg actacaatgc tgctgccgct acaatgtgcc ggcactacaa gcggaacgcc      180
atcctgtacg cccacatcca gtgctgaat gctgccgctg gcacactggg catcgtgtgc       240
cccgtgaatg ccgccgcctg ctacagcctg tacggcacca ccttcaaggc cgctgccgac     300
tccgtgtacg gcgacaccct ggaacggaac caggtggtgc ccgcctacaa catctctaag      360
aatgccgctc tgtacaacct gctgatccgg tgctttaagg ctgccttcgt gtacatcccc      420
ctgtttctga tcaactacta catgaccgac gccggcacat ggggagccgt ggtgctgctg      480
ctggtgcggt acaagaatgc cgccatcagc gactaccggc actactgcta caaggccgcc      540
accgtcagcg ccacccagct ggtgaagaag gccagcacag ccgccgctct ctattggtat      600
aaaaaagccg cctttgtggt gtaccggac agcatcccca gaacgccag ctacttcggc        660 atgagcttca tccacttcaa agccgcctac atgctggacc tccagcccga gaccgtgaac     720
gctgccgtgt acgacttcgc cttccggac ctgtgcatta agccgcact ccaggacaag        780 atcatcgacc attataaagc agccaccctg catgatatta ttctggaatg cgtgaagaag     840
ctgaccaaca ccggcctcta taacgtggga gccgccgcct ctgtgatctg cttcgtgaac     900
agcagggggg ctgccgccat gtatgtgtgc tgccacgtgc ccctgaacgc ctctctccag     960
gatattgaga tcacctgtgt gaagtgcctg tacctgcaca ttcagtctct gaatgccgcc   1020
accaagtacc cctgctgaa gaacgtgtat gtcttttgct tcctgctgcc catgaacgcc    1080
aagcagggcg ccatgctggc cgtgttcaaa aaggccgccc tgagccagat ggtgcagtgg    1140
gcctacaaag ccgcccctta cgccgtgtgc gacaagtgtt ttaaggccgc cacagtgtac    1200
gtgttttgtt ttctgctgaa tgccgctgcc gccaccctcc aggacatcgt gctgcacggc    1260
gccagtcccc tgttcggcat gtccctgatg aagaatggca ccggctgcaa cggctggttc    1320
tacaacgccc ggttccacaa catccgggc aggtttaaag ccgccaagct gctgtctaag     1380
ctgctgtgtg tgaacgccgc cgcttccacc gtgagcgtgg gcaccgccaa gaacgtggcc    1440
tgggacagcg tgtactacat gaaagcagca gccgggtaca acaccttcta catcgagtttt   1500 aaagctgccg ccctgtacgg cgtgagcttc agcgagctga agcaggtgga ctactacggc    1560
ctgtactata cgccgccaa gagcgccatc gtgaccctga cctataaagc cgccgccaca    1620
ctggaaaagc tgaccaatac agggctgtac aatgccggcc tgtattacgt gcacgagggc   1680
atccggacct acttcgtgca gggcccaggg ccaggcttcc tgaacaccgt ggccatcccc    1740
gactccgtgc agatcctggt cggcccagga ccagggcagc ggttccacaa tatcagaggc    1800
cggtggaccg gcagatgcat gggcccagga cctggcacaa ataccggact gtataatctg    1860
ctgattcgct gcctgcggtg ccagggtcca ggaccaggca tcgagtttat cacctttctg    1920
ggcgccctga agagcttcct gaaaggacct ggaccaggac ccgagtggat tcagcggcag   1980
accgtgctcc agcacagctt caacggaccc ggacccggcc tgttcgtggt gtacagagac    2040
tccatccccc acgccgcctg tcacaaggga cctggaccag gcatcaggac cctggaggac    2100
ctgctgatgg gcaccctggg cattgtgggg cctggacctg gactggatct ccagcctgaa    2160
accaccgacc tgtactgcta cgagcagggg ccaggacctg gctccaggc tatcgaactc    2220 cagctgaccc tggaaaccat ctacaatggc cccggaccag gcttccagca gctgttcctg    2280 aatacccctga gctccgtgtg cccttgggga ccagggccg gatggaagca catgcggctg    2340
gaatgcgcca tctactacaa ggccagaggc ccaggacccg gactgtgcac cgaactccag    2400
accaccatcc acgacatcat tctggaagga ccagggccag gctttaagac cctgatccag    2460
```

```
ccccttcattc tgtatgccca cattcaggga cctgggcctg gcctgtattg gtataagacc    2520
ggcatcagca acatctccga ggtgtacggg cctggaccag gcgaggtgtt cgagttcgcc    2580
ttcaaggatc tgtttgtggt gtatagaggc cccggacctg ccacaaggc cattgaactc     2640 cagatggccc tccagggggct ggcccaggga ccaggccctg cgccaagtt cgtggccgcc    2700 tggaccctga aagccgccgc ctga                                           2724
```

<210> SEQ ID NO 131
<211> LENGTH: 22
<212> TYPE: PRT
<213> ORGANISM: Artificial
<220> FEATURE:
<223> OTHER INFORMATION: Mouse Igkappa signal sequence

<400> SEQUENCE: 131

Met Gly Met Gln Val Gln Ile Gln Ser Leu Phe Leu Leu Leu Leu Trp
1               5                   10                  15

Val Pro Gly Ser Arg Gly
            20

<210> SEQ ID NO 132
<211> LENGTH: 9
<212> TYPE: PRT
<213> ORGANISM: Human papillomavirus type 16

<400> SEQUENCE: 132

Ile Ser Glu Tyr Arg His Tyr Cys Tyr
1               5

<210> SEQ ID NO 133
<211> LENGTH: 10
<212> TYPE: PRT
<213> ORGANISM: Human papillomavirus type 16

<400> SEQUENCE: 133

Tyr Met Leu Asp Leu Gln Pro Glu Thr Thr
1               5                   10

<210> SEQ ID NO 134
<211> LENGTH: 9
<212> TYPE: PRT
<213> ORGANISM: Human papillomavirus type 16

<400> SEQUENCE: 134

Gly Thr Leu Gly Ile Val Cys Pro Ile
1               5

<210> SEQ ID NO 135
<211> LENGTH: 10
<212> TYPE: PRT
<213> ORGANISM: Human papillomavirus type 16

<400> SEQUENCE: 135

Thr Ile His Asp Ile Ile Leu Glu Cys Val
1               5                   10

<210> SEQ ID NO 136
<211> LENGTH: 10
<212> TYPE: PRT
<213> ORGANISM: Human papillomavirus type 18

<400> SEQUENCE: 136

```
Lys Leu Thr Asn Thr Gly Leu Tyr Asn Leu
 1               5                  10

<210> SEQ ID NO 137
<211> LENGTH: 10
<212> TYPE: PRT
<213> ORGANISM: Human papillomavirus type 18

<400> SEQUENCE: 137

Asp Ser Val Tyr Gly Asp Thr Leu Glu Lys
 1               5                  10

<210> SEQ ID NO 138
<211> LENGTH: 10
<212> TYPE: PRT
<213> ORGANISM: Human papillomavirus type 18

<400> SEQUENCE: 138

Phe Val Val Tyr Arg Asp Ser Ile Pro His
 1               5                  10

<210> SEQ ID NO 139
<211> LENGTH: 9
<212> TYPE: PRT
<213> ORGANISM: Human papillomavirus type 16

<400> SEQUENCE: 139

Cys Tyr Ser Leu Tyr Gly Thr Thr Leu
 1               5

<210> SEQ ID NO 140
<211> LENGTH: 9
<212> TYPE: PRT
<213> ORGANISM: Human papillomavirus type 16

<400> SEQUENCE: 140

Pro Tyr Ala Val Cys Asp Lys Cys Leu
 1               5

<210> SEQ ID NO 141
<211> LENGTH: 9
<212> TYPE: PRT
<213> ORGANISM: Human papillomavirus type 16

<400> SEQUENCE: 141

Arg Phe His Asn Ile Arg Gly Arg Trp
 1               5

<210> SEQ ID NO 142
<211> LENGTH: 9
<212> TYPE: PRT
<213> ORGANISM: Human papillomavirus type 18

<400> SEQUENCE: 142

Leu Tyr Asn Leu Leu Ile Arg Cys Leu
 1               5

<210> SEQ ID NO 143
<211> LENGTH: 9
<212> TYPE: PRT
<213> ORGANISM: Artificial
<220> FEATURE:
<223> OTHER INFORMATION: Human papillomavirus type 18-derived epitope

<400> SEQUENCE: 143
```

```
Leu Tyr Asn Leu Leu Ile Arg Trp Leu
1               5

<210> SEQ ID NO 144
<211> LENGTH: 9
<212> TYPE: PRT
<213> ORGANISM: Artificial
<220> FEATURE:
<223> OTHER INFORMATION: Human papillomavirus type 16-derived epitope

<400> SEQUENCE: 144

Leu Tyr Gly Val Ser Phe Thr Glu Leu
1               5

<210> SEQ ID NO 145
<211> LENGTH: 9
<212> TYPE: PRT
<213> ORGANISM: Artificial
<220> FEATURE:
<223> OTHER INFORMATION: Human papillomavirus type 16-derived epitope

<400> SEQUENCE: 145

Cys Tyr Ser Val Tyr Gly Thr Thr Leu
1               5

<210> SEQ ID NO 146
<211> LENGTH: 9
<212> TYPE: PRT
<213> ORGANISM: Human papillomavirus type 31

<400> SEQUENCE: 146

Gln Ala Glu Pro Asp Thr Ser Asn Tyr
1               5

<210> SEQ ID NO 147
<211> LENGTH: 10
<212> TYPE: PRT
<213> ORGANISM: Human papillomavirus type 45

<400> SEQUENCE: 147

Leu Gln Asp Val Ser Ile Ala Cys Val Tyr
1               5                   10

<210> SEQ ID NO 148
<211> LENGTH: 9
<212> TYPE: PRT
<213> ORGANISM: Human papillomavirus type 31

<400> SEQUENCE: 148

Phe Ala Phe Thr Asp Leu Thr Ile Val
1               5

<210> SEQ ID NO 149
<211> LENGTH: 10
<212> TYPE: PRT
<213> ORGANISM: Human papillomavirus type 45

<400> SEQUENCE: 149

Tyr Gln Phe Ala Phe Lys Asp Leu Cys Ile
1               5                   10

<210> SEQ ID NO 150
<211> LENGTH: 9
<212> TYPE: PRT
<213> ORGANISM: Human papillomavirus type 45
```

```
<400> SEQUENCE: 150

Thr Leu Gln Glu Ile Val Leu His Leu
1               5

<210> SEQ ID NO 151
<211> LENGTH: 10
<212> TYPE: PRT
<213> ORGANISM: Human papillomavirus type 45

<400> SEQUENCE: 151

Arg Thr Glu Val Tyr Gln Phe Ala Phe Lys
1               5                   10

<210> SEQ ID NO 152
<211> LENGTH: 9
<212> TYPE: PRT
<213> ORGANISM: Human papillomavirus type 31

<400> SEQUENCE: 152

Ser Val Tyr Gly Thr Thr Leu Glu Lys
1               5

<210> SEQ ID NO 153
<211> LENGTH: 9
<212> TYPE: PRT
<213> ORGANISM: Human papilloma virus

<400> SEQUENCE: 153

His Tyr Thr Asn Trp Lys Phe Ile Tyr
1               5

<210> SEQ ID NO 154
<211> LENGTH: 10
<212> TYPE: PRT
<213> ORGANISM: Human papilloma virus

<400> SEQUENCE: 154

Phe Tyr Ser Arg Ile Arg Glu Leu Arg Tyr
1               5                   10

<210> SEQ ID NO 155
<211> LENGTH: 5
<212> TYPE: PRT
<213> ORGANISM: Artificial
<220> FEATURE:
<223> OTHER INFORMATION: Synthetic linker

<400> SEQUENCE: 155

Gly Pro Gly Pro Gly
1               5

<210> SEQ ID NO 156
<211> LENGTH: 872
<212> TYPE: PRT
<213> ORGANISM: Artificial
<220> FEATURE:
<223> OTHER INFORMATION: Human papillomavirus polyepitope construct

<400> SEQUENCE: 156

Ala Phe Thr Asp Leu Thr Ile Val Tyr Asn Ser Thr Trp His Trp Thr
1               5                   10                  15

Gly Cys Asn Lys Lys Ala Ala Ala Lys Leu Leu Glu Lys Leu Leu Cys
            20                  25                  30

Ile Asn Ala Tyr Gln Phe Ala Phe Lys Asp Leu Cys Val Lys Met Val
```

```
            35                  40                  45
Met Leu Met Leu Val Arg Phe Lys Asn Ala Ala Leu Gln Asp Lys Ile
 50                  55                  60
Leu Asp His Tyr Lys Ala Ala Phe Leu Leu Cys Phe Cys Val Leu Leu
 65                  70                  75                  80
Asn Ser Val Tyr Gly Thr Thr Leu Glu Arg Asn Ala Ala Val Thr Thr
                     85                  90                  95
Arg Tyr Pro Leu Leu Arg Asn Ala Thr Leu Gln Glu Ile Val Leu His
                100                 105                 110
Val Asn Tyr Tyr Ile Thr Glu Thr Gly Ile Trp Lys Val Val Phe Ile
                115                 120                 125
Tyr Ile Pro Leu Phe Asn Gln Thr Glu Pro Asp Thr Ser Asn Tyr Gly
                130                 135                 140
Ala Ala Glu Leu Asp Pro Val Asp Leu Leu Cys Tyr Lys Ala Ala Ala
145                 150                 155                 160
Leu Thr Asp Val Ser Ile Ala Cys Val Tyr Asn Ala Ala Arg Thr Glu
                165                 170                 175
Val Tyr Gln Phe Ala Phe Arg Asn Pro Tyr Leu His Ser Arg Leu Val
                180                 185                 190
Val Phe Asn Ile Ser Phe Ala Gly Ile Val Thr Lys Lys Val Met Asp
                195                 200                 205
Asp Ser Glu Ile Ala Tyr Asn Ala Phe Tyr Ser Arg Ile Arg Glu Leu
210                 215                 220
Arg Phe Lys Ala Ala Ala Phe Ile Tyr Ile Pro Leu Phe Val Ile Lys
225                 230                 235                 240
Ala Val Phe Thr Phe Pro His Ala Phe Pro Phe Asn Ala Phe Tyr Ser
                245                 250                 255
Lys Val Ser Glu Phe Arg Trp Lys Ser Leu Val Phe Leu Leu Cys Phe
                260                 265                 270
Ser Val Asn Ala Ser Thr Ala Ala Ala Leu Tyr Trp Tyr Arg Lys Ala
                275                 280                 285
Thr Leu Tyr Ala His Ile Gln Cys Leu Asn Ala Ala His Tyr Thr Asn
                290                 295                 300
Trp Lys Phe Ile Phe Asn Ala Ala Asn Thr Glu Leu Tyr Asn Leu Leu
305                 310                 315                 320
Ile Asn Ala Ser Tyr Phe Gly Met Ser Phe Ile His Phe Lys Leu Thr
                325                 330                 335
Asn Lys Gly Ile Cys Asp Leu Asn Ser Val Tyr Gly Glu Thr Leu Glu
                340                 345                 350
Lys Asn Val Tyr Val Cys Ala Phe Ala Trp Leu Leu Asn Val Tyr Gly
                355                 360                 365
Thr Thr Leu Glu Lys Leu Lys Leu Ser Gln Met Val Gln Trp Ala Tyr
                370                 375                 380
Lys Ala Ala Ala Tyr Val Val Trp Asp Ser Ile Tyr Tyr Ile Asn Gly
385                 390                 395                 400
Thr Gly Cys Asn Gly Trp Phe Tyr Gly Ala Ala Ala Val Met Cys Arg
                405                 410                 415
His Tyr Lys Arg Asn Phe Leu Leu Cys Phe Ser Val Cys Leu Asn Ala
                420                 425                 430
Val Tyr Gln Phe Ala Phe Lys Asp Leu Lys Ala Ala Lys Val Ser Glu
                435                 440                 445
Phe Arg Trp Tyr Arg Tyr Lys Tyr Thr Asn Trp Lys Phe Ile Tyr Leu
450                 455                 460
```

```
Asn Ala Ala Leu Ser Ser Ala Leu Glu Ile Pro Tyr Lys Ala Ala Phe
465                 470                 475                 480

Leu Phe Thr Asp Leu Thr Ile Val Asn Ala Ala Thr Thr Pro Ile Ile
            485                 490                 495

His Leu Lys Asn Ala Ala Arg Gln Met Asn Met Ser Gln Trp Ile
        500                 505                 510

Lys Asn Thr Gly Ile Leu Thr Val Thr Tyr Asn Val Phe Thr Phe Pro
        515                 520                 525

Asn Pro Phe Pro Phe Lys Ala Ala Glu Ile Val Leu His Leu Glu
        530                 535                 540

Pro Gln Asn Glu Leu Asp Pro Val Gly Pro Gly Pro Gly Ile Arg Ile
545                 550                 555                 560

Leu Gln Glu Leu Leu Met Gly Ser Phe Gly Ile Val Gly Pro Gly Pro
                565                 570                 575

Gly Thr Gly Arg Cys Ile Ala Cys Trp Arg Arg Pro Arg Thr Glu Thr
            580                 585                 590

Gly Pro Gly Pro Gly Trp Lys His Ile Arg Leu Glu Cys Val Leu Met
        595                 600                 605

Tyr Lys Ala Arg Gly Pro Gly Pro Gly Leu Cys Ile Val Tyr Arg Asp
        610                 615                 620

Cys Ile Ala Tyr Ala Ala Cys His Gly Pro Gly Pro Gly Pro Glu Trp
625                 630                 635                 640

Ile Glu Arg Gln Thr Val Leu Gln His Ser Phe Asn Gly Pro Gly Pro
                645                 650                 655

Gly Pro Ile Asn Ile Ser Lys Ser Lys Ala His Lys Ala Ile Glu Leu
            660                 665                 670

Gly Pro Gly Pro Gly Leu Arg Thr Leu Gln Gln Leu Phe Leu Ser Thr
        675                 680                 685

Leu Ser Phe Val Gly Pro Gly Pro Gly Phe His Ser Ile Ala Gly Gln
        690                 695                 700

Tyr Arg Gly Gln Cys Asn Thr Cys Gly Pro Gly Pro Gly Thr Thr Pro
705                 710                 715                 720

Ile Ile His Leu Lys Gly Asp Ala Asn Ile Leu Lys Gly Pro Gly Pro
                725                 730                 735

Gly Asp Trp Val Met Ala Ile Phe Gly Val Asn Pro Thr Val Ala Glu
            740                 745                 750

Gly Phe Gly Pro Gly Pro Gly Pro Arg Lys Leu His Glu Leu Ser Ser
        755                 760                 765

Ala Leu Glu Ile Pro Tyr Gly Pro Gly Pro Gly Phe Lys Thr Leu Ile
        770                 775                 780

Lys Pro Ala Thr Leu Tyr Ala His Ile Gln Gly Pro Gly Pro Gly Thr
785                 790                 795                 800

Ile Pro Asn Ser Val Gln Ile Ser Val Gly Tyr Met Thr Ile Gly Pro
                805                 810                 815

Gly Pro Gly Asn Gly Trp Phe Tyr Val Glu Ala Val Ile Asp Arg Gln
            820                 825                 830

Thr Gly Gly Pro Gly Pro Gly Val Leu Asp Phe Ala Phe Thr Asp Leu
        835                 840                 845

Thr Ile Val Tyr Arg Asp Gly Pro Gly Pro Gly Ala Lys Phe Val Ala
        850                 855                 860

Ala Trp Thr Leu Lys Ala Ala Ala
865                 870
```

<210> SEQ ID NO 157
<211> LENGTH: 2616
<212> TYPE: DNA
<213> ORGANISM: artificial
<220> FEATURE:
<223> OTHER INFORMATION: Human papillomavirus polyepitope construct

<400> SEQUENCE: 157

| | | | | | |
|---|---|---|---|---|---|
| gctttcaccg | acctgaccat | cgtgtacaac | agcacctggc | actggaccgg ctgcaacaag | 60 |
| aaagccgctg | ccaagctgct | ggaaaagctg | ctgtgcatca | acgcctatca gtttgccttc | 120 |
| aaggacctgt | gcgtgaagat | ggtgatgctg | atgctggtgc | ggttcaagaa tgccgctctc | 180 |
| caggacaaga | tcctggacca | ctacaaggcc | gcctttctgc | tgtgcttctg cgtgctgctg | 240 |
| aacagcgtgt | acggcaccac | cctggaacgg | aacgccgccg | tgaccaccag ataccccctg | 300 |
| ctgcggaatg | ccaccctcca | ggaaatcgtc | ctgcacgtca | attactacat caccgagacc | 360 |
| ggcatctgga | aggtggtgtt | catctacatc | ccctgttca | accagaccga gcccgacacc | 420 |
| agcaactacg | agccgccga | actcgatccc | gtggacctgc | tgtgctacaa gccgctgcc | 480 |
| ctgaccgacg | tgagcatcgc | ctgcgtgtac | aacgccgcca | ggaccgaggt gtaccagttt | 540 |
| gcctttcgga | ccctacct | gcacagcaga | ctggtggtgt | taacatcag cttcgccggc | 600 |
| atcgtgacca | agaaagtgat | ggacgacagc | gagatcgcct | acaacgcctt ctacagccgg | 660 |
| atcagagagc | tgaggttcaa | agccgctgcc | tttatctaca | ttcctctgtt cgtgatcaag | 720 |
| gccgtgttca | ccttcccca | cgccttccct | tcaatgcct | tctactccaa ggtgtccgag | 780 |
| ttccggtgga | agagcctggt | gttcctgctg | tgtttcagcg | tgaacgccag caccgccgct | 840 |
| gccctgtact | ggtacaggaa | ggccaccctg | tacgcccata | tccagtgcct gaatgccgcc | 900 |
| cactacacca | actggaagtt | catcttcaat | gccgccaaca | ccgagctgta caacctgctg | 960 |
| atcaacgcca | gctacttcgg | catgagcttc | atccacttca | agctgaccaa caagggcatc | 1020 |
| tgcgacctga | actccgtgta | cggcgagaca | ctggaaaaga | acgtgtacgt gtgcgccttc | 1080 |
| gcctggctgc | tgaacgtgta | tggcacaaca | ctggaaaaac | tgaagctgtc ccagatggtg | 1140 |
| cagtgggcct | ataaagccgc | cgcctacgtg | gtgtgggaca | gcatctacta tatcaacggc | 1200 |
| accggctgta | acggctggtt | ttacggcgcc | gctgccgtga | tgtgccggca ctacaagcgg | 1260 |
| aattttctgc | tgtgttttc | cgtgtgcctg | aacgccgtgt | atcagttcgc ctttaaggat | 1320 |
| ctgaaggctg | ccaaagtgtc | tgagttcaga | tggtacaggt | acaagtacac aaattggaag | 1380 |
| tttatctatc | tgaacgccgc | cctgagcagc | ccctgaaa | tccctataa ggctgccttc | 1440 |
| ctgttcaccg | atctgactat | tgtgaacgcc | gccaccaccc | ccatcatcca cctgaaaaac | 1500 |
| gccgctgcca | ggcagatgaa | catgagccag | tggatcaaga | acaccggcat cctgaccgtg | 1560 |
| acctacaacg | tgtttaccct | tcccaaccct | ttcccctta | agccgctgc cgagatcgtg | 1620 |
| ctgcacctgg | aacccagaa | cgagctggac | cctgtgggcc | ctggcctgg catcagaatc | 1680 |
| ctccaggaac | tgctgatggg | cagcttcggc | atcgtgggc | caggccccgg aaccggccgg | 1740 |
| tgcatcgcct | gttggcggag | gcccggacc | gagacaggcc | ctggaccgg ctggaagcac | 1800 |
| atccggctgg | aatgcgtgct | gatgtacaag | gccaggggac | ccggccctgg cctctgtatc | 1860 |
| gtgtaccgcg | actgcatcgc | ctacgccgcc | tgccacggcc | aggacctgg ccccgagtgg | 1920 |
| atcgagcggc | agaccgtgct | ccagcatagc | ttcaacggac | ccggaccagg ccccatcaac | 1980 |
| atcagcaaga | gcaaggccca | aaggccatc | gagctgggcc | ctgggcccgg actgcggacc | 2040 |
| ctccagcagc | tgttcctgag | caccctgagc | ttcgtgggac | ctgggccagg cttccacagc | 2100 |

```
atcgccggcc agtaccgggg ccagtgcaac acctgcggcc cagggccagg caccacacct    2160
attattcacc tgaagggcga cgccaacatc ctgaaggggc caggacccgg cgactgggtg    2220
atggccatct tcggcgtgaa ccccaccgtg gccgagggct tcggacctgg acctgggcct    2280
aggaagctgc acgagctgtc ctctgccctg gaaattcctt acggccctgg cccaggcttc    2340
aagaccctga tcaagcccgc cacactgtat gcccacattc agggccctgg accaggcacc    2400
atccccaaca gcgtgcagat cagcgtgggc tacatgacca tcggaccagg cctggcaat    2460 ggctggttct acgtggaggc cgtgatcgac aggcagaccg gcggacctgg cccaggggtg    2520
ctggacttcg cctttacaga cctgacaatt gtgtaccggg acggccctgg gcctggcgcc    2580
aagttcgtgg ccgcctggac cctgaaggcc gctgcc                              2616
```

<210> SEQ ID NO 158
<211> LENGTH: 872
<212> TYPE: PRT
<213> ORGANISM: artificial
<220> FEATURE:
<223> OTHER INFORMATION: Human papillomavirus polyepitope construct

<400> SEQUENCE: 158

```
Phe Tyr Ser Lys Val Ser Glu Phe Arg Trp Lys Ala Ala Arg Thr Glu
1               5                   10                  15

Val Tyr Gln Phe Ala Phe Arg Asn Ala Ala Val Thr Thr Arg Tyr Pro
            20                  25                  30

Leu Leu Arg Asn Val Phe Thr Phe Pro Asn Pro Phe Pro Phe Asn Tyr
        35                  40                  45

Thr Asn Trp Lys Phe Ile Tyr Leu Asn Ala Ser Val Tyr Gly Glu Thr
    50                  55                  60

Leu Glu Lys Gly Ala Ala Val Met Cys Arg His Tyr Lys Arg Asn Ala
65                  70                  75                  80

Val Tyr Gly Thr Thr Leu Glu Lys Leu Lys Val Val Phe Ile Tyr Ile
                85                  90                  95

Pro Leu Phe Gly Ala Ala Lys Leu Leu Glu Lys Leu Leu Cys Ile Asn
            100                 105                 110

Gly Thr Gly Cys Asn Gly Trp Phe Tyr Asn Gln Thr Glu Pro Asp Thr
        115                 120                 125

Ser Asn Tyr Asn Ala Ala Pro Tyr Leu His Ser Arg Leu Val Val
    130                 135                 140

Phe Gly Ala Ala Ala Leu Thr Asp Val Ser Ile Ala Cys Val Tyr Asn
145                 150                 155                 160

Ala His Tyr Thr Asn Trp Lys Phe Ile Phe Gly Ala Ala Phe Ile Tyr
                165                 170                 175

Ile Pro Leu Phe Val Ile Lys Ala Ala Ala Met Val Met Leu Met Leu
            180                 185                 190

Val Arg Phe Lys Asn Ala Ala Asn Thr Glu Leu Tyr Asn Leu Leu Ile
        195                 200                 205

Asn Phe Leu Phe Thr Asp Leu Thr Ile Val Asn Phe Leu Leu Cys Phe
    210                 215                 220

Cys Val Leu Leu Asn Ala Ala Thr Thr Pro Ile Ile His Leu Lys Gly
225                 230                 235                 240

Ala Ala Lys Leu Thr Asn Lys Gly Ile Cys Asp Leu Asn Ala Leu Gln
                245                 250                 255

Asp Lys Ile Leu Asp His Tyr Lys Asn Thr Gly Ile Leu Thr Val Thr
            260                 265                 270
```

```
Tyr Gly Ala Ala Ala Val Met Asp Asp Ser Glu Ile Ala Tyr Asn Ser
        275                 280                 285

Thr Trp His Trp Thr Gly Cys Asn Lys Lys Ala Ala Ser Tyr Phe Gly
290                 295                 300

Met Ser Phe Ile His Phe Lys Leu Ser Ser Ala Leu Glu Ile Pro Tyr
305                 310                 315                 320

Lys Leu Ser Gln Met Val Gln Trp Ala Tyr Asn Ser Leu Val Phe Leu
            325                 330                 335

Leu Cys Phe Ser Val Asn Ala Thr Leu Tyr Ala His Ile Gln Cys Leu
            340                 345                 350

Asn Val Phe Thr Phe Pro His Ala Phe Pro Phe Asn Ala Ala Ala Arg
            355                 360                 365

Gln Met Asn Met Ser Gln Trp Ile Lys Asn Ala Thr Leu Gln Glu Ile
        370                 375                 380

Val Leu His Val Asn Ala Ala Phe Thr Asp Leu Thr Ile Val Tyr Asn
385                 390                 395                 400

Ile Ser Phe Ala Gly Ile Val Thr Lys Lys Tyr Val Val Trp Asp Ser
                405                 410                 415

Ile Tyr Tyr Ile Asn Tyr Tyr Ile Thr Glu Thr Gly Ile Trp Lys Ala
            420                 425                 430

Ala Ala Phe Tyr Ser Arg Ile Arg Glu Leu Arg Phe Lys Val Tyr Gln
            435                 440                 445

Phe Ala Phe Lys Asp Leu Lys Ala Phe Leu Leu Cys Phe Ser Val Cys
        450                 455                 460

Leu Asn Ala Ala Tyr Gln Phe Ala Phe Lys Asp Leu Cys Val Lys Ser
465                 470                 475                 480

Val Tyr Gly Thr Thr Leu Glu Arg Asn Lys Val Ser Glu Phe Arg Trp
                485                 490                 495

Tyr Arg Tyr Lys Ala Ala Glu Leu Asp Pro Val Asp Leu Leu Cys Tyr
            500                 505                 510

Lys Ser Thr Ala Ala Ala Leu Tyr Trp Tyr Arg Lys Ala Ala Ala Val
            515                 520                 525

Tyr Val Cys Ala Phe Ala Trp Leu Leu Glu Ile Val Leu His Leu Glu
            530                 535                 540

Pro Gln Asn Glu Leu Asp Pro Val Gly Pro Gly Pro Gly Ile Arg Ile
545                 550                 555                 560

Leu Gln Glu Leu Leu Met Gly Ser Phe Gly Ile Val Gly Pro Gly Pro
                565                 570                 575

Gly Thr Gly Arg Cys Ile Ala Cys Trp Arg Arg Pro Arg Thr Glu Thr
            580                 585                 590

Gly Pro Gly Pro Gly Trp Lys His Ile Arg Leu Glu Cys Val Leu Met
            595                 600                 605

Tyr Lys Ala Arg Gly Pro Gly Pro Gly Leu Cys Ile Val Tyr Arg Asp
610                 615                 620

Cys Ile Ala Tyr Ala Ala Cys His Gly Pro Gly Pro Gly Pro Glu Trp
625                 630                 635                 640

Ile Glu Arg Gln Thr Val Leu Gln His Ser Phe Asn Gly Pro Gly Pro
                645                 650                 655

Gly Pro Ile Asn Ile Ser Lys Ser Lys Ala His Lys Ala Ile Glu Leu
            660                 665                 670

Gly Pro Gly Pro Gly Leu Arg Thr Leu Gln Gln Leu Phe Leu Ser Thr
            675                 680                 685
```

Leu Ser Phe Val Gly Pro Gly Pro Gly Phe His Ser Ile Ala Gly Gln
    690             695             700

Tyr Arg Gly Gln Cys Asn Thr Cys Gly Pro Gly Thr Thr Pro
705             710             715             720

Ile Ile His Leu Lys Gly Asp Ala Asn Ile Leu Lys Gly Pro Gly Pro
            725             730             735

Gly Asp Trp Val Met Ala Ile Phe Gly Val Asn Pro Thr Val Ala Glu
            740             745             750

Gly Phe Gly Pro Gly Pro Gly Pro Arg Lys Leu His Glu Leu Ser Ser
            755             760             765

Ala Leu Glu Ile Pro Tyr Gly Pro Gly Pro Gly Phe Lys Thr Leu Ile
770             775             780

Lys Pro Ala Thr Leu Tyr Ala His Ile Gln Gly Pro Gly Pro Gly Thr
785             790             795             800

Ile Pro Asn Ser Val Gln Ile Ser Val Gly Tyr Met Thr Ile Gly Pro
            805             810             815

Gly Pro Gly Asn Gly Trp Phe Tyr Val Glu Ala Val Ile Asp Arg Gln
            820             825             830

Thr Gly Gly Pro Gly Pro Gly Val Leu Asp Phe Ala Phe Thr Asp Leu
            835             840             845

Thr Ile Val Tyr Arg Asp Gly Pro Gly Pro Gly Ala Lys Phe Val Ala
850             855             860

Ala Trp Thr Leu Lys Ala Ala Ala
865             870

<210> SEQ ID NO 159
<211> LENGTH: 2616
<212> TYPE: DNA
<213> ORGANISM: artificial
<220> FEATURE:
<223> OTHER INFORMATION: Human papillomavirus polyepitope construct

<400> SEQUENCE: 159
ttctacagca aggtgtccga gttccggtgg aaggccgcca ggaccgaggt gtaccagttc     60
gccttccgga cgccgccgt gaccaccaga taccccctgc tgcggaacgt gttcaccttc    120
cccaacccct tccctttcaa ctacaccaac tggaagttca tctacctgaa cgccagcgtg    180
tacggcgaga ccctggaaaa gggagcagcc gtgatgtgcc ggcactacaa gcggaacgcc    240
gtgtacggca ccacactgga aaagctgaag gtggtgttca tctacatccc cctgttcgga    300
gccgccaagc tgctggaaaa actgctgtgc atcaacggca ccggctgcaa cggctggttc    360
tacaaccaga ccgagcccga caccagcaac tacaatgctg ccgcccccta cctgcacagc    420
agactggtgg tgtttggggc tgccgccctg accgacgtga gcatcgcctg cgtgtacaac    480
gcccactaca caaattggaa attcattttt ggagccgcct tcatctatat tcctctgttc    540
gtgatcaaag ccgccgctat ggtgatgctg atgctggtgc ggttcaagaa cgccgccaac    600
accgagctgt acaacctgct gatcaacttc ctgttcaccg acctgaccat cgtgaacttt    660
ctcctgtgtt tctgcgtgct cctgaatgcc gccacaaccc ccatcatcca cctgaaggga    720
gccgccaaac tgaccaacaa gggcatctgc gacctgaatg ccctccagga caagatcctg    780
gaccactaca gaacaccgg catcctgacc gtgacctatg agccgctgc cgtgatggac    840 gacagcgaga tcgcctacaa cagcacctgg cactggaccg gctgtaacaa gaaggccgcc    900
tcctacttcg gcatgagctt catccacttc aagctgtcca cgccctgga aatcccctac    960 aagctgtccc agatggtgca gtgggcctac aactccctgg tgttcctgct gtgtttcagc   1020

```
gtgaacgcaa ccctctatgc ccacatccag tgcctgaatg tgtttacctt ccctcacgcc      1080
tttcccttca atgccgccgc cagacagatg aacatgagcc agtggatcaa gaatgccacc      1140
ctccaggaga ttgtcctgca cgtcaatgcc gcctttactg atctgactat cgtgtacaac      1200
atcagcttcg ccggcatcgt gaccaagaaa tacgtggtgt gggacagcat ctactacatc      1260
aattactaca tcaccgagac cggcatctgg aaagctgccg ccttctacag ccggatcagg      1320
gagctgaggt tcaaagtgta tcagtttgct ttcaaagacc tgaaagcctt cctgctgtgc      1380
ttttccgtgt gcctgaacgc cgcctaccag tttgccttta aggatctgtg cgtgaagagc      1440
gtgtatggca caaccctgga acggaacaaa gtgtctgagt ccgctggta caggtataag      1500 gccgccgaac tcgatcccgt ggatctgctg tgttacaaga gcactgccgc cgcactgtac      1560
tggtatagga aggctgccgc cgtgtacgtg tgcgccttcg cctggctgct ggagatcgtg      1620
ctgcacctgg aaccccagaa cgagctggac cctgtgggcc ctggccctgg catcagaatc      1680
ctccaggaac tgctgatggg cagcttcggc atcgtgggcc caggcccgg aaccggccgg      1740 tgcatcgcct gttggcggag gccccggacc gagacaggcc ctggacccgg ctggaagcac      1800
atccggctgg aatgcgtgct gatgtacaag gccaggggac ccggccctgg cctctgtatc      1860
gtgtaccgcg actgcatcgc ctacgccgcc tgccacggcc aggacctggg cccgagtgg      1920 atcgagcggc agaccgtgct ccagcatagc ttcaacggac ccggaccagg ccccatcaac      1980
atcagcaaga gcaaggccca aaggccatc gagctgggcc ctgggccgg actgcggacc      2040 ctccagcagc tgttcctgag cacccctgagc ttcgtgggac ctgggccagg cttccacagc      2100
atcgccggcc agtaccgggg ccagtgcaac acctgcggcc agggccagg caccacacct      2160 attattcacc tgaagggcga cgccaacatc ctgaaggggc caggaccccgg cgactgggtg      2220 atggccatct tcggcgtgaa ccccaccgtg gccgagggct cggacctgg acctgggcct      2280 aggaagctgc acgagctgtc ctctgccctg gaaattcctt acggccctgg cccaggcttc      2340
aagaccctga tcaagcccgc cacactgtat gcccacattc agggccctgg accaggcacc      2400
atccccaaca gcgtgcagat cagcgtgggc tacatgacca tcggaccagg gcctggcaat      2460
ggctggttct acgtggaggc cgtgatcgac aggcagaccg gcgacctgg cccaggggtg      2520 ctggacttcg cctttacaga cctgacaatt gtgtaccggg acggccctgg gcctggcgcc      2580
aagttcgtgg ccgcctggac cctgaaggcc gctgcc                               2616
```

<210> SEQ ID NO 160
<211> LENGTH: 869
<212> TYPE: PRT
<213> ORGANISM: artificial
<220> FEATURE:
<223> OTHER INFORMATION: Human papillomavirus polyepitope construct

<400> SEQUENCE: 160

```
Lys Ser Leu Phe Gly Met Ser Leu Met Lys Asn Ser Thr Ala Ala Ala
1               5                   10                  15

Leu Tyr Trp Tyr Lys Lys Ala Ala Cys Tyr Ser Leu Tyr Gly Thr Thr
            20                  25                  30

Phe Lys Ala Ala Ala Val Ala Trp Asp Ser Val Tyr Tyr Met Lys Ser
        35                  40                  45

Thr Asp Leu Arg Asp His Ile Asp Tyr Asn Ile Ser Asp Tyr Arg His
    50                  55                  60

Tyr Cys Tyr Lys Ala Ala Gln Val Val Pro Ala Tyr Asn Ile Ser Lys
65                  70                  75                  80
```

```
Asn Gly Tyr Asn Thr Phe Tyr Ile Glu Phe Lys Leu Gln Asp Lys Ile
                85                  90                  95
Ile Asp His Tyr Lys Ala Ala Cys Leu Tyr Leu His Ile Gln Ser Leu
            100                 105                 110
Asn Ala Ala Ala Ala Thr Leu Gln Asp Ile Val Leu His Gly Thr Val
            115                 120                 125
Tyr Val Phe Cys Phe Leu Leu Asn Ala Ile Leu Tyr Ala His Ile Gln
130                 135                 140
Cys Leu Asn Ala Ala Leu Tyr Asn Leu Leu Ile Arg Cys Phe Lys Ala
145                 150                 155                 160
Ala Phe Val Tyr Ile Pro Leu Phe Leu Ile Asn Thr Val Ser Ala Thr
                165                 170                 175
Gln Leu Val Lys Asn Gly Thr Gly Cys Asn Gly Trp Phe Tyr Asn Ala
            180                 185                 190
Ala Thr Lys Tyr Pro Leu Leu Lys Asn Val Tyr Val Phe Cys Phe Leu
            195                 200                 205
Leu Pro Met Asn Ala Thr Leu His Asp Ile Ile Leu Glu Cys Val Lys
    210                 215                 220
Ala Ala Ala Leu Tyr Gly Val Ser Phe Ser Glu Leu Lys Gln Val Asp
225                 230                 235                 240
Tyr Tyr Gly Leu Tyr Tyr Gly Ala Tyr Tyr Met Thr Asp Ala Gly Thr
                245                 250                 255
Trp Asn Ala Ala Pro Tyr Ala Val Cys Asp Lys Cys Phe Lys Gln Gly
            260                 265                 270
Ala Met Leu Ala Val Phe Lys Lys Ala Ala Val Leu Leu Leu
    275                 280                 285
Val Arg Tyr Lys Asn Ala Ala Ala Ser Tyr Phe Gly Met Ser Phe Ile
    290                 295                 300
His Phe Lys Ala Ala Lys Leu Leu Ser Lys Leu Leu Cys Val Asn Ala
305                 310                 315                 320
Ala Ala Ala Thr Met Cys Arg His Tyr Lys Arg Asn Ala Ala Ala Ser
                325                 330                 335
Thr Val Ser Val Gly Thr Ala Lys Asn Ala Ala Leu Ser Gln Met Val
            340                 345                 350
Gln Trp Ala Tyr Lys Leu Thr Asn Thr Gly Leu Tyr Asn Val Asn Ala
    355                 360                 365
Ala Ala Thr Cys Val Ser His Arg Gly Leu Tyr Asn Ala Ala Lys Ser
    370                 375                 380
Ala Ile Val Thr Leu Thr Tyr Lys Ala Ala Ala Asp Ser Val Tyr Gly
385                 390                 395                 400
Asp Thr Leu Glu Arg Asn Met Tyr Val Cys His Val Pro Leu Asn
                405                 410                 415
Ala Ala Arg Phe His Asn Ile Arg Gly Arg Phe Lys Ala Ala Phe Val
            420                 425                 430
Val Tyr Arg Asp Ser Ile Pro Lys Asn Ala Ser Leu Gln Asp Ile Glu
            435                 440                 445
Ile Thr Cys Val Lys Ala Val Tyr Asp Phe Ala Phe Arg Asp Leu Cys
    450                 455                 460
Ile Lys Tyr Met Leu Asp Leu Gln Pro Glu Thr Val Asn Ala Ala Ala
465                 470                 475                 480
Gly Thr Leu Gly Ile Val Cys Pro Val Asn Ser Val Ile Cys Phe Val
                485                 490                 495
```

```
Asn Ser Lys Asn Ala Thr Leu Glu Lys Leu Thr Asn Thr Gly Leu Tyr
                500                 505                 510

Asn Ala Gly Leu Tyr Tyr Val His Glu Gly Ile Arg Thr Tyr Phe Val
            515                 520                 525

Gln Gly Pro Gly Pro Gly Phe Leu Asn Thr Val Ala Ile Pro Asp Ser
        530                 535                 540

Val Gln Ile Leu Val Gly Pro Gly Pro Gly Gln Arg Phe His Asn Ile
545                 550                 555                 560

Arg Gly Arg Trp Thr Gly Arg Cys Met Gly Pro Gly Pro Gly Thr Asn
                565                 570                 575

Thr Gly Leu Tyr Asn Leu Leu Ile Arg Cys Leu Arg Cys Gln Gly Pro
            580                 585                 590

Gly Pro Gly Ile Glu Phe Ile Thr Phe Leu Gly Ala Leu Lys Ser Phe
        595                 600                 605

Leu Lys Gly Pro Gly Pro Gly Glu Trp Ile Gln Arg Gln Thr Val
    610                 615                 620

Leu Gln His Ser Phe Asn Gly Pro Gly Pro Gly Leu Phe Val Val Tyr
625                 630                 635                 640

Arg Asp Ser Ile Pro His Ala Ala Cys His Lys Gly Pro Gly Pro Gly
                645                 650                 655

Ile Arg Thr Leu Glu Asp Leu Leu Met Gly Thr Leu Gly Ile Val Gly
            660                 665                 670

Pro Gly Pro Gly Leu Asp Leu Gln Pro Glu Thr Thr Asp Leu Tyr Cys
        675                 680                 685

Tyr Glu Gln Gly Pro Gly Pro Gly Leu Gln Ala Ile Glu Leu Gln Leu
    690                 695                 700

Thr Leu Glu Thr Ile Tyr Asn Gly Pro Gly Pro Gly Phe Gln Gln Leu
705                 710                 715                 720

Phe Leu Asn Thr Leu Ser Phe Val Cys Pro Trp Gly Pro Gly Pro Gly
                725                 730                 735

Trp Lys His Met Arg Leu Glu Cys Ala Ile Tyr Tyr Lys Ala Arg Gly
            740                 745                 750

Pro Gly Pro Gly Leu Cys Thr Glu Leu Gln Thr Thr Ile His Asp Ile
        755                 760                 765

Ile Leu Glu Gly Pro Gly Pro Gly Phe Lys Thr Leu Ile Gln Pro Phe
    770                 775                 780

Ile Leu Tyr Ala His Ile Gln Gly Pro Gly Pro Gly Leu Tyr Trp Tyr
785                 790                 795                 800

Lys Thr Gly Ile Ser Asn Ile Ser Glu Val Tyr Gly Pro Gly Pro Gly
                805                 810                 815

Glu Val Phe Glu Phe Ala Phe Lys Asp Leu Phe Val Val Tyr Arg Gly
            820                 825                 830

Pro Gly Pro Gly His Lys Ala Ile Glu Leu Gln Met Ala Leu Gln Gly
        835                 840                 845

Leu Ala Gln Gly Pro Gly Pro Gly Ala Lys Phe Val Ala Ala Trp Thr
    850                 855                 860

Leu Lys Ala Ala Ala
865

<210> SEQ ID NO 161
<211> LENGTH: 2607
<212> TYPE: DNA
<213> ORGANISM: artificial
<220> FEATURE:
<223> OTHER INFORMATION: Human papillomavirus polyepitope construct
```

<400> SEQUENCE: 161

```
aagagcctgt tggcatgag cctgatgaag aacagcaccg ccgctgccct ctattggtac      60
aaaaaggccg cctgctacag cctgtacggc accaccttca aggctgctgc cgtggcctgg    120
gacagcgtgt actacatgaa gagcaccgac ctgcgggacc acatcgacta caacatcagc    180
gactaccggc actactgcta caaggccgcc caggtggtgc ccgcctacaa catctccaag    240
aacggctaca acaccttcta catcgagttc aagctccagg acaagatcat cgaccactac    300
aaagccgcct gcctgtacct gcacatccag agtctgaacg cagccgctgc aaccctccag    360
gacatcgtgc tgcacggcac cgtgtacgtg ttctgcttcc tgctgaacgc catcctgtac    420
gcccacatcc agtgtctgaa tgccgccctg tacaacctgc tgatccggtg ctttaaggcc    480
gccttcgtgt acatccccct gtttctgatc aacaccgtga cgccaccca gctggtgaag    540
aatggcaccg gctgcaacgg ctggttctac aatgccgcca ccaagtaccc cctgctgaag    600
aacgtgtatg tgttttgttt tctgctgccc atgaacgcca cactgcacga cattatcctg    660
gaatgcgtca aggccgctgc cctgtatggc gtgagcttca gcgagctgaa gcaggtggac    720
tactacggcc tgtactacgg cgcctactac atgaccgacg ccggcacctg gaatgccgcc    780
ccttacgccg tgtgcgacaa gtgcttcaag cagggcgcca tgctggccgt gttcaagaaa    840
gccgctgccg tggtgctgct gctggtgcgg tataagaatg ccgccgccag ctacttcggc    900
atgagcttca tccactttaa agccgccaag ctgctgtcta gctgctgtg cgtgaatgcc    960
gctgctgcca aatgtgccg gcactacaag agaaatgccg ctgccagcac cgtgagcgtg   1020
ggcaccgcca agaacgccgc cctgagccag atggtgcagt gggcctacaa gctgaccaac   1080
accggcctgt acaacgtgaa cgccgctgcc acctgcgtga ccaccgggg cctgtataac   1140
gccgccaaga gcgccatcgt gaccctgacc tataaggccg ctgccgacag cgtgtacggc   1200
gacaccctgg aacggaacat gtacgtgtgc tgccacgtgc ccctgaatgc cgccaggttc   1260
cacaacatcc ggggcaggtt caaagccgcc tttgtggtgt accgggacag catccccaag   1320
aatgccagcc tccaggatat tgagatcacc tgtgtgaagg ccgtgtacga cttcgccttc   1380
cgggacctgt gcatcaagta catgctggac ctccagcccg agacagtgaa cgccgccgct   1440
ggcacactgg gcatcgtgtg ccccgtgaac agcgtgatct gcttcgtgaa cagcaaaaac   1500
gccacccctgg aaaagctgac aaatacaggg ctgtacaatg ccggcctgta ttacgtgcac   1560
gagggcatcc ggacctactt cgtgcagggc ccagggccag gcttcctgaa caccgtggcc   1620
atccccgact ccgtgcagat cctggtcggc caggaccag gcagcggtt ccacaatatc   1680
agaggccggt ggaccggcag atgcatgggc ccaggacctg gcacaaatac cggactgtat   1740
aatctgctga ttcgctgcct gcggtgccag ggtccaggac caggcatcga gtttatcacc   1800
tttctgggcg ccctgaagag cttcctgaaa ggacctggac aggacccga gtggattcag   1860
cggcagaccg tgctccagca cagcttcaac ggacccggac ccggcctgtt cgtggtgtac   1920
agagactcca tccccacgc cgcctgtcac aagggacctg gaccaggcat caggaccctg   1980
gaggacctgc tgatgggcac cctgggcatt gtggggcctg gacctggact ggatctccag   2040
cctgaaacca ccgacctgta ctgctacgag caggggccag gacctgggct ccaggctatc   2100
gaactccagc tgaccctgga aaccatctac aatggccccg gaccaggctt ccagcagctg   2160
ttcctgaata ccctgagctt cgtgtgccct tggggaccag gccccggatg gaagcacatg   2220
cggctggaat gcgccatcta ctacaaggcc agaggcccag gacccggact gtgcaccgaa   2280
```

-continued

```
ctccagacca ccatccacga catcattctg gaaggaccag ggccaggctt taagaccctg    2340
atccagccct tcattctgta tgcccacatt cagggacctg ggcctggcct gtattggtat    2400
aagaccggca tcagcaacat ctccgaggtg tacgggcctg gaccaggcga ggtgttcgag    2460
ttcgccttca aggatctgtt tgtggtgtat agaggccccg gacctggcca caaggccatt    2520
gaactccaga tggccctcca ggggctggcc caggaccag gccctggcgc caagttcgtg    2580
gccgcctgga ccctgaaagc cgccgcc                                        2607
```

<210> SEQ ID NO 162  
<211> LENGTH: 885  
<212> TYPE: PRT  
<213> ORGANISM: artificial  
<220> FEATURE:  
<223> OTHER INFORMATION: Human papillomavirus polyepitope construct

<400> SEQUENCE: 162

```
Ala Thr Cys Val Ser His Arg Gly Leu Tyr Asn Ala Ala Ser Thr Asp
1               5                   10                  15

Leu Arg Asp His Ile Asp Tyr Asn Ala Ala Ala Ala Thr Met Cys Arg
                20                  25                  30

His Tyr Lys Arg Asn Ala Ile Leu Tyr Ala His Ile Gln Cys Leu Asn
            35                  40                  45

Ala Ala Ala Gly Thr Leu Gly Ile Val Cys Pro Val Asn Ala Ala Ala
        50                  55                  60

Cys Tyr Ser Leu Tyr Gly Thr Thr Phe Lys Ala Ala Ala Asp Ser Val
65                  70                  75                  80

Tyr Gly Asp Thr Leu Glu Arg Asn Gln Val Val Pro Ala Tyr Asn Ile
                85                  90                  95

Ser Lys Asn Ala Ala Leu Tyr Asn Leu Leu Ile Arg Cys Phe Lys Ala
            100                 105                 110

Ala Phe Val Tyr Ile Pro Leu Phe Leu Ile Asn Tyr Tyr Met Thr Asp
        115                 120                 125

Ala Gly Thr Trp Gly Ala Val Val Leu Leu Leu Val Arg Tyr Lys Asn
    130                 135                 140

Ala Ala Ile Ser Asp Tyr Arg His Tyr Cys Tyr Lys Ala Ala Thr Val
145                 150                 155                 160

Ser Ala Thr Gln Leu Val Lys Lys Ala Ser Thr Ala Ala Ala Leu Tyr
                165                 170                 175

Trp Tyr Lys Lys Ala Ala Phe Val Val Tyr Arg Asp Ser Ile Pro Lys
            180                 185                 190

Asn Ala Ser Tyr Phe Gly Met Ser Phe Ile His Phe Lys Ala Ala Tyr
        195                 200                 205

Met Leu Asp Leu Gln Pro Glu Thr Val Asn Ala Val Tyr Asp Phe
    210                 215                 220

Ala Phe Arg Asp Leu Cys Ile Lys Ala Ala Leu Gln Asp Lys Ile Ile
225                 230                 235                 240

Asp His Tyr Lys Ala Ala Thr Leu His Asp Ile Ile Leu Glu Cys Val
                245                 250                 255

Lys Lys Leu Thr Asn Thr Gly Leu Tyr Asn Val Gly Ala Ala Ala Ser
            260                 265                 270

Val Ile Cys Phe Val Asn Ser Lys Gly Ala Ala Ala Met Tyr Val Cys
        275                 280                 285

Cys His Val Pro Leu Asn Ala Ser Leu Gln Asp Ile Glu Ile Thr Cys
    290                 295                 300
```

```
Val Lys Cys Leu Tyr Leu His Ile Gln Ser Leu Asn Ala Ala Thr Lys
305                 310                 315                 320

Tyr Pro Leu Leu Lys Asn Val Tyr Val Phe Cys Phe Leu Leu Pro Met
                325                 330                 335

Asn Ala Lys Gln Gly Ala Met Leu Ala Val Phe Lys Lys Ala Ala Leu
            340                 345                 350

Ser Gln Met Val Gln Trp Ala Tyr Lys Ala Ala Pro Tyr Ala Val Cys
        355                 360                 365

Asp Lys Cys Phe Lys Ala Ala Thr Val Tyr Val Phe Cys Phe Leu Leu
    370                 375                 380

Asn Ala Ala Ala Ala Thr Leu Gln Asp Ile Val Leu His Gly Ala Lys
385                 390                 395                 400

Ser Leu Phe Gly Met Ser Leu Met Lys Asn Gly Thr Gly Cys Asn Gly
                405                 410                 415

Trp Phe Tyr Asn Ala Arg Phe His Asn Ile Arg Gly Arg Phe Lys Ala
                420                 425                 430

Ala Lys Leu Leu Ser Lys Leu Leu Cys Val Asn Ala Ala Ala Ser Thr
            435                 440                 445

Val Ser Val Gly Thr Ala Lys Asn Val Ala Trp Asp Ser Val Tyr Tyr
    450                 455                 460

Met Lys Ala Ala Gly Tyr Asn Thr Phe Tyr Ile Glu Phe Lys Ala
465                 470                 475                 480

Ala Ala Leu Tyr Gly Val Ser Phe Ser Glu Leu Lys Gln Val Asp Tyr
                485                 490                 495

Tyr Gly Leu Tyr Tyr Asn Ala Ala Lys Ser Ala Ile Val Thr Leu Thr
        500                 505                 510

Tyr Lys Ala Ala Thr Leu Glu Lys Leu Thr Asn Thr Gly Leu Tyr
    515                 520                 525

Asn Ala Gly Leu Tyr Tyr Val His Glu Gly Ile Arg Thr Tyr Phe Val
530                 535                 540

Gln Gly Pro Gly Pro Gly Phe Leu Asn Thr Val Ala Ile Pro Asp Ser
545                 550                 555                 560

Val Gln Ile Leu Val Gly Pro Gly Pro Gly Gln Arg Phe His Asn Ile
                565                 570                 575

Arg Gly Arg Trp Thr Gly Arg Cys Met Gly Pro Gly Pro Gly Thr Asn
                580                 585                 590

Thr Gly Leu Tyr Asn Leu Leu Ile Arg Cys Leu Arg Cys Gln Gly Pro
            595                 600                 605

Gly Pro Gly Ile Glu Phe Ile Thr Phe Leu Gly Ala Leu Lys Ser Phe
    610                 615                 620

Leu Lys Gly Pro Gly Pro Gly Pro Glu Trp Ile Gln Arg Gln Thr Val
625                 630                 635                 640

Leu Gln His Ser Phe Asn Gly Pro Gly Pro Gly Leu Phe Val Val Tyr
                645                 650                 655

Arg Asp Ser Ile Pro His Ala Ala Cys His Lys Gly Pro Gly Pro Gly
            660                 665                 670

Ile Arg Thr Leu Glu Asp Leu Leu Met Gly Thr Leu Gly Ile Val Gly
        675                 680                 685

Pro Gly Pro Gly Leu Asp Leu Gln Pro Glu Thr Thr Asp Leu Tyr Cys
    690                 695                 700

Tyr Glu Gln Gly Pro Gly Pro Gly Leu Gln Ala Ile Glu Leu Gln Leu
705                 710                 715                 720

Thr Leu Glu Thr Ile Tyr Asn Gly Pro Gly Pro Gly Phe Gln Gln Leu
```

```
                    725                 730                 735
Phe Leu Asn Thr Leu Ser Phe Val Cys Pro Trp Gly Pro Gly Pro Gly
            740                 745                 750

Trp Lys His Met Arg Leu Glu Cys Ala Ile Tyr Tyr Lys Ala Arg Gly
            755                 760                 765

Pro Gly Pro Gly Leu Cys Thr Glu Leu Gln Thr Thr Ile His Asp Ile
        770                 775                 780

Ile Leu Glu Gly Pro Gly Pro Gly Phe Lys Thr Leu Ile Gln Pro Phe
785                 790                 795                 800

Ile Leu Tyr Ala His Ile Gln Gly Pro Gly Pro Gly Leu Tyr Trp Tyr
                805                 810                 815

Lys Thr Gly Ile Ser Asn Ile Ser Glu Val Tyr Gly Pro Gly Pro Gly
            820                 825                 830

Glu Val Phe Glu Phe Ala Phe Lys Asp Leu Phe Val Val Tyr Arg Gly
            835                 840                 845

Pro Gly Pro Gly His Lys Ala Ile Glu Leu Gln Met Ala Leu Gln Gly
        850                 855                 860

Leu Ala Gln Gly Pro Gly Pro Gly Ala Lys Phe Val Ala Ala Trp Thr
865                 870                 875                 880

Leu Lys Ala Ala Ala
                885
```

<210> SEQ ID NO 163
<211> LENGTH: 2655
<212> TYPE: DNA
<213> ORGANISM: artificial
<220> FEATURE:
<223> OTHER INFORMATION: Human papillomavirus polyepitope construct

<400> SEQUENCE: 163

```
gccacctgcg tgagccacag gggcctctac aacgccgcca gcaccgacct gcgggaccac      60
atcgactaca atgctgctgc cgctacaatg tgccggcact acaagcggaa cgccatcctg     120
tacgcccaca tccagtgcct gaatgctgcc gctggcacac tgggcatcgt gtgccccgtg     180
aatgccgccg cctgctacag cctgtacggg accaccttca aggccgctgc cgactccgtg     240
tacggcgaca ccctggaacg gaaccaggtg gtgcccgcct acaacatctc taagaatgcc     300
gctctgtaca acctgctgat ccggtgcttt aaggctgcct tcgtgtacat ccccctgttt     360
ctgatcaact actacatgac cgacgccggc acatggggag ccgtggtgct gctgctggtg     420
cggtacaaga tgccgccat cagcgactac cggcactact gctacaaggc cgccaccgtc     480
agcgccaccc agctggtgaa gaaggccagc acagccgccg ctctctattg gtataaaaaa     540
gccgcctttg tggtgtaccg ggacagcatc cccaagaacg ccagctactt cggcatgagc     600
ttcatccact tcaaagccgc ctacatgctg acctccagc ccgagaccgt gaacgctgcc     660
gtgtacgact cgccttccg ggacctgtgc attaaagccg cactccagga caagatcatc     720
gaccattata aagcagccac cctgcatgat attattctgg aatgcgtgaa gagctgacc     780
aacaccggcc tctataacgt gggagccgcc gcctctgtga tctgcttcgt gaacagcaag     840
ggggctgccg ccatgtatgt gtgctgccac gtgcccctga acgcctctct ccaggatatt     900
gagatcacct gtgtgaagtg cctgtacctg cacattcagt ctctgaatgc cgccaccaag     960
tacccctgc tgaagaacgt gtatgtcttt tgcttcctgc tgcccatgaa cgccaagcag    1020
ggcgccatgc tggccgtgtt caaaaaggcc gccctgagcc agatggtgca gtgggcctac    1080
aaagccgccc cttacgccgt gtgcgacaag tgtttaagg ccgccacagt gtacgtgttt    1140
```

```
                                                        -continued tgttttctgc tgaatgccgc tgccgccacc ctccaggaca tcgtgctgca cggcgccaag    1200
tccctgttcg gcatgtccct gatgaagaat ggcaccggct gcaacggctg gttctacaac    1260
gcccggttcc acaacatccg gggcaggttt aaagccgcca agctgctgtc taagctgctg    1320
tgtgtgaacg ccgccgcttc caccgtgagc gtgggcaccg ccaagaacgt ggcctgggac    1380
agcgtgtact acatgaaagc agcagccggg tacaacacct tctacatcga gtttaaagct    1440
gccgccctgt acgcgtgag cttcagcgag ctgaagcagg tggactacta cggcctgtac     1500
tataacgccg ccaagagcgc catcgtgacc ctgacctata agccgccgc cacactggaa     1560 aagctgacca atacagggct gtacaatgcc ggcctgtatt acgtgcacga gggcatccgg    1620
acctacttcg tgcagggccc agggccaggc ttcctgaaca ccgtggccat ccccgactcc    1680
gtgcagatcc tggtcggccc aggaccaggg cagcggttcc acaatatcag aggccggtgg    1740
accggcagat gcatgggccc aggacctggc acaaataccg gactgtataa tctgctgatt    1800
cgctgcctgc ggtgccaggg tccaggacca ggcatcgagt ttatcaccctt tctgggcgcc   1860 ctgaagagct tcctgaaagg acctggacca ggacccgagt ggattcagcg gcagaccgtg    1920
ctccagcaca gcttcaacgg acccggaccc ggcctgttcg tggtgtacag agactccatc    1980
ccccacgccg cctgtcacaa gggacctgga ccaggcatca ggaccctgga ggacctgctg    2040
atgggcaccc tgggcattgt ggggcctgga cctggactgg atctccagcc tgaaaccacc    2100
gacctgtact gctacgagca ggggccagga cctgggctcc aggctatcga actccagctg    2160
accctggaaa ccatctacaa tggccccgga ccaggcttcc agcagctgtt cctgaatacc    2220
ctgagcttcg tgtgcccttg gggaccaggg cccggatgga agcacatgcg gctggaatgc    2280
gccatctact acaaggccag aggcccagga cccggactgt gcaccgaact ccagaccacc    2340
atccacgaca tcattctgga aggaccaggg ccaggcttta gaccctgat ccagcccttc     2400 attctgtatg cccacattca gggacctggg cctggcctgt attggtataa gaccggcatc    2460
agcaacatct ccgaggtgta cgggcctgga ccaggcgagg tgttcgagtt cgccttcaag    2520
gatctgtttg tggtgtatag aggccccgga cctggccaca aggccattga actccagatg    2580
gccctccagg ggctggccca gggaccaggc cctggcgcca agttcgtggc cgcctggacc    2640
ctgaaagccg ccgcc                                                     2655
```